US008846620B2

(12) United States Patent
Turecek et al.

(10) Patent No.: US 8,846,620 B2
(45) Date of Patent: Sep. 30, 2014

(54) RESORPTION ENHANCERS AS ADDITIVES TO IMPROVE THE ORAL FORMULATION OF NON-ANTICOAGULANT SULFATED POLYSACCHARIDES

(75) Inventors: Peter Turecek, Klosterneuburg (AT); Susanne Vejda, Vienna (AT)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 0 days.

(21) Appl. No.: 13/552,569

(22) Filed: Jul. 18, 2012

(65) Prior Publication Data

US 2013/0035288 A1 Feb. 7, 2013

Related U.S. Application Data

(60) Provisional application No. 61/509,514, filed on Jul. 19, 2011.

(51) Int. Cl.
| | |
|---|---|
| *A61K 38/37* | (2006.01) |
| *C07K 14/755* | (2006.01) |
| *A61K 38/36* | (2006.01) |
| *A61P 7/02* | (2006.01) |
| *C07K 14/745* | (2006.01) |
| *A01N 43/04* | (2006.01) |
| *A61K 31/715* | (2006.01) |
| *A61K 38/48* | (2006.01) |
| *A61K 47/42* | (2006.01) |
| *A61K 47/12* | (2006.01) |
| *A61K 47/28* | (2006.01) |
| *A61K 47/36* | (2006.01) |

(52) U.S. Cl.
CPC .............. *A61K 38/4846* (2013.01); *A61K 47/42* (2013.01); *A61K 47/12* (2013.01); *A61K 47/28* (2013.01); *A61K 38/4853* (2013.01); *A61K 47/36* (2013.01)
USPC ............................. 514/14.1; 514/13.7; 514/54

(58) Field of Classification Search
None
See application file for complete search history.

(56) References Cited

U.S. PATENT DOCUMENTS

| | | | |
|---|---|---|---|
| 6,593,311 | B2 | 7/2003 | Sakai et al. |
| 7,265,097 | B2 * | 9/2007 | Kydonieus et al. ............. 514/55 |
| 7,829,549 | B2 | 11/2010 | Johnson |
| 2003/0203845 | A1 | 10/2003 | Knudsen et al. |
| 2005/0282771 | A1 | 12/2005 | Johnson |
| 2005/0282775 | A1 | 12/2005 | Kennedy |
| 2007/0218076 | A1 | 9/2007 | Michailovna et al. |
| 2008/0107678 | A1 | 5/2008 | Johnson |
| 2009/0098185 | A1 | 4/2009 | Johnson |
| 2009/0269325 | A1 | 10/2009 | Johnson |
| 2011/0110921 | A1 | 5/2011 | Dockal et al. |
| 2011/0172156 | A1 | 7/2011 | Dockal et al. |

FOREIGN PATENT DOCUMENTS

| | | |
|---|---|---|
| CN | 1328062 | 12/2001 |
| CN | 1344565 | 4/2002 |
| EP | 251134 | 1/1988 |
| EP | 1327448 | 7/2003 |
| JP | 7215990 | 8/1995 |
| JP | 3371124 | 9/1998 |
| JP | 410324508 | 12/1998 |
| JP | 2003171262 | 6/2003 |
| WO | WO9815292 | 4/1998 |
| WO | WO 9918961 | 4/1999 |
| WO | WO 2004029095 | 4/2004 |
| WO | WO 2005117912 A1 * | 12/2005 |
| WO | WO 2007127298 | 11/2007 |
| WO | WO2008090631 | 7/2008 |
| WO | WO 2008103234 | 8/2008 |
| WO | WO 2010020423 A2 * | 2/2010 |

OTHER PUBLICATIONS

Grabovac V and Bernkop-Schnurch A "Improvement of the intestinal membrane permeability of low molecular weight heparin by complexation with stem bromelain" Intl J Pharmaceutics 326:153-159. Published online Jul. 4, 2006.*
Liu et al "Improved coagulation in bleeding disorders by Non-Anticoagulant Sulfated Polysaccharides (NASP)" Thrombosis and Haemostasis 95:68-76. Published online Dec. 12, 2005.*
Matsuhisa et al "Tight junction modulator and drug delivery" Exp Opin Drug Delivery 6:509-515. Published May 2009.*
Official Action in U.S. Appl. No. 11/140,504, Mail Date Aug. 4, 2008.
Official Action in U.S. Appl. No. 11/140,504, Mail Date Mar. 16, 2009.
Official Action in U.S. Appl. No. 12/316,632, Mail Date Jun. 25, 2009.
Official Action in U.S. Appl. No. 13/111,684, Mail Date Jan. 27, 2012.
Official Action in U.S. Appl. No. 12/449,712, Mail Date Apr. 2, 2012.
Official Action in U.S. Appl. No. 12/893,798, Mail Date May 2, 2012.
Official Action in U.S. Appl. No. 13/111,684, Mail Date Jul. 2, 2012.
Official Action in U.S. Appl. No. 12/893,798, Mail Date Aug. 10, 2012.
Official Action in U.S. Appl. No. 12/449,712, Mail Date Oct. 5, 2012.
Bates, et al., "The New Heparins," Coron. Artery Dis. 2(2-3):65-74 (1998).
Bishop, et al., "Recombinant Biologics for Treatment of Bleeding Disorders," Nat. Rev. Drug Discov. 2.(8):684-94 (2004).
Bourin, et al., "Glycosaminoglycans and the Regulation of Blood Coagulation," Biochem J. 289(Pt 2):313-30 (1993).
Broze, "The Role of Tissue Factor Pathway Inhibitor in a Revised Coagulation Cascade," Semin. Haematol. 29(3): 159-69 (1992).

(Continued)

*Primary Examiner* — Maury Audet
*Assistant Examiner* — Zachary J Miknis
(74) *Attorney, Agent, or Firm* — Khin Chin; Bret E. Field; Bozicevic, Field & Francis, LLP

(57) ABSTRACT

Aspects of the invention include methods for enhancing blood coagulation in a subject. In practicing methods according to certain embodiments, an amount of a non-anticoagulant sulfated polysaccharide (NASP) in combination with a gastrointestinal epithelial barrier permeation enhancer is orally administered to a subject in a manner sufficient to enhance blood coagulation in the subject. Compositions and kits for practicing methods of the invention are also described.

16 Claims, 24 Drawing Sheets

(56) References Cited

OTHER PUBLICATIONS

Broze, "The Rediscovery and Isolation of TFPI," Journal of Thrombosis and Haemostasis, 1(8): 1671-1675 (2003).
Brummel, et al., "Factor Viia Replacement Therapy in Factor VII Deficiency," J. Thromb. Haemost. 6(10): 1735-44 (2004).
Carcao, et al., "Prophylactic Factor Replacement in Hemophilia," Blood Rev., vol. 18, pp. 101-113 (2004).
Church, et al., "Antithrombin Activity of Fucoidan. The Interaction of Fucoidan With Heparin Cofactor II, Antithrombin III, and Thrombin," J. Bioi. Chem. 264(6):3618-23 (1989).
Colliec, et al., "Anticoagulant Properties of a Fucoidan Fraction," Thrombosis Research, 64: 143-154 (1991).
Davie, et al., "The Coagulation Cascade: Initiation, Maintenance, and Regulation," Biochemistry 30(43): 10363-70 (1991).
Erhardtsen, et al., "Blocking of Tissue Factor Pathway Inhibitor (TFPI) Shortens the Bleeding Time in Rabbits With Antibody Induced Haemophilia A," Blood Coagul. Fibrinolysis 2(5):388-94 (1995).
Fryer, et al., "Selective O-Desulfation Produces Nonanticoagulant Heparin That Retains Pharmacological Activity in the Lung," J Pharmacol Exp. Ther. vol. 282, No. 1, pp. 208-19 (1997).
Gailani et al., "Factor XI Activation in a Revised Model of Blood Coagulation" Science. (1991) vol. 253, No. 5022 pp. 909-912.
Giedrojc, et al., "Comparative Study on the In Vitro and In Vivo Activities of Heparinoids Derivative Investigated on the Animal Model," J. Cardiovasc. Pharmacol. 34(3):340-5 (1999).
Goodman-Gilman, "The Pharmacological Basis of Therapeutics" editors Joel G. Hardman and Lee E. Limbard; published by The McGraw-Hill Companies Inc., (2001) pp. 54-56.
Grabovac, et al. "Improvement of the intestinal membrane permeability of low molecular weight heparin by complexation with stem bromelain" International Journal of Pharmaceutics 326; pp. 153-159 (2006).
Granert, et al., "Effects of Polysaccharide Fucoidin on Cerebrospinal Fluid Interleukin-l and Tumor Necrosis Factor Alpha in Pneumococcal Meningitis in the Rabbit," Irifect. Immun. 67(5):2071-4 (1999).
Hirsh, et al., "New Anticoagulants," Blood, vol. 105, No. 2, pp. 453-463 (2005).
Johnson, et al. "Discovery of tight junction modulators: significance for drug development and delivery", Drug Discovery Today vol. 13, Nos. 5/6 (Mar. 2008).
Johnson, et al., "Novel Anticoagulants Based on Inhibition of the Factor ViialTissue Factor Pathway," Coron. Artery Dis. 2(2-3):83-7 (1998).
Kitamura, et al. "Fucoidan from Brown Seaweed *Laminaria* Augustata Var. Lingissima" Agricultural and Biological Chemistry Japan Soc. for Bioscience, Biotechnology and Agrochem. vol. 55, No. 2, (Jan. 1991).
Kleesiek, et al., "The 536C-->T Transition in the Human Tissue Factor Pathway Inhibitor (TFPJ) Gene Is Statistically Associated With a Higher Risk for Venous Thrombosis," Thromb. Haemost. 82(1):1-5 (1999).
Kleim et al., "Successful renal transplantation in severe von Willebrand's disease" Nephrology Dialysis Transplantation vol. 9, p. 837-838 (1994).
Lee, "Von Willebrand Disease, Hemophilia A and B, and Other Factor Deficiencies," Int. Anesthesiol. Clin. 42(3):59-76 (2004).
Li et al., "Fucoidan: structure and bioactivity" Molecules (2008) vol. 13, No. 8 pp. 1671-1695 XP002574600.
Li et al, "Toxicological Evaluation of Fucoidian Extracted from *Laiminara japonical* in Wistar Rats" Foo Chem Toxicol 43: 421-426 (2005).
Liu, et al., "Improved coagulation in bleeding disorders by Non-Anticoagulant Sulfated Polysaccharides (NASP)," Thrombosis and Haemostasis 95:68-76 (2006).
Luyt, et al., "Low-Molecular-Weight Fucoidan Promotes Therapeutic Revascularization in a Rat Model of Critical Hindlimb Ischemia," J. Pharmacol. Exp. Ther. 305(1):24-30 (2003).
Mabeau S. et al., "Fractionation and Analysis of Fucans from Brown Algae," Phytochemistry, vol. 29, No. 8, pp. 2441-2446 (1990).
MacGregor, et al., "Metabolism of Sodium Pentosan Polysulphate in Man Measured by a New Competitive Binding Assay for Sulphated Polysaccharides—Comparison With Effects Upon Anticoagulant Activity, Lipolysis and Platelet Alpha-Granule Proteins," Thromb. Haemost. 53(3):411-414 (1985).
Mann, "Thrombin: Can't Live Without It; Probably Die From It," Chest 124(3 Suppl):1S-3S (2003).
Mann, "Thrombin Formation," Chest 124(3 Suppl):4S-10S (2003).
Marais, et al., "A fucoidan fraction from *Ascophyllum nodosum*," Carbohydrate Research, Elsevier Scientific Publishing Company, vol. 336, No. 2 (2001).
McAuliffe, et al. "Carbohydrate drugs—an ongoing challenge," Chem.Indus. Magazine 2:170-4 (1997).
McCaffrey et al. "Fucoidan is a Non-Anticoagulant Inhibitor of Intimal Hyperplasia," Biochem. Biophys. Res. Commun. 184(2):773-81 (1992).
Millet, et al. "Antithrombotic and Anticoagulant Activities of a Low Molecular Weight Fucoidan by the Subcutaneous Route," Thromb. Haemost. 81:391-5 (1999).
Mourao, "Use of Sulfated Fucans as Anticoagulant and Antithombotic Agents: Future Perspectives," Curr Pharma Des 10: 967-981 (2004).
Nagaoka, et al. "Structural Study of Fucoidan from Cladosiphon Okamuranus Tokida", Glycoconjugate Journal, 16, 19-26 (1999).
Nishino T. et al., "Isolation and Partial Characterization of a Novel Amino Sugar—Fucan Sulfate from Commercial *Fucus Vesiculosus* Fucoidan," Carbohydrate Research, Elsevier Scientific Publishing Company, vol. 255, pp. 213-224 (1994).
Nordfang, et al. "Inhibition of Extrinsic Pathway Inhibitor Shortens the Coagulation Time of Normal Plasma and of Hemophilia Plasma," Thromb. Haemost. 66(4):464-67 (1991).
Novotny, et al. "Purification and Properties of Heparin-Releasable Lipoprotein-Associated Coagulation Inhibitor," Blood 78(2):394-400 (1991).
Orgueria, et al. "Modular Synthesis of Heparin Oligosaccharides," Chem. Eur. J. 2(1):140-69 (2003).
Prasad et al., "Efficacy and safety of a new-class hemostatic drug candidate, AV513, in dogs with homphilia A" Blood, vol. 111, No. 2 (2008) pp. 672-679 XP002574599.
Raimondi, et al. "Bile acids modulate tight junction structure and barrier function of Caco-2 monolayers via EGFR activation" Am. J. Physiol. Gastroinest Liver Phisol. 294: G906-G913 (2008).
Rapaport, et al., "The Tissue Factor Pathway: How It Has Become A 'Prima Ballerina'," Thromb. Haemost 74(1):7-17 (1995).
Roberts, et al., "Current Concepts of Hemostasis: Implications for Therapy," Anesthesiology 100(3):722-30 (2004).
Schipper, et al. "Chitosans as Absorption Enhancers for Poorly Absorbable Drugs. Influence of Molecular Weight and Degree of Acetylation on Drug Transport Across Human Intestinal Epithelial (Caco-2) Cells" Pharmaceutical Research, vol. 13, No. 11 (1996).
Sinay, "Sugars Slide Into Heparin Activity," Nature 398(6726):377-378 (1999).
Springer G F et al., "Isolation of anticoagulant fractions from crude fucoidin," Proceedings of the Society for Experimental Biology & Medicine, Academic Press Inc., vol. 94, No. 2 (1957).
Thanou, et al. "Mono-N-Carboxymethyl Chitosan (MCC), a Polyampholytic Chitosan Derivative, Enhances the Intestinal Absorption of Low Molecular Weight Heparin Across Intestinal Epithelia In Vitro and In Vivo" Journal of Pharmaceutical Sciences, vol. 90, No. 1; pp. 38-46 (Jan. 2001).
Toida et al. "Structure and Bioactivity of Sulfated Polysaccharides," Trends in Glyoeseienee and Glyeoteehnology, vol. 15, No. 81, pp. 29-46 (2003).
Veer Van' T C. et al., "Regulation of Tissue Factor Initiated Thrombin Generation by the Stoichiometric Inhibitors Tissue Factor Pathway Inhibitor, Antithrombin-III, and Heparin CoFactor-II", Journal of Biological Chemistry, American Society of Biolochemical Biologists, Birmingham, US, 272(7):4367-4377 (1997).
Vicente, et al., "Unbalanced Effects of Dermation Sulfates With Different Sulfation Patterns on Coagulation, Thrombosis and Bleeding," Thromb Haenos 86(5): 1215-1220 (2001).
Wang, et al., "N-Desulfated Non-Anticoagulant Heparin Inhibits Leukocyte Adhesion and Transmigration In Vitro and Attenuates

(56) References Cited

OTHER PUBLICATIONS

Acute Peritonitis and Ischemia and Reperfusion Injury In Vivo," Inflamm. Res. 51(9):435-43 (2002).

Welsch, et al., "Effect of Lipoprotein-Associated Coagulation Inhibitor (LACI) on Thromboplastin-Induced Coagulation of Normal and Hemophiliac Plasmas," Thromb. Res. 64(2):213-22 (1991).

Westrick, et al., "Deficiency of Tissue Factor Pathway Inhibitor Promotes Atherosclerosis and Thrombosis in Mice," Circulation 103(25):3044-6 (2001).

Williams, et al., "Comparative Effects of Heparin and the Sulfatoid GMI474 on Coagulation parameters in Plasma and Blood From Various Species," Gen. Pharmacol. 30(3):337-41 (1998).

Wuillemin et al., "Thrombin-mediated activation of endogenous factor XI in plasma in the presence of physiological glycosaminoglycans occurs only with high concentrations of thrombin," British Journal of Haematology (1996) vol. 92, No. 2, pp. 466-472.

Guggi, et al.,"Improved paracellular uptake by the combination of different types of permeation enhancers", Int J Pharm., 2005, 288(1):141-50.

* cited by examiner

RESORPTION ENHANCERS AS ADDITIVES TO IMPROVE THE ORAL FORMULATION OF NON-ANTICOAGULANT SULFATED POLYSACCHARIDES

CROSS-REFERENCE TO RELATED APPLICATION

Pursuant to 35 U.S.C. §119(e), this application claims priority to U.S. Provisional Application Ser. No. 61/509,514 filed on Jul. 19, 2011, the disclosure of which is herein incorporated by reference.

INTRODUCTION

Bleeding is one of the most serious and significant manifestations of disease, and may occur from a local site or be systemic. Localized bleeding may be associated with lesions and may be further complicated by a defective haemostatic mechanism. Blood clotting is inadequate in bleeding disorders, which may be caused by congenital coagulation disorders, acquired coagulation disorders, or hemorrhagic conditions induced by trauma. Congenital or acquired deficiencies of any of the coagulation factors may be associated with a hemorrhagic tendency. Some congenital coagulation disorders include hemophilia, a recessive X-linked disorder involving a deficiency of coagulation factor VIII (hemophilia A) or factor IX (hemophilia B) and von Willebrands disease, a rare bleeding disorder involving a severe deficiency of von Willebrands factor. Acquired coagulation disorders may arise in individuals without a previous history of bleeding as a result of a disease process. For example, acquired coagulation disorders may be caused by inhibitors or autoimmunity against blood coagulation factors, such as factor VIII, von Willebrand factor, factors IX, V, XI, XII and XIII; or by hemostatic disorders such as caused by liver disease, which may be associated with decreased synthesis of coagulation factors.

SUMMARY

Aspects of the invention include methods for enhancing blood coagulation in a subject. In practicing methods according to certain embodiments, an amount of a non-anticoagulant sulfated polysaccharide (NASP) in combination with a gastrointestinal epithelial barrier permeation enhancer is orally administered to a subject in a manner sufficient to enhance blood coagulation in the subject. Compositions and kits for practicing methods of the invention are also described.

In embodiments of the invention, an amount of a NASP in combination with a gastrointestinal epithelial barrier permeation enhancer is orally administered to a subject in a manner sufficient to enhance blood coagulation. In certain embodiments, the gastrointestinal epithelial barrier permeation enhancer is a tight junction modulator. For example, tight junction modulators provided by the invention may include, but are not limited to proteases, bile acids, polysaccharides, fatty acids and salts thereof and any combination thereof. For example, the tight junction modulator may be a bile acid, such as for instance deoxycholate. In other instances, the tight junction modulator may be a protease, such as bromelain or an enzymatic component of bromelain. In yet other instances, the tight junction modulator may be a polysaccharide, such as chitosan. In still other instances, the tight junction modulator may be a fatty acid or a fatty acid salt, such as sodium caprate.

In certain embodiments, gastrointestinal epithelial barrier permeation enhancers of the invention are a combination of tight junction modulators. For example, in certain instances, a combination of bromelain and chitosan are orally administered with a NASP to a subject in a manner sufficient to enhance blood coagulation in the subject.

In certain embodiments, the present invention provides a method for enhancing blood coagulation by orally administering a composition having an amount of a NASP in combination with a gastrointestinal epithelial barrier permeation enhancer to a subject, where the NASP is a natural NASP. In some instances, the natural NASP is N-acetyl-heparin (NAH), N-acetyl-de-O-sulfated-heparin (NA-de-o-SH), de-N-sulfated-heparin (De-NSH), de-N-sulfated-acetylated-heparin (De-NSAH), periodate-oxidized heparin (POH), chemically sulfated laminarin (CSL), chemically sulfated alginic acid (CSAA), chemically sulfated pectin (CSP), dextran sulfate (DXS), heparin-derived oligosaccharides (HDO), or pentosan polysulfate (PPS). In certain instances, the natural NASP is a fucoidan. For example, in these embodiments, the fucoidan may be Fucoidan GFS 5508005, *Undaria pinnatifida*, depyrogenated; Fucoidan GFS 5508004, *Undaria pinnatifida*; Fucoidan GFS 5508003, *Undaria pinnatifida*; Fucoidan 5307002, *Fucus vesiculosus*, max. MW peak 126.7 kD; Fucoidan VG49, *Fucus vesiculosus*, hydrolyzed sample of 5307002 of lower MW, max. MW peak 22.5 kD; Fucoidan 5308004, *Fucus vesiculosus*; Fucoidan 5308005, *Fucus vesiculosus*; Fucoidan L/FVF1091, *Fucus vesiculosus*; Fucoidan VG201096A, *Fucus vesiculosus*; Fucoidan VG201096B, *Fucus vesiculosus*; Fucoidan VG57, *Undaria pinnatifida*, high charge (high sulphation, deacetylated); Fucoidan VG50, *Ascophyllum nodosum*, max. MW peak 149.7 kD; and combinations thereof.

In other embodiments, the present invention provides a method for enhancing blood coagulation by orally administering a composition having an amount of a NASP in combination with a gastrointestinal epithelial barrier permeation enhancer to a subject, where the NASP is a synthetic NASP. For example, the synthetic NASP may be a sulfated oligomer, such as a sulfated oligosaccharide or a sulfated aliphatic. In certain instances, synthetic NASPs are sulfated pentoses, sulfated hexoses or sulfated cyclodextrins. For example, synthetic NASPs may include, but are not limited to sulfated maltopentoses, sulfated beta-cyclodextrins, sulfated 6-Carboxylcodextrin and derivatives thereof.

In certain embodiments, methods of invention further include orally administering a blood coagulation factor to the subject in conjunction with the composition containing a procoagulant amount of a NASP in combination with a gastrointestinal epithelial barrier permeation enhancer. In these instances, the blood coagulation factor may include but are not limited to factor Xa, factor IXa, factor XIa, factor XIIa, VIIIa, prekallekrein, and high-molecular weight kininogen, tissue factor, factor VIIa, factor Va, factor Xa, factor II, factor V, factor VII, factor VIII, factor IX, factor X, factor XI, factor XII, factor XIII, von Willebrands factor, and combinations thereof. For example, in some embodiments, methods of the invention include orally administering to a subject an amount of a NASP in combination with a gastrointestinal epithelial barrier permeation enhancer and factor VIII. In another embodiment, methods include orally administering to a subject an amount of a NASP in combination with a gastrointestinal epithelial barrier permeation enhancer and factor IX.

In other embodiments, the present invention provides a method of inhibiting TFPI activity in a subject. For example, methods may further include inhibiting TFPI activity in a subject by orally administering an amount of a NASP in combination with a gastrointestinal epithelial barrier permeation enhancer in a manner sufficient to inhibit TFPI activity in the subject. In certain instances, a procoagulant amount of a NASP and a gastrointestinal epithelial barrier permeation enhancer are combined with a biological sample (e.g., plasma) that includes TFPI and measuring the TFPI activity of the biological sample. In other instances, methods include combining a procoagulant amount of a NASP and a gastrointestinal epithelial barrier permeation enhancer with a biological sample, adding TFPI to the composition and measuring TFPI activity of the biological sample.

In certain embodiments, compositions of interest demonstrated enhanced permeation, for example, when determined by resorption studies in CaCo-2 cell models as compared to compositions in the absence of gastrointestinal epithelial permeation enhancers.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIGS. 5a-c show an example of resorption data acquired in the CaCo-2 bioavailability screening for fucoidan F.v. L/FVF-1091 in combination with gastrointestinal epithelial barrier permeation enhancers.

FIG. 9 show an example of resorption data acquired in the CaCo-2 bioavailability screening for synthetic NASP sulfated β-cyclodextrin in combination with gastrointestinal epithelial barrier permeation enhancers.

FIG. 10 show an example of resorption data acquired in the CaCo-2 bioavailability screening for synthetic NASP sulfated maltopentaose in combination with gastrointestinal epithelial barrier permeation enhancers.

RELEVANT DEFINITIONS

Figure 1:
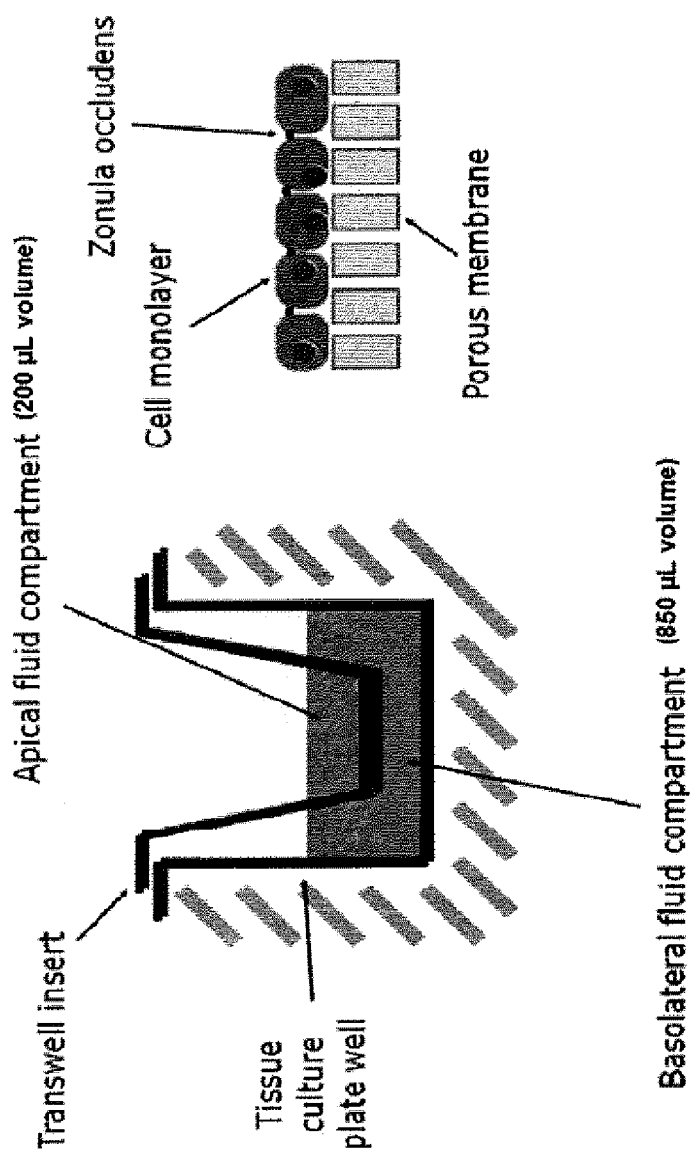
FIG. 1 shows the experimental setup for CaCo2 bioavailability screening to determine the % resorption of fucoidans.

In describing the present invention, the following terms will be employed, and are intended to be defined as indicated below.

It must be noted that, as used in this specification and the appended claims, the singular forms "a", "an" and "the" include plural referents unless the content clearly dictates otherwise. Thus, for example, reference to a "NASP" may include a mixture of two or more NASPs, as desired.

An "NASP" as used herein refers to sulfated polysaccharides (SP) that exhibit non-anticoagulant and anticoagulant activity in any of the various clotting assays described herein. NASPs may be natural sulfated polysaccharides, such as those extracted from a biological source or synthetic sulfated polysaccharides, where the sulfated polysaccharide is partially or wholly produced by synthetic methods (e.g., chemical synthesis). One measure of activity is to compare the clotting time demonstrated by a NASP with the anticoagulant activity displayed by heparin. For example, NASPs of interest exhibit anticoagulant activity in the dilute prothrombin time (dPT) or activated partial thromboplastin time (aPTT) clotting assay that is no more than one-third, such as less than one-tenth, the molar anticoagulant activity of unfractionated heparin (MW range 8,000 to 30,000; mean 18,000 daltons). As such, NASPs of interest demonstrate a 2-fold or more lower anticoagulant activity as compared to heparin, such as a 5-fold or more lower anticoagulant activity as compared to heparin, such as a 10-fold or more lower anticoagulant activate as compared to heparin, such as a 25-fold or more lower anticoagulant activity as compared to heparin, such as a 50-fold or more lower anticoagulant activity as compared to heparin, including a 100-fold or more lower anticoagulant activity as compared to heparin, by employing methods and compositions as provided herein.

NASPs of interest may range in molecular weight from 10 daltons to 1,000,000 daltons, such as for example, from 100 daltons to 900,000 daltons, such as from 500 daltons to 500,000 daltons, such as from 1000 daltons to 250,000 daltons, including 5000 daltons to 150,000 daltons. NASPs may range in average molecular weight from about 10 daltons to about 500,000 daltons, such as from about 100 daltons to about 300,000 daltons, such as from 1000 daltons to 250,000 daltons, including 1000 daltons to 150,000 daltons.

In some instances, NASPs of interest may include, but are not limited to N-acetyl-heparin (NAH), N-acetyl-de-O-sulfated-heparin (NA-de-o-SH), de-N-sulfated-heparin (De-NSH), de-N-sulfated-acetylated-he-parin (De-NSAH), periodate-oxidized heparin (POH), chemically sulfated laminarin (CSL), chemically sulfated alginic acid (CSAA), chemically sulfated pectin (CSP), dextran sulfate (DXS), heparin-derived oligosaccharides (HDO), pentosan polysulfate (PPS), sulfated maltopentoses, sulfated beta-cyclodextrins, sulfated 6-Carboxylcodextrin and derivatives thereof. In certain instances, the NASP is a fucoidan. For example, the fucoidan may be Fucoidan 5307002, *Fucus vesiculosus*, max. MW peak 126.7 kD; Fucoidan VG49, *Fucus vesiculosus*, hydrolyzed sample of 5307002 of lower MW, max. MW peak 22.5 kD; Fucoidan VG57, *Undaria pinnatifida*, high charge (high sulphation, deacetylated); Fucoidan GFS (5508005), *Undaria pinnatifida*, depyrogenated; Fucoidan GFS (L/FVF-01091), *Fucus vesiculosus*, depyrogenated, max. MW peak 125 kD; Fucoidan GFS (L/FVF-01092), *Fucus vesiculosus*, depyrogenated, max. MW peak 260 kD; Fucoidan GFS (L/FVF-01093), *Fucus vesiculosus*, hydrolyzed depyrogenated, max. MW peak 36 kD; Maritech® *Ecklonia radiata* extract; Maritech® *Ecklonia maxima* extract; Maritech® *Macrocystis pyrifera* extract; Maritech® Immune trial Fucoidan Blend; and combinations thereof.

NASPs in combination with a gastrointestinal epithelial barrier permeation enhancer may be used in the methods of the invention for improving hemostasis, in treating bleeding disorders, such as those associated with deficiencies of coagulation factors or for reversing the effects of anticoagulants, in particular when enhanced resorption by the gastrointestinal system is necessary or desired. The ability of NASPs to promote clotting and reduce bleeding may be determined using various in vitro clotting assays (e.g., TFPI-dPT, thrombin generation and thromboelastography (TEG) assays) and in vivo bleeding models (e.g. tail snip, transverse cut, whole blood clotting time, or cuticle bleeding time determination in hemophilic mice or dogs). See, e.g., PDR Staff. Physicians' Desk Reference. 2004, Anderson et al. (1976) Thromb. Res. 9:575-580; Nordfang et al. (1991) Thromb Haemost. 66:464-467; Welsch et al. (1991) Thrombosis Research 64:213-222; Broze et al. (2001) Thromb Haemost 85:747-748; Scallan et al. (2003) Blood. 102:2031-2037; Pijnappels et al. (1986) Thromb. Haemost. 55:70-73; and Giles et al. (1982) Blood 60:727-730, and the examples herein.

A "procoagulant" is used herein in its conventional sense to refer to any factor or reagent capable of initiating or accelerating clot formation. A procoagulant of the invention includes but is not limited to any activator of the intrinsic or extrinsic coagulation pathways, such as a clotting factor selected from the group consisting of factor Xa, factor IXa, factor XIa, factor XIIa, and VIIIa, prekallekrein, high-molecular weight kininogen, tissue factor, factor VIIa, and factor Va, as well as other reagents that promote clotting include kallikrein, APTT initiator (i.e., a reagent containing a phospholipid and a contact activator), Russel's viper venom (RVV time), and thromboplastin (for dPT). In some embodiments, contact activators may be employed as procoagulant reagents. For example, contact activators may include micronized silica particles, ellagic acid, sulfatides, kaolin or the like. Procoagulants may be from a crude natural extract, a blood or plasma sample, isolated and substantially purified, synthetic, or recombinant. Procoagulants may include naturally occurring clotting factors or fragments, variants or covalently modified derivatives thereof that retain biological activity (i.e., promote clotting).

The term "polysaccharide," as used herein, refers to a polymer containing two or more covalently linked saccharide residues. Saccharide residues may be linked for example by glycosidic, ester, amide, or oxime linking moieties. The average molecular weight of polysaccharides may vary widely, such as for example ranging from 100 to 1,000,000 daltons and more, such as 100 to 500,000 daltons and more, such as 1000 to 250,000 daltons and more, such as 1000 to 100,000 daltons and more, such as 10,000 to 50,000 daltons and more. Polysaccharides may be straight chained (i.e., linear) or branched or may contain discrete regions of linear and branched portions. Polysaccharides may also be fragments of polysaccharides generated by degradation (e.g., hydrolysis) of larger polysaccharides. Degradation can be achieved by any convenient protocol including treatment of polysaccharides with acid, base, heat, oxidants or enzymes to yield fragmented polysaccharides. Polysaccharides may be chemically altered and may be modified, including but not limited to, sulfation, polysulfation, esterification, and methylation.

Molecular weight, as discussed herein, can be expressed as either a number average molecular weight or a weight average molecular weight. Unless otherwise indicated, all references to molecular weight herein refer to the weight average molecular weight. Both molecular weight determinations, number average and weight average, can be measured using for example, gel permeation chromatography or other liquid chromatography techniques.

The term "derived from" is used herein to identify the original source of a molecule but is not meant to limit the method by which the molecule is made which can be, for example, by chemical synthesis or recombinant methodologies.

The terms "variant," "analog" and "mutein" refer to biologically active derivatives of a reference molecule, that retain desired activity, such as clotting activity in the treatment of a bleeding disorder. The terms "variant" and "analog" in reference to a polypeptide (e.g., clotting factor) refer to compounds having a native polypeptide sequence and structure with one or more amino acid additions, substitutions (generally conservative in nature) and/or deletions, relative to the native molecule, so long as the modifications do not destroy biological activity and which are "substantially homologous" to the reference molecule as defined below. The amino acid sequences of such analogs will have a high degree of sequence homology to the reference sequence, e.g., amino acid sequence homology of 50% or more, such as 60% or more, such as 70% or more, such as 80% or more, such as 90% or more, such as 95% or more, including 99% or more when the two sequences are aligned. In some instances, analogs will include the same number of amino acids but will include substitutions. The term "mutein" further includes polypeptides having one or more amino acid-like molecules including but not limited to compounds contain only amino and/or imino molecules, polypeptides containing one or more analogs of an amino acid (including, for example, synthetic non-naturally occurring amino acids, etc.), polypeptides with substituted linkages, as well as other modifications known in the art, both naturally occurring and non-naturally occurring (e.g., synthetic), cyclized, branched molecules and the like. The term also includes molecules comprising one or more N-substituted glycine residues (a "peptoid") and other synthetic amino acids or peptides. (See, e.g., U.S. Pat. Nos. 5,831,005; 5,877,278; and 5,977,301; Nguyen et al., Chem Biol. (2000) 7:463-473; and Simon et al., Proc. Natl. Acad. Sci. USA (1992) 89:9367-9371 for descriptions of peptoids). In embodiments of the invention, analogs and muteins have at least the same clotting activity as the native molecule.

As discussed above, analogs may include substitutions that are conservative, i.e., those substitutions that take place within a family of amino acids that are related in their side chains. Specifically, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are in some instances classified as aromatic amino acids. For example, an isolated replacement of leucine with isoleucine or valine, an aspartate with a glutamate, a threonine with a serine, or a similar conservative replacement of an amino acid with a structurally related amino acid, will not have a major effect on the biological activity. For example, the polypeptide of interest may include up to about 5-10 conservative or non-conservative amino acid substitutions, or even up to about 15-25 conservative or non-conservative amino acid substitutions, or any integer between 5-25, so long as the desired function of the molecule remains intact.

By "derivative" is meant any suitable modification of the reference molecule of interest or of an analog thereof, such as sulfation, acetylation, glycosylation, phosphorylation, polymer conjugation (such as with polyethylene glycol), or other addition of foreign moieties, so long as the desired biological activity (e.g., clotting activity, inhibition of TFPI activity) of the reference molecule is retained. For example, polysaccharides may be derivatized with one or more organic or inorganic groups. Examples include but are not limited to polysaccharides substituted in at least one hydroxyl group with another moiety (e.g., a sulfate, carboxyl, phosphate, amino, nitrile, halo, silyl, amido, acyl, aliphatic, aromatic, or a saccharide group), or where a ring oxygen has been replaced by sulfur, nitrogen, a methylene group, etc. Polysaccharides may be chemically altered, for example, to improve procoagulant function. Such modifications may include, but are not limited to, sulfation, polysulfation, esterification, and methylation.

By "fragment" is meant a molecule containing a part of the intact full-length sequence and structure. In some instances, a fragment of a polysaccharide may be generated by degradation (e.g., hydrolysis) of a larger polysaccharide. Active fragments of a polysaccharides of the invention may include about 2-20 saccharide units of the full-length polysaccharide, such as about 5-10 saccharide units of the full-length molecule, and including any integer between 2 saccharide units and the full-length molecule, so long as the fragment retains biological activity, such as for example, clotting activity or the ability to inhibit TFPI activity. A fragment of a polypeptide can include a C-terminal deletion, an N-terminal deletion, or an internal deletion of the native polypeptide. Active fragments of a particular protein may include, in some embodiments, about 5-10 contiguous amino acid residues of the full-length molecule or more, such as about 15-25 contiguous amino acid residues of the full-length molecule or more, such as about 20-50 contiguous amino acid residues of the full-length molecule or more, and including any integer between 5 amino acids and the full-length sequence, so long as the fragment in question retains biological activity, such as for example, clotting activity.

By "substantially purified" is meant the isolation of a substance (e.g., non-anticoagulant sulfated polysaccharide) such that the substance includes the majority of the sample in which it resides. For example, a sample that is substantially purified contains 50% or more of the substance of interest, such as 60% or more of the substance of interest, such as 75% or more of the substance of interest, such as 90% or more of the substance of interest, such as 95% or more of the substance of interest, including 99% or more of the substance of interest. Any convenient protocol may be employed for purifying polysaccharides, polynucleotides, and polypeptides of interest and include, but are not limited to ultrafiltration, selective precipitation, crystallization, ion-exchange chromatography, affinity chromatography and sedimentation according to density.

By "isolated" is meant, when referring to a polysaccharide or polypeptide, that the indicated molecule is separate and discrete from the whole organism with which the molecule is found in nature or is present in the substantial absence of other biological macro-molecules of the same type.

By "homology" is meant the percent identity between two polypeptide moieties. As referred to herein, two polypeptide sequences are "substantially homologous" to each other when the sequences exhibit about 50% or more sequence identity, such as 60% or more sequence identity, such as 75% or more sequence identity, such as 85% or more sequence identity, such as 90% or more sequence identity, such as 95% or more sequence identity, including 99% or more sequence identity. In some embodiments, substantially homologous polypeptides include sequences having complete identity to a specified sequence.

By "identity" is meant an exact subunit to subunit correspondence of two polymeric sequences. For example, an identical polypeptide is one that has an exact amino acid-to-amino acid correspondence to another polypeptide or an identical polynucleotide is one that has an exact nucleotide-to-nucleotide correspondence to another polynucleotide. Percent identity can be determined by a direct comparison of the sequence information between two molecules (the reference sequence and a sequence with unknown % identity to the reference sequence) by aligning the sequences, counting the exact number of matches between the two aligned sequences, dividing by the length of the reference sequence, and multiplying the result by 100. Any convenient protocol may be employed to determine percent identity between two polymeric sequences, such as for example, ALIGN, Dayhoff, M. O. in *Atlas of Protein Sequence and Structure* M. O. Dayhoff ed., 5 Suppl. 3:353-358, National biomedical Research Foundation, Washington, D.C., which adapts the local homology algorithm of Smith and Waterman *Advances in Appl. Math.* 2:482-489, 1981 for peptide analysis.

By "subject" is meant any member of the subphylum chordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are of interest.

The term "patient," is used in its conventional sense to refer to a living organism suffering from or prone to a condition that can be prevented or treated by administration of a NASP of the invention, and includes both humans and non-human animals.

By "biological sample" is meant a sample of tissue or fluid isolated from a subject, including but not limited to, for example, blood, plasma, serum, fecal matter, urine, bone marrow, bile, spinal fluid, lymph fluid, samples of the skin, external secretions of the skin, respiratory, intestinal, and genitourinary tracts, tears, saliva, milk, blood cells, organs, biopsies and also samples of in vitro cell culture constituents including but not limited to conditioned media resulting from the growth of cells and tissues in culture medium, e.g., recombinant cells, and cell components.

By "therapeutically effective dose or amount" is meant an amount that, when administered as described herein, brings about the desired therapeutic response, such as for example, reduced bleeding or shorter clotting times.

By "bleeding disorder" is meant any disorder associated with excessive bleeding, such as a congenital coagulation disorder, an acquired coagulation disorder, administration of an anticoagulant, or a trauma induced hemorrhagic condition. As discussed below, bleeding disorders may include, but are not limited to, hemophilia A, hemophilia B, von Willebrand disease, idiopathic thrombocytopenia, a deficiency of one or more contact factors, such as Factor XI, Factor XII, prekallikrein, and high molecular weight kininogen (HMWK), a deficiency of one or more factors associated with clinically significant bleeding, such as Factor V, Factor VII, Factor VIII, Factor IX, Factor X, Factor XIII, Factor II (hypoprothrombinemia), and von Willebrands factor, a vitamin K deficiency, a disorder of fibrinogen, including afibrinogenemia, hypofibrinogenemia, and dysfibrinogenemia, an $alpha_2$-antiplasmin deficiency, and excessive bleeding such as caused by liver disease, renal disease, thrombocytopenia, platelet dysfunction, hematomas, internal hemorrhage, hemarthroses, surgery, trauma, hypothermia, menstruation, and pregnancy.

DETAILED DESCRIPTION

Aspects of the invention include methods for enhancing blood coagulation in a subject. In practicing methods according to certain embodiments, an amount of a non-anticoagulant sulfated polysaccharide (NASP) in combination with a gastrointestinal epithelial barrier permeation enhancer is orally administered to a subject in a manner sufficient to enhance blood coagulation in the subject. Compositions and kits for practicing methods of the invention are also described.

Before the invention is described in greater detail, it is to be understood that the invention is not limited to particular embodiments described herein as such embodiments may vary. It is also to be understood that the terminology used herein is for the purpose of describing particular embodiments only, and the terminology is not intended to be limiting. The scope of the invention will be limited only by the appended claims. Unless defined otherwise, all technical and scientific terms used herein have the same meaning as commonly understood by one of ordinary skill in the art to which this invention belongs. Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention. Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number, which, in the context in which it is presented, provides the substantial equivalent of the specifically recited number. All publications, patents, and patent applications cited in this specification are incorporated herein by reference to the same extent as if each individual publication, patent, or patent application were specifically and individually indicated to be incorporated by reference. Furthermore, each cited publication, patent, or patent application is incorporated herein by reference to disclose and describe the subject matter in connection with which the publications are cited. The citation of any publication is for its disclosure prior to the filing date and should not be construed as an admission that the invention described herein is not entitled to antedate such publication by virtue of prior invention. Further, the dates of publication provided might be different from the actual publication dates, which may need to be independently confirmed.

It is noted that the claims may be drafted to exclude any optional element. As such, this statement is intended to serve as antecedent basis for use of such exclusive terminology as "solely," "only," and the like in connection with the recitation of claim elements, or use of a "negative" limitation. As will be apparent to those of skill in the art upon reading this disclosure, each of the individual embodiments described and illustrated herein has discrete components and features which may be readily separated from or combined with the features of any of the other several embodiments without departing from the scope or spirit of the invention. Any recited method may be carried out in the order of events recited or in any other order that is logically possible. Although any methods and materials similar or equivalent to those described herein may also be used in the practice or testing of the invention, representative illustrative methods and materials are now described.

In further describing the subject invention, methods for enhancing blood coagulation in a subject by orally administering a NASP in combination with a gastrointestinal epithelial barrier permeation enhancer are described first in greater detail. Next, compositions and kits for practicing methods of the subject invention are also described.

Methods for Enhancing Blood Coagulation in a Subject

As summarized above, aspects of the invention include methods for enhancing blood coagulation by orally administering a composition having an amount of a NASP in combination with a gastrointestinal epithelial permeation enhancer to a subject. The term "enhancing blood coagulation" is used in its conventional sense to refer to accelerating the initiation (i.e., reducing the amount time for coagulation to begin) of blood coagulation as well as the overall rate of blood coagulation of the subject (i.e., reducing the amount of time for blood coagulation to be complete). In some embodiments, methods of the invention accelerate the initiation of blood coagulation. For example, methods of the invention may reduce the amount of time required for the blood to begin coagulating by 5% or more, such as by 10% or more, such as by 25% or more, such as by 50% or more, such as by 75% or more, such as by 90% or more, such as 95% or more, as compared to a suitable control. In other embodiments, methods of the invention increase the rate of blood coagulation. For example, methods of the invention may increase the rate of blood coagulation by 2% or more, such as by 5% or more, such as by 10% or more, such as by 25% or more, such as by 50% or more, such as by 75% or more, such as by 100% or more, such as by 200% or more, including by 500% or more, as compared to a suitable control.

In embodiments of the present disclosure, a procoagulant amount of a NASP is orally administered in combination with a gastrointestinal epithelial barrier permeation enhancer.

Depending on the physiology of the subject, the phrase "gastrointestinal epithelial" as used herein, refers to the epithelial tissue of the digestive tract, such as the stomach and intestinal tract (e.g., duodenum, jejunum, ileum), and may further include other structures which participate in the gastrointestinal functions of the body including the lower part of the esophagus, the rectum and the anus. By gastrointestinal permeation enhancer is meant a compound that, when orally administered, increases the amount of NASP that is resorbed by the gastrointestinal system. Furthermore, gastrointestinal permeation enhancers may also accelerate the initiation (i.e., reducing the amount time for resorption to begin) of NASP resorption through the gastrointestinal epithelium as well as accelerate the overall rate of transport of the NASP across the gastrointestinal epithelium of the subject (i.e., reducing the amount of time for NASP resorption by the gastrointestinal system to be complete).

In some embodiments, gastrointestinal epithelial barrier permeation enhancers increase the amount of NASP resorbed by the gastrointestinal system. For example, gastrointestinal epithelial barrier permeation enhancers may increase the amount of NASP resorbed by the gastrointestinal system by 5% or more, such as by 10% or more, such as by 25% or more, such as by 50% or more, such as by 75% or more, such as by 90% or more, such as 95% or more, as compared to a suitable control. In other embodiments, gastrointestinal epithelial barrier permeation enhancers accelerate the initiation of NASP resorption through the gastrointestinal epithelium. For example, gastrointestinal epithelial barrier permeation enhancers of the invention may reduce the amount of time required to initiate resorption of the NASP by 5% or more, such as by 10% or more, such as by 25% or more, such as by 50% or more, such as by 75% or more, such as by 90% or more, such as 95% or more, as compared to a suitable control. In yet other embodiments, gastrointestinal epithelial barrier permeation enhancers of the invention increase the rate of resorption of the NASP by the gastrointestinal system. For example, gastrointestinal epithelial barrier permeation enhancers may increase the rate of NASP resorption by 2% or more, such as by 5% or more, such as by 10% or more, such as by 25% or more, such as by 50% or more, such as by 75% or more, such as by 100% or more, such as by 200% or more, including by 500% or more, as compared to a suitable control. In some instances, gastrointestinal epithelial permeation enhancers of the invention may increase the resorption of NASPs as determined by Caco-2 cell models, as described in greater detail below. For example, gastrointestinal epithelial barrier permeation enhancers of the invention may increase the resorption as determined by Caco-2 cell models by 2% or more, such as by 5% or more, such as by 10% or more, such as by 25% or more, such as by 50% or more, such as by 75% or more, such as by 100% or more, such as by 200% or more, including by 500% or more, as compared to a suitable control.

In embodiments of the invention, gastrointestinal epithelial barrier permeation enhancers may vary, depending on the particular blood coagulation disorder, the physiology of the subject and the desired enhancement of resorption by the gastrointestinal system. In some embodiments, gastrointestinal epithelial barrier permeation enhancers are tight junction modulators. The term "tight junction" is employed in it conventional sense to refer to the closely associated cellular areas where membranes of adjacent cells are joined together. As such, in certain embodiments, methods of the invention include orally administering a composition having a procoagulant amount of a NASP in combination with a compound which modulates the permeation of the NASP through the tight junctions of the gastrointestinal epithelium. By "modulates" is meant modifying or increasing the permeation of the NASP through the tight junctions of the gastrointestinal epithelium. As such, tight junction modulators modify or increase the resorption of NASPs by the gastrointestinal system. In embodiments of the invention, tight junction modulators may include, but are not limited to enzymes, bile acids, polysaccharides, fatty acids and salts thereof and any combination thereof.

In some instances, tight junction modulators are polysaccharides. For example, the polysaccharide tight junction modulator may be chitosan. Chitosan, as used herein refers to the linear copolymer of 2-acetamide-2-deoxy-β-D-glucopyranose and 2-amino-β-D-glucopyranose produced by the N-deacylation of chitin. Polysaccharide tight junction modulators may also include derivatives of chitosan such as N-alkyl chitosan, acylated chitosan, thiolated chitosan, phosphorylated chitosan, chitosan cyclodextrin, N-(aminoalkyl) chitosan, succinyl chitosan and octanoyl chitosan, among others.

In other instances, tight junction modulators are bile acids. The term "bile acid" is used in its conventional sense to refer to the steroidal acids and salts thereof commonly found in the bile of mammals. Suitable bile acids may include, but are not limited to, cholic acid (cholate), deoxycholic acid (deoxycholate), chenodeoxycholic acid (chenodeoxycholate), ursodeoxycholic acid (ursodeoxycholate), glycocholic acid (glycocholate), taurocholic acid (taurocholate) and lithocholic acid (lithocholate), among others.

In other instances, tight junction modulators are enzymes. For example, the enzyme tight junction modulators may be a protease, such as bromelain or an enzymatic fragment of bromelain. Bromelain, as used herein refers to the group of enzymes commonly derived from the fruit, stem and leaves of *Ananas comosus* and may also include elements such as cysteine proteases, amylase, acid phosphatase, peroxidases and cellulases.

In yet other instances, tight junction modulators are fatty acids and fatty acid salts thereof. Fatty acid tight junction modulators of the invention may vary, and may include any one or a combination of medium chain fatty acids, such as for example C8 (caprylate), C10 (caprate) and C12 (laurate) fatty acids and fatty acid salts thereof. In certain instances, for example, the fatty acid tight junction modulator is sodium caprate.

The concentration of gastrointestinal epithelial barrier permeation enhancer that is administered in combination with the NASP may vary depending on the effects as desired. Depending on the gastrointestinal epithelial barrier permeation enhancer, the concentration may be 0.01% or more of the total mass of the composition, such as 0.1% or more, such as 1% or more, such as 2% or more, such as 5% or more, such as 10% or more, such as 15% or more, such as 20% or more, such as 25% or more and including 50% or more of the total mass of the composition. In other embodiments, the concentration of the gastrointestinal epithelial barrier permeation enhancer that is administered in combination with the NASP is 0.01 mg/mL or more, such as 0.05 mg/mL or more, such as 0.1 mg/mL or more, such as 1 mg/mL or more and including 5 mg/mL or more. In yet other embodiments, the concentration of the gastrointestinal epithelial barrier permeation enhancer that is administered in combination with the NASP is 0.1 mM or more, such as 0.5 mM or more, such as 1 mM or more, such as 5 mM or more, such as 10 mM or more, such as 25 mM or more and including 50 mM or more. In certain embodiments, two or more gastrointestinal epithelial barrier permeation enhancers are employed concurrently. For example, two or more tight junction modulators may be employed in combination with a NASP, such as three or more tight junction modulators, including four or more tight junction modulators. Any combination of tight junction modulators may be employed, such as for example, a polysaccharide and a protease, a fatty acid and polysaccharide, a polysaccharide and a bile acid, a polysaccharide, a fatty acid and a bile acid, two different polysaccharides or two different bile acids, among other combinations. Where more than one gastrointestinal epithelial barrier permeation enhancer is employed, the mass percentage of each gastrointestinal epithelial barrier permeation enhancer may vary, ranging from 1% or more of the total mass of the composition, such as 2% or more, such as 5% or more, such as 10% or more, such as 25% or more and including 50% or more of the total mass of the composition. For example, where two gastrointestinal epithelial barrier permeation enhancers are employed, the mass ratio of the first gastrointestinal epithelial barrier permeation enhancer and the second gastrointestinal epithelial barrier permeation enhancer may vary, ranging between 1:1 and 1:2.5; 1:2.5 and 1:5; 1:5 and 1:10; 1:10 and 1:25; 1:25 and 1:50; 1:50 and 1:100; 1:100 and 1:150; 1:150 and 1:200; 1:200 and 1:250; 1:250 and 1:500; 1:500 and 1:1000, or a range thereof. For example, the mass ratio of the first gastrointestinal epithelial barrier permeation enhancer to the second gastrointestinal epithelial barrier permeation enhancer may range between 1:1 and 1:10; 1:5 and 1:25; 1:10 and 1:50; 1:25 and 1:100; 1:50 and 1:500; or 1:100 and 1:1000. In some embodiments, the mass ratio of the second gastrointestinal epithelial barrier permeation enhancer to the first gastrointestinal epithelial barrier permeation enhancer ranges between 1:1 and 1:2.5; 1:2.5 and 1:5; 1:5 and 1:10; 1:10 and 1:25; 1:25 and 1:50; 1:50 and 1:100; 1:100 and 1:150; 1:150 and 1:200; 1:200 and 1:250; 1:250 and 1:500; 1:500 and 1:1000, or a range thereof. For example, the mass ratio of the second gastrointestinal epithelial barrier permeation enhancer to the first gastrointestinal epithelial barrier permeation enhancer may range between 1:1 and 1:10; 1:5 and 1:25; 1:10 and 1:50; 1:25 and 1:100; 1:50 and 1:500; or 1:100 and 1:1000. In certain instances, the gastrointestinal epithelial barrier permeation enhancer includes a chitosan and a bromelain. Where a chitosan and a bromelain are employed, the mass ratio of the chitosan and the bromelain may vary, ranging between 1:1 and 1:2.5; 1:2.5 and 1:5; 1:5 and 1:10; 1:10 and 1:25; 1:25 and 1:50; 1:50 and 1:100; 1:100 and 1:150; 1:150 and 1:200; 1:200 and 1:250; 1:250 and 1:500; 1:500 and 1:1000, or a range thereof. For example, the mass ratio of the chitosan to the bromelain may range between 1:1 and 1:10; 1:5 and 1:25; 1:10 and 1:50; 1:25 and 1:100; 1:50 and 1:500; or 1:100 and 1:1000. In some embodiments, the mass ratio of the bromelain to the chitosan ranges between 1:1 and 1:2.5; 1:2.5 and 1:5; 1:5 and 1:10; 1:10 and 1:25; 1:25 and 1:50; 1:50 and 1:100; 1:100 and 1:150; 1:150 and 1:200; 1:200 and 1:250; 1:250 and 1:500; 1:500 and 1:1000, or a range thereof. For example, the mass ratio of the bromelain to the chitosan may range between 1:1 and 1:10; 1:5 and 1:25; 1:10 and 1:50; 1:25 and 1:100; 1:50 and 1:500; or 1:100 and 1:1000.

Where a combination of chitosan and bromelain are employed, in certain embodiments, the concentration of chitosan may vary, ranging from about 0.1% to about 5%, such as about 0.15% to about 4.5%, such as 0.2% to about 4%, such as about 0.25% to about 3.5%, such as 0.3% to about 3%, such as 0.5% to about 2.5%, including about 0.5% to 1.5%. Likewise, where a combination of chitosan and bromelain are employed, in certain embodiments, the concentration of bromelain may vary, ranging from about 0.01 mg/mL to about 1.0 mg/mL, such as about 0.2 mg/mL to about 0.9 mg/mL, such as 0.25 mg/mL to about 0.75 mg/mL, such as about 0.3 mg/mL to about 0.6 mg/mL, including about 0.4 mg/mL to about 0.5 mg/mL. As such, in these embodiments, methods include administering a NASP in combination with both chitosan and bromelain. For example, the NASP may be a natural or synthetic NASP, such as those described above, including N-acetyl-heparin (NAH), N-acetyl-de-O-sulfated-heparin (NA-de-o-SH), de-N-sulfated-heparin (De-NSH), de-N-sulfated-acetylated-heparin (De-NSAH), periodate-oxidized heparin (POH), chemically sulfated laminarin (CSL), chemically sulfated alginic acid (CSAA), chemically sulfated pectin (CSP), dextran sulfate (DXS), heparin-derived oligosaccharides (HDO), pentosan polysulfate (PPS), sulfated maltopentoses, sulfated beta-cyclodextrins, sulfated 6-Carboxylcodextrin and derivatives thereof. For instance, the NASP may be a fucoidan, such as Fucoidan 5307002, *Fucus vesiculosus*, max. MW peak 126.7 kD; Fucoidan VG49, *Fucus vesiculosus*, hydrolyzed sample of 5307002 of lower MW, max. MW peak 22.5 kD; Fucoidan VG57, *Undaria pinnatifida*, high charge (high sulphation, deacetylated); Fucoidan GFS (5508005), *Undaria pinnatifida*, depyrogenated; Fucoidan GFS (L/FVF-01091), *Fucus vesiculosus*, depyrogenated, max. MW peak 125 kD; Fucoidan GFS (L/FVF-01092), *Fucus vesiculosus*, depyrogenated, max. MW peak 260 kD; Fucoidan GFS (L/FVF-01093), *Fucus vesiculosus*, hydrolyzed depyrogenated, max. MW peak 36 kD; Maritech® *Ecklonia radiata* extract; Maritech® *Ecklonia maxima* extract; Maritech® *Macrocystis pyrifera* extract; Maritech® Immune trial Fucoidan Blend; and combinations thereof. As noted above, in certain instances the concentration of chitosan ranges from about 0.1% to about 5%, such as about 3% and the concentration of bromelain ranges from 0.1 mg/mL to about 1 mg/mL, such as about 0.5 mg/mL.

Where two or more gastrointestinal epithelial barrier permeation enhancers are employed, in some embodiments, the combination is a synergistically effective combination of gastrointestinal epithelial barrier permeation enhancers. The term "synergistically effective" is meant that the combination of gastrointestinal epithelial barrier permeation enhancers produces an effect (i.e., enhances gastrointestinal epithelial barrier permeation) which is greater than would be achieved by the sum of the individual gastrointestinal epithelial barrier permeation enhancers. For example, the combination of more than one gastrointestinal epithelial barrier permeation enhancer produces an effect that is 2-fold or greater than would be achieved by the sum of the individual gastrointestinal epithelial barrier permeation enhancers, such as 3-fold or greater, such as 4-fold or greater, such as 5-fold or greater, such as 10-fold or greater and including 25-fold or greater than would achieved with the sum the individual gastrointestinal epithelial barrier permeation enhancers. As such, where two gastrointestinal epithelial barrier permeation enhancers are combined, synergistically effective combinations of the present invention produce an effect which is 2-fold or greater, such as 5-fold or greater, such as 10-fold or greater and including 25-fold or greater than would be achieved by the sum of the two individual gastrointestinal epithelial barrier permeation enhancers. Likewise, where three gastrointestinal epithelial barrier permeation enhancers are combined, synergistically effective combinations of the present invention produce an effect which is 2-fold or greater, such as 5-fold or greater, such as 10-fold or greater and including 25-fold or greater than would be achieved by the sum of the three individual gastrointestinal epithelial barrier permeation enhancers. In certain embodiments, synergistically effective combinations of the present invention include a combination of chitosan and bromelain. In these embodiments, the combination of chitosan and bromelain has a greater effect on enhancing permeation through the gastrointestinal epithelial barrier than is achieved by the sum of chitosan and bromelain individually. For example, in some instances, the combination of chitosan and bromelain enhances permeation through the gastrointestinal epithelial barrier by 2-fold or greater, such as 5-fold or greater, such as 10-folder or greater and including 25-fold or greater than is achieved by the sum of chitosan and bromelain individually. In certain instances, synergistically effective combinations include a combination of bromelain having a concentration ranging from 0.1 mg/mL to about 0.5 mg/mL, such as 0.15 mg/mL to about 0.4 mg/mL, including 0.25 mg/mL and chitosan having a concentration ranging from about 1% to about 5% w/v, such as 1.5% to about 4.5% w/v, such as 2% to about 4% w/v and including about 3% w/v. In certain embodiments, synergistically effective combinations of bromelain and chitosan include a combination of 0.5 mg/mL bromelain and 3% w/v chitosan. In other embodiments, synergistically effective combinations of bromelain and chitosan include 0.25 mg/mL bromelain and 1.5% w/v chitosan. In yet other embodiments, synergistically effective combinations of bromelain and chitosan include 0.12 mg/mL bromelain and 0.75% w/v chitosan.

In embodiments of the invention, methods for enhancing blood coagulation by orally administering a NASP in combination with a gastrointestinal epithelial barrier permeation enhancer to a subject are provided. By "subject" is meant the person or organism receiving the blood coagulation enhancement. As such, subjects of the invention may include but are not limited to humans and other primates, such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like.

In some embodiments, the subject methods may be employed to treat bleeding disorders, such as a chronic or acute bleeding disorder, a congenital coagulation disorder caused by a blood factor deficiency, an acquired coagulation disorder and administration of an anticoagulant. For example, bleeding disorders may include, but are not limited to hemophilia A, hemophilia B, von Willebrand disease, idiopathic thrombocytopenia, a deficiency of one or more contact factors, such as Factor XI, Factor XII, prekallikrein, and high molecular weight kininogen (HMWK), a deficiency of one or more factors associated with clinically significant bleeding, such as Factor V, Factor VII, Factor VIII, Factor IX, Factor X, Factor XIII, Factor II (hypoprothrombinemia), and von Willebrands factor, a vitamin K deficiency, a disorder of fibrinogen, including afibrinogenemia, hypofibrinogenemia, and dysfibrinogenemia, an alpha$_2$-antiplasmin deficiency, and excessive bleeding such as caused by liver disease, renal disease, thrombocytopenia, platelet dysfunction, hematomas, internal hemorrhage, hemarthroses, surgery, trauma, hypothermia, menstruation, and pregnancy.

In other embodiments, the subject methods may be employed to enhance blood coagulation in order to reverse the effects of an anticoagulant in a subject. For example, the subject may have been treated with an anticoagulant including, but not limited to, heparin, a coumarin derivative, such as warfarin or dicumarol, TFPI, AT III, lupus anticoagulant, nematode anticoagulant peptide (NAPc2), active-site blocked factor VIIa (factor VIIai), factor IXa inhibitors, factor Xa inhibitors, including fondaparinux, idraparinux, DX-9065a, and razaxaban (DPC906), inhibitors of factors Va and VIIIa, including activated protein C (APC) and soluble thrombomodulin, thrombin inhibitors, including hirudin, bivalirudin, argatroban, and ximelagatran. In certain embodiments, the anticoagulant in the subject may be an antibody that binds a clotting factor, including but not limited to, an antibody that binds to Factor V, Factor VII, Factor VIII, Factor IX, Factor X, Factor XIII, Factor II, Factor XI, Factor XII, von Willebrands factor, prekallikrein, or high molecular weight kininogen (HMWK).

Aspects of the invention include orally administering to a subject a composition having an procoagulant amount of a NASP in combination with a gastrointestinal epithelial barrier permeation enhancer to enhance blood coagulation. As described above, NASPs of the invention may be natural NASPs or synthetic NASPs. In some embodiments, NASPs are natural NASPs. By "natural" is meant that the NASP is found or derived from a naturally occurring source, such as from an animal or plant source and encompass a broad range of subclasses including heparins, glycosaminoglycans, fucoidans, carrageenans, pentosan polysulfates, dermatan sulfates and dextran sulfates. In some embodiments, natural NASPs may be extracted from a biological source. By "biological source" is meant a naturally-occurring organism or part of an organism. For example, NASPs of interest may be extracted from plants, animals, fungi or bacteria. In particular, NASPs of interest may be extracted from edible seaweeds, brown algae, echinoderms (e.g., sea urchins, sea cucumbers) and the like. Any convenient protocol can be employed for extracting the NASP from the biological source. For instance, the NASP can be extracted from the biological source by acid-base extraction, enzymatic degradation, selective precipitation, filtration, among other procedures. Methods for extracting and isolating NASPs from biological sources such as edible seaweeds and brown algae are described in detail in co-pending U.S. patent application Ser. No. 12/449,712, filed Feb. 25, 2010, the disclosure of which is herein incorporated by reference, in its entirety.

In certain embodiments, natural NASPs of the invention include, but are not limited to N-acetyl-heparin (NAH), N-acetyl-de-O-sulfated-heparin (NA-de-o-SH), de-N-sulfated-heparin (De-NSH), de-N-sulfated-acetylated-he-parin (De-NSAH), periodate-oxidized heparin (POH), chemically sulfated laminarin (CSL), chemically sulfated alginic acid (CSAA), chemically sulfated pectin (CSP), dextran sulfate (DXS), heparin-derived oligosaccharides (HDO), pentosan polysulfate (PPS) and combinations thereof. In some instances, the NASP may be a low molecular weight fragment of a naturally occurring NASP. In other instances natural NASPs may also include biochemical or chemical derivatives of naturally occurring NASPs. In certain instances, natural NASPs are fucoidans. As described in greater detail below, fucoidans are naturally-occurring complex sulfated polysaccharides compounds which may be extracted from certain edible seaweeds, brown algae and echinoderms (e.g., sea urchins, sea cucumbers). As used herein the term, "fucoidan" refers to a diverse group of moieties extracted from a biological source of low sulfate polymers rather than a single chemical entity. In certain instances, fucoidans of the invention include, but are not limited to Fucoidan GFS 5508005, *Undaria pinnatifida*, depyrogenated; Fucoidan GFS 5508004, *Undaria pinnatifida*; Fucoidan GFS 5508003, *Undaria pinnatifida*; Fucoidan 5307002, *Fucus vesiculosus*, max. MW peak 126.7 kD; Fucoidan VG49, hydrolyzed sample of 5307002 of lower MW, max. MW peak 22.5 kD; Fucoidan 5308004, *Fucus vesiculosus*; Fucoidan 5308005, *Fucus vesiculosus*; Fucoidan L/FVF1091, *Fucus vesiculosus*; Fucoidan VG201096A, *Fucus vesiculosus*; Fucoidan VG201096B, *Fucus vesiculosus*; Fucoidan VG57, *Undaria pinnatifida*, high charge (high sulphation, deacetylated);

Fucoidan VG50, *Ascophyllum nodosum*, max. MW peak 149.7 kD; and combinations thereof.

Examples of suitable NASPs are described in greater detail in U.S. patent application Ser. No. 11/140,504, filed on May 27, 2005, now U.S. Pat. No. 7,767,654, and U.S. patent application Ser. No. 13/006,396, filed on Jan. 13, 2011, the disclosures of which is herein incorporated by reference in their entirety.

In other embodiments, NASPs are synthetic NASPs. By "synthetic" is meant that the sulfated polysaccharide is partially or wholly produced by man-made methods (e.g., chemical synthesis). For example, the synthetic NASP may be a sulfated oligomer, such as a sulfated oligosaccharide or a sulfated aliphatic. In certain instances, synthetic NASPs are sulfated pentoses, sulfated hexoses or sulfated cyclodextrins. For example, synthetic NASPs may include, but are not limited to sulfated maltopentoses, sulfated beta-cyclodextrins, sulfated 6-Carboxylcodextrin and derivatives thereof.

Examples of other suitable synthetic NASPs are described in greater detail in U.S. Provisional Patent Application Ser. No. 61/592,554, filed on Jan. 30, 2012 and U.S. Provisional Patent Application Ser. No. 61/592,549, filed on Jan. 30, 2012, the disclosures of which is herein incorporated by reference in their entirety.

Depending on the desired effects and potency of the NASPs, one or more NASPs may employed together. For example, two or more NASPs may be employed together, such as three or more NASPs and including four or more NASPs. Where more than one NASP is employed, all of the NASPs may be natural NASPs, all of the NASPs may be synthetic NASPs or any combination thereof. Where more than one NASP is employed, the mass percentage of each NASP in the composition may vary, ranging from 1% or more of the total mass of the composition, such as 2% or more, such as 5% or more, such as 10% or more, such as 25% or more and including as 50% or more of the total mass of the composition.

In embodiments of the invention, the mass ratio of the NASP and the gastrointestinal epithelial barrier permeation enhancer may vary, ranging between 1:1 and 1:2.5; 1:2.5 and 1:5; 1:5 and 1:10; 1:10 and 1:25; 1:25 and 1:50; 1:50 and 1:100; 1:100 and 1:150; 1:150 and 1:200; 1:200 and 1:250; 1:250 and 1:500; 1:500 and 1:1000, or a range thereof. For example, the mass ratio of the NASP to the gastrointestinal epithelial barrier permeation enhancer may range between 1:1 and 1:10; 1:5 and 1:25; 1:10 and 1:50; 1:25 and 1:100; 1:50 and 1:500; or 1:100 and 1:1000. In some embodiments, the mass ratio of the gastrointestinal epithelial barrier permeation enhancer to the NASP ranges between 1:1 and 1:2.5; 1:2.5 and 1:5; 1:5 and 1:10; 1:10 and 1:25; 1:25 and 1:50; 1:50 and 1:100; 1:100 and 1:150; 1:150 and 1:200; 1:200 and 1:250; 1:250 and 1:500; 1:500 and 1:1000, or a range thereof. For example, the mass ratio of the gastrointestinal epithelial barrier permeation enhancer to the NASP may range between 1:1 and 1:10; 1:5 and 1:25; 1:10 and 1:50; 1:25 and 1:100; 1:50 and 1:500; or 1:100 and 1:1000.

The NASP and the gastrointestinal epithelial barrier permeation enhancer may be administered to the subject in any order. In some instances, the NASP is orally administered prior to orally administering the gastrointestinal epithelial barrier permeation enhancer. In other instances, the NASP is orally administered after orally administering the gastrointestinal epithelial barrier permeation enhancer. In yet other instances, the NASP is orally administered in conjunction with orally administering the gastrointestinal epithelial barrier permeation enhancer. If both the NASP and the gastrointestinal epithelial barrier permeation enhancer are provided at the same time, each can be provided in the same or in a different composition. Where the NASP and the gastrointestinal epithelial barrier permeation enhancer are administered at the same time, the NASP may be mixed with the gastrointestinal epithelial barrier permeation enhancer the blood coagulation factor before administering the composition to the subject. Any convenient mixing protocol may be used, such as by dry shaking, solution or suspension mixing, industrial mixing protocols and the like. Thus, NASPs and gastrointestinal epithelial barrier permeation enhancers can be presented to the individual by way of concurrent therapy. By "concurrent therapy" is intended administration to a subject such that the therapeutic effect of the combination of the NASP and gastrointestinal epithelial barrier permeation enhancer is caused in the subject undergoing therapy. Similarly, one or more NASPs and one or more gastrointestinal epithelial barrier permeation enhancers can be orally administered in at least one therapeutic dose.

Any suitable combination of NASP and gastrointestinal epithelial barrier permeation enhancer may be administered. In certain embodiments, methods include administering a natural NASP (as described above) with one or more of gastrointestinal epithelial barrier permeation enhancers. In these embodiments, methods may include administering a combination of a natural NASP with one or more of sodium caprate, deoxycholate, bromelain and chitosan. In certain embodiments, methods include administering a natural NASP with sodium caprate. For instance, one or more of *Undaria pinnatifida* U.p. 5508005 and *Fucus vesiculosus* F.v. L/FVF 1091 may be administered with sodium caprate. In other embodiment, methods include administering a natural NASP with deoxycholate. For instance, one or more of *Undaria pinnatifida* U.p. 5508005, *Fucus vesiculosus* F.v. L/FVF 1091, *Fucus vesiculosus* F.v. DS1001108, *Fucus vesiculosus* F.v. SK110144B may be administered with deoxycholate. In yet other embodiments, methods include administering a natural NASP with bromelain. For instance, one or more of *Undaria pinnatifida* U.p. 5508005, *Fucus vesiculosus* F.v. L/FVF 1091, *Fucus vesiculosus* F.v. DS1001108, *Fucus vesiculosus* F.v. SK110144B may be administered with bromelain. In yet other embodiments, methods include administering a natural NASP with chitosan. For instance, one or more of *Undaria pinnatifida* U.p. 5508005, *Fucus vesiculosus* F.v. L/FVF 1091, *Fucus vesiculosus* F.v. DS1001108, *Fucus vesiculosus* F.v. SK110144B may be administered in combination with chitosan. In yet other embodiments, methods include administering a natural NASP with a combination of bromelain and chitosan (as described above). For instance, one or more of *Undaria pinnatifida* U.p. 5508005, *Fucus vesiculosus* F.v. L/FVF 1091, *Fucus vesiculosus* F.v. DS1001108, *Fucus vesiculosus* F.v. SK110144B may be administered with a combination of bromelain and chitosan.

In certain embodiments, methods include administering a synthetic NASP (as described above) with one or more of gastrointestinal epithelial barrier permeation enhancers. In these embodiments, methods may include administering a combination of a synthetic NASP with one or more of sodium caprate, deoxycholate, bromelain and chitosan. In certain embodiments, methods include administering a synthetic NASP with sodium caprate. For instance, one or more of a sulfated β-cyclodextrin and a sulfated maltopentose may be administered with sodium caprate. In other embodiment, methods include administering a synthetic NASP with deoxycholate. For instance, one or more of a 24 kD sulfated 6-carboxylcodextrin, a 14 kD 6-carboxylcodextrin, a sulfated β-cyclodextrin and a sulfated maltopentose may be administered with deoxycholate. In yet other embodiments, methods include administering a synthetic NASP with bromelain. For instance, one or more of a 24 kD sulfated 6-carboxylcodextrin, a 14 kD 6-carboxylcodextrin, a sulfated β-cyclodextrin and a sulfated maltopentose may be administered with bromelain. In yet other embodiments, methods include administering a synthetic NASP with chitosan. For instance, one or more of a 24 kD sulfated 6-carboxylcodextrin, a 14 kD 6-carboxylcodextrin, a sulfated β-cyclodextrin and a sulfated maltopentose may be administered in combination with chitosan. In yet other embodiments, methods include administering a synthetic NASP with a combination of bromelain and chitosan (as described above). For instance, one or more of a 24 kD sulfated 6-carboxylcodextrin, a 14 kD 6-carboxylcodextrin, a sulfated β-cyclodextrin and a sulfated maltopentose may be administered with a combination of bromelain and chitosan.

In certain embodiments, aspects of the invention include enhancing blood coagulation in a subject by orally administering to the subject, a composition that contains a procoagulant amount of a NASP and a gastrointestinal epithelial barrier permeation enhancer in combination with a blood coagulation factor. For example, the subject may be orally administered a procoagulant amount of a composition containing a NASP and a gastrointestinal epithelial barrier permeation enhancer in combination with one or more blood coagulation factors which include, but are not limited to factor XI, factor XII, prekallikrein, high molecular weight kininogen (HMWK), factor V, factor VII, factor VIII, factor IX, factor X, factor XIII, factor II, factor VIIa, and von Willebrands factor, factor Xa, factor IXa, factor XIa, factor XIIa, and VIIIa, prekallekrein, and high-molecular weight kininogen, tissue factor, factor VIIa, factor Va, and factor Xa.

Where a composition that contains a NASP and a gastrointestinal epithelial barrier permeation enhancer is orally administered with a blood coagulation factor to the subject, the mass ratio of the composition that contains the NASP and gastrointestinal epithelial barrier permeation enhancer to the blood coagulation factor may vary, ranging between 1:1 and 1:2.5; 1:2.5 and 1:5; 1:5 and 1:10; 1:10 and 1:25; 1:25 and 1:50; 1:50 and 1:100; 1:100 and 1:150; 1:150 and 1:200; 1:200 and 1:250; 1:250 and 1:500; 1:500 and 1:1000, or a range thereof. For example, the mass ratio of the composition that contains the NASP and gastrointestinal epithelial barrier permeation enhancer to the blood coagulation factor may range between 1:1 and 1:10; 1:5 and 1:25; 1:10 and 1:50; 1:25 and 1:100; 1:50 and 1:500; or 1:100 and 1:1000. In some embodiments, the mass ratio of the blood coagulation factor to the composition that contains the NASP and gastrointestinal epithelial barrier permeation enhancer ranges between 1:1 and 1:2.5; 1:2.5 and 1:5; 1:5 and 1:10; 1:10 and 1:25; 1:25 and 1:50; 1:50 and 1:100; 1:100 and 1:150; 1:150 and 1:200; 1:200 and 1:250; 1:250 and 1:500; 1:500 and 1:1000, or a range thereof. For example, the mass ratio of the blood coagulation factor to the composition that contains the NASP and gastrointestinal epithelial barrier permeation enhancer may range between 1:1 and 1:10; 1:5 and 1:25; 1:10 and 1:50; 1:25 and 1:100; 1:50 and 1:500; or 1:100 and 1:1000.

The blood coagulation factor and the composition that contains the NASP and gastrointestinal epithelial barrier permeation enhancer may be administered to the subject in any order. In some instances, the composition that contains the NASP and gastrointestinal epithelial barrier permeation enhancer is orally administered prior to administering the blood coagulation factor. In other instances, the composition that contains the NASP and gastrointestinal epithelial barrier permeation enhancer is orally administered in conjunction with administering the blood coagulation factor. In yet other instances, the composition that contains the NASP and gastrointestinal epithelial barrier permeation enhancer is orally administered after administering the blood coagulation factor. Where the composition that contains the NASP and gastrointestinal epithelial barrier permeation enhancer is orally administered in conjunction with the blood coagulation factor, the composition that contains the NASP and gastrointestinal epithelial barrier permeation enhancer may be mixed with the blood coagulation factor before orally administering the composition to the subject. Any convenient mixing protocol may be used, such as a by dry shaking, solution or suspension mixing, industrial mixing protocols and the like.

Aspects of the invention include methods and compositions for treating bleeding disorders by orally administering a procoagulant amount of a NASP in combination with a gastrointestinal epithelial barrier permeation enhancer. NASPs in combination with a gastrointestinal epithelial barrier permeation enhancer as disclosed herein can be administered alone (i.e., as single agents), or in combination with other hemostatic agents. As desired, a procoagulant amount of a NASP in combination with a gastrointestinal epithelial barrier permeation enhancer may be employed in the treatment of a subject that has been diagnosed as having a bleeding disorder, including congenital coagulation disorders, acquired coagulation disorders, administration of an anticoagulant, and trauma induced hemorrhagic conditions.

In some instances, a subject may be diagnosed as having a blood clotting disorders that includes, but is not limited to hemophilia A, hemophilia B, von Willebrand disease, idiopathic thrombocytopenia, a deficiency of one or more contact factors, such as Factor XI, Factor XII, prekallikrein, and high molecular weight kininogen (HMWK), a deficiency of one or more factors associated with clinically significant bleeding, such as Factor V, Factor VII, Factor VIII, Factor IX, Factor X, Factor XIII, Factor II (hypoprothrombinemia), and von Willebrands factor, a vitamin K deficiency, a disorder of fibrinogen, including afibrinogenemia, hypofibrinogenemia, and dysfibrinogenemia, an alpha$_2$-antiplasmin deficiency, and excessive bleeding such as caused by liver disease, renal disease, thrombocytopenia, platelet dysfunction, hematomas, internal hemorrhage, hemarthroses, surgery, trauma, hypothermia, menstruation, and pregnancy.

In other instances, a subject may be diagnosed as having a blood clotting disorder that includes a congenital coagulation disorder or an acquired coagulation disorder caused by a blood factor deficiency. For example, the blood factor deficiency may be caused by deficiencies of one or more factors, including but not limited to, factor V, factor VII, factor VIII, factor IX, factor XI, factor XII, factor XIII, and von Willebrand factor.

In yet other instances, a subject may be diagnosed as having a blood clotting disorder resulting from the administration of an anticoagulant to the subject. For example, the anticoagulant may include but is not limited to, heparin, a coumarin derivative, such as warfarin or dicumarol, tissue factor pathway inhibitor (TFPI), antithrombin III, lupus anticoagulant, nematode anticoagulant peptide (NAPc2), active-site blocked factor VIIa (factor VIIai), factor IXa inhibitors, factor Xa inhibitors, including fondaparinux, idraparinux, DX-9065a, and razaxaban (DPC906), inhibitors of factors Va and VIIIa, including activated protein C (APC) and soluble thrombomodulin, thrombin inhibitors, including hirudin, bivalirudin, argatroban, and ximelagatran. In certain embodiments, the anticoagulant may be an antibody that binds a clotting factor, including but not limited to, an antibody that binds to Factor V, Factor VII, Factor VIII, Factor IX, Factor X, Factor XIII, Factor II, Factor XI, Factor XII, von Willebrands factor, prekallikrein, or high molecular weight kininogen (HMWK).

In yet other instances, methods of the invention include a method of inhibiting TFPI activity in a subject. For example, methods may further include orally administering to a subject, an amount of a NASP in combination with a gastrointestinal epithelial barrier permeation enhancer in a manner sufficient to inhibit TFPI activity in the subject. In certain instances, a procoagulant amount of a NASP in combination with a gastrointestinal epithelial barrier permeation enhancer is combined with a biological sample (e.g., blood plasma) that includes TFPI and measuring the TFPI activity of the biological sample. In other instances, methods include combining a procoagulant amount of a NASP and a gastrointestinal epithelial barrier permeation enhancer with a biological sample, adding TFPI to the composition and measuring the TFPI activity of the biological sample. In certain instances, the biological sample is a plasma sample, such as for example, normal blood plasma or Factor VIII-inhibited blood plasma.

In practicing methods of the invention, protocols for enhancing blood coagulation in a subject may vary, such as for example by age, weight, severity of the blood clotting disorder, the general health of the subject, as well as the particular composition and concentration of the NASPs and gastrointestinal epithelial barrier permeation enhancers being administered. In embodiments of the invention, the concentration of NASPs achieved in a subject following oral administration and resorption by the gastrointestinal system may vary, in some instances, ranging from 0.01 nM to 500 nM. NASPs of interest are procoagulant at their optimal concentration. By "optimal concentration" is meant the concentration in which NASPs exhibit the highest amount of procoagulant activity. Since many of the NASPs also demonstrated anticoagulant activity at much higher concentrations than the optimal concentration, NASPs of the invention show non-anticoagulant behavior in the range of its optimal concentration. As such, depending on the potency of the NASP as well as the desired effect, the optimal concentration of NASPs provided by methods of the invention may range, from 0.01 nM to 500 nM, such as 0.1 nM to 250 nM, such as 0.1 nM to 100 nM, such as 0.1 nM to 75 nM, such as 0.1 nM to 50 nM, such as 0.1 nM to 25 nM, such as 0.1 nM to 10 nM, and including 0.1 nM to 1 nM. Optimal concentrations and activity level as determined by calibrated automated thrombography (CAT) assay of NASPs of interest are described in greater detail in U.S. patent application Ser. No. 11/140,504, filed on May 27, 2005, now U.S. Pat. No. 7,767,654, and U.S. patent application Ser. No. 13/006,396, filed on Jan. 13, 2011, the disclosures of which is herein incorporated by reference in their entirety. Likewise, the concentration of gastrointestinal epithelial barrier permeation enhancers achieved in a subject following oral administration and resorption by the gastrointestinal system may vary, in some instances, ranging from 0.01 nM to 500 nM. For example, depending on the inherent absorptivity of the NASP as well as the desired effect, the concentration of gastrointestinal epithelial barrier permeation enhancers provided by methods of the invention may range, from 0.01 nM to 500 nM, such as 0.1 nM to 250 nM, such as 0.1 nM to 100 nM, such as 0.1 nM to 75 nM, such as 0.1 nM to 50 nM, such as 0.1 nM to 25 nM, such as 0.1 nM to 10 nM, and including 0.1 nM to 1 nM.

Therefore, the oral dosage of compositions containing NASPs in combination with gastrointestinal epithelial barrier permeation enhancers of interest may vary, ranging from about 0.01 mg/kg to 500 mg/kg per day, such as from 0.01 mg/kg to 400 mg/kg per day, such as 0.01 mg/kg to 200 mg/kg per day, such as 0.1 mg/kg to 100 mg/kg per day, such as 0.01 mg/kg to 10 mg/kg per day, such as 0.01 mg/kg to 2 mg/kg per day, including 0.02 mg/kg to 2 mg/kg per day. In other embodiments, the oral dosage may range from 0.01 to 100 mg/kg four times per day (QID), such as 0.01 to 50 mg/kg QID, such as 0.01 mg/kg to 10 mg/kg QID, such as 0.01 mg/kg to 2 mg/kg QID, such as 0.01 mg/kg to 0.2 mg/kg QID. In other embodiments, the oral dosage may range from 0.01 mg/kg to 50 mg/kg three times per day (TID), such as 0.01 mg/kg to 10 mg/kg TID, such as 0.01 mg/kg to 2 mg/kg TID, and including as 0.01 mg/kg to 0.2 mg/kg TID. In yet other embodiments, the oral dosage may range from 0.01 mg/kg to 100 mg/kg two times per day (BID), such as 0.01 mg/kg to 10 mg/kg BID, such as 0.01 mg/kg to 2 mg/kg BID, including 0.01 mg/kg to 0.2 mg/kg BID. The amount of compound administered will depend on the potency and concentration of the specific NASP, the magnitude or procoagulant effect desired, the inherent absorptivity of the NASP, as well as the desired enhancement of gastrointestinal resorption.

As discussed above, compositions containing a NASP in combination with a gastrointestinal epithelial barrier permeation enhancer as provided by methods of the invention may be orally administered in combination with other NASPs, gastrointestinal epithelial barrier permeation enhancers or other therapeutic agents, such as hemostatic agents, blood factors, or other medications according to a dosing schedule relying on the judgment of the clinician and needs of the subject. As such, dosing schedules may include, but is not limited to administration five times per day, four times per day, three times per day, twice per day, once per day, three times per week, twice per week, once per week, twice per month, once per month, and any combination thereof.

In some embodiments, the bleeding disorder may be a chronic condition (e.g., a congenital or acquired coagulation factor deficiency) requiring the subject methods and compositions in multiple doses over an extended period. Alternatively, methods and compositions of the invention may be administered to treat an acute condition (e.g., bleeding caused by surgery or trauma, or factor inhibitor/autoimmune episodes in subjects receiving coagulation replacement therapy) in single or multiple doses for a relatively short period, for example one to two weeks.

In practicing embodiments of the invention, one or more therapeutically effective cycles of treatment will be administered to a subject. By "therapeutically effective cycle of treatment" is meant a cycle of treatment that when administered, brings about the desired therapeutic response with respect to treatment. For example, one or more therapeutically effective cycles of treatment may increase the rate of blood clotting as determined by blood clotting assays (e.g., CAT, aPTT, described in detail below) by 1% or more, such as 5% or more, such as 10% or more, such as 15% or more, such as 20% or more, such as 30% or more, such as 40% or more, such as 50% or more, such as 75% or more, such as 90% or more, such as 95% or more, including increasing the rate of blood clot formation by 99% or more. In other instances, one or more therapeutically effective cycles of treatment may increase the rate of blood clot formation by 1.5-fold or more, such as 2-fold or more, such as 5-fold or more, such as 10-fold or more, such as 50-fold or more, including increasing the rate of blood clot formation by 100-fold or more. In some embodiments, subjects treated by methods of the invention exhibit a positive therapeutic response. By "positive therapeutic response" is meant that the subject exhibits an improvement in one or more symptoms of a bleeding disorder. For example, a subject exhibiting a positive therapeutic response to methods provided by the invention may include but is not limited to responses such as shortened blood clotting times, reduced bleeding, reduced need for factor replacement therapy or a combination thereof. In certain embodiments, more than one therapeutically effective cycle of treatment is administered.

As reviewed above, in practicing methods according to certain embodiments, a composition having a procoagulant amount of a NASP in combination with a gastrointestinal epithelial barrier permeation enhancer is administered to a subject to enhance blood coagulation in the subject. Any convenient mode of administration may be employed so long as the composition is resorbed through the gastrointestinal epithelium. As such, modes of administration may include oral administration or by nasogastric tube (e.g., feeding tube or NG-tube). As discussed in greater detail below, pharmaceutical compositions of the invention may be in the form of a liquid solution or suspension, syrup, tablet, capsule, powder, gel, or any combination thereof. Where a composition having a procoagulant amount of a NASP and gastrointestinal epithelial barrier permeation enhancer is orally administered in combination with a blood coagulation factor, as discussed in detail above, the mode of administration for the NASP and gastrointestinal epithelial barrier permeation enhancer component may be the same or different than for the blood coagulation factor. For example, in some instances, the composition having a procoagulant amount of a NASP and gastrointestinal epithelial barrier permeation enhancer may be administered orally, whereas the blood coagulation factor may be locally applied (e.g., as a cream). In other instances, both the composition having a procoagulant amount of a NASP gastrointestinal epithelial barrier permeation enhancer and the blood coagulation factor are administered orally.

In certain embodiments, methods of the invention provide for orally administering a composition having a procoagulant amount of a NASP and gastrointestinal epithelial barrier permeation enhancer prophylactically, such as for example before planned surgery. The composition may be administered prophylactically as desired, such as one hour or more prior to a planned procedure, such as 10 hours prior to a planned procedure, such as 24 hours prior to a planned procedure, and including one week prior to a planned procedure. In some instances, the composition administered prior to or during a planned procedure may be a sustained-release formulation (e.g., sustained release caplets or tablets), as described in greater detail below.

In certain embodiments, compositions of the invention can be orally administered prior to, concurrent with, or subsequent to other agents for treating related or unrelated conditions. If provided at the same time as other agents, compositions of the invention can be provided in the same or in a different composition. Thus, NASPs and gastrointestinal epithelial barrier permeation enhancers of interest and other agents can be presented in an oral dosage form to the individual by way of concurrent therapy. For example, concurrent therapy may be achieved by administering compositions of the invention and a pharmaceutical composition having at least one other agent, such as a hemostatic agent or coagulation factor (e.g. FVIII or FIX), which in combination comprise a therapeutically effective dose, according to a particular oral dosing regimen. Similarly, one or more NASPs in combination with one or more gastrointestinal epithelial barrier permeation enhancers and therapeutic agents can be administered in at least one therapeutic dose. Administration of the separate pharmaceutical compositions can be performed simultaneously or at different times (i.e., sequentially, in either order, on the same day, or on different days), so long as the therapeutic effect of the combination of these substances is caused in the subject undergoing therapy.

Compositions

Aspects of the invention also include oral dosage compositions for enhancing blood coagulation in a subject. In embodiments of the invention, compositions include a procoagulant amount of a NASP in combination with a gastrointestinal epithelial barrier permeation enhancer. Compositions also include a combination of a procoagulant amount of a NASP with a gastrointestinal epithelial barrier permeation enhancer and a blood coagulation factor. As described in detail above, gastrointestinal epithelial barrier permeation enhancers include compounds that when orally administered, increase the amount of NASP that is resorbed by the gastrointestinal system. Furthermore, gastrointestinal permeation enhancers may also accelerate the initiation (i.e., reducing the amount time for resorption to begin) of NASP resorption through the gastrointestinal epithelium as well as accelerate the overall rate of transport of the NASP across the gastrointestinal epithelium of the subject (i.e., reducing the amount of time for NASP resorption by the gastrointestinal system to be complete).

As noted above, gastrointestinal epithelial barrier permeation enhancers may increase the amount of NASP resorbed by the gastrointestinal system. For example, gastrointestinal epithelial barrier permeation enhancers may increase the amount of NASP resorbed by the gastrointestinal system by 5% or more, such as by 10% or more, such as by 25% or more, such as by 50% or more, such as by 75% or more, such as by 90% or more, such as 95% or more, as compared to a suitable control. In other embodiments, gastrointestinal epithelial barrier permeation enhancers in oral compositions of the invention accelerate the initiation of NASP resorption through the gastrointestinal epithelium. For example, gastrointestinal epithelial barrier permeation enhancers of the invention may reduce the amount of time required to initiate resorption of the NASP by 5% or more, such as by 10% or more, such as by 25% or more, such as by 50% or more, such as by 75% or more, such as by 90% or more, such as 95% or more, as compared to a suitable control. In yet other embodiments, gastrointestinal epithelial barrier permeation enhancers in oral compositions of the invention increase the rate of resorption of the NASP. For example, gastrointestinal epithelial barrier permeation enhancers may increase the rate of NASP resorption by 2% or more, such as by 5% or more, such as by 10% or more, such as by 25% or more, such as by 50% or more, such as by 75% or more, such as by 100% or more, such as by 200% or more, including by 500% or more, as compared to a suitable control.

In certain instances, gastrointestinal epithelial permeation enhancers in oral compositions of the invention may increase the resorption of NASPs as determined by Caco-2 cell models. For example, gastrointestinal epithelial barrier permeation enhancers of the invention may increase the resorption as determined by Caco-2 cell models by 2% or more, such as by 5% or more, such as by 10% or more, such as by 25% or more, such as by 50% or more, such as by 75% or more, such as by 100% or more, such as by 200% or more, including by 500% or more, as compared to a suitable control.

As discussed in detail above, oral dosage compositions of the invention include one or more NASPs in combination with one or more gastrointestinal epithelial barrier permeation enhancers. Gastrointestinal epithelial barrier permeation enhancers in the compositions of interest may vary. In some embodiments, gastrointestinal epithelial barrier permeation enhancers are tight junction modulators. For example, tight junction modulators in oral dosage compositions of the invention may include, but are not limited to enzymes, bile acids, polysaccharides, fatty acids and salts thereof and any combination thereof.

In some instances, tight junction modulators are polysaccharides. For example, the polysaccharide tight junction modulator, in certain instances may be chitosan. Chitosan, as discussed above, refers to the linear copolymer of 2-acetamide-2-deoxy-β-D-glucopyranose and 2-amino-β-D-glucopyranose made by N-deacylation of chitin. Polysaccharide tight junction modulators may also include, derivatives of chitosan such as N-alkyl chitosan, acylated chitosan, thiolated chitosan, phosphorylated chitosan, chitosan cyclodextrin, N-(aminoalkyl)chitosan, succinyl chitosan and octanoyl chitosan, among others.

In other instances, tight junction modulators are bile acids. Suitable bile acid tight junction modulators may include but are not limited to cholic acid (cholate), deoxycholic acid (deoxycholate), chenodeoxycholic acid (chenodeoxycholate), ursodeoxycholic acid (ursodeoxycholate), glycocholic acid (glycocholate), taurocholic acid (taurocholate) and lithocholic acid (lithocholate), among others.

In other instances, tight junction modulators are enzymes. For example, in certain compositions of the invention, the enzyme tight junction modulators is a protease, such as bromelain.

In yet other instances, tight junction modulators are fatty acids and fatty acid salts thereof. Fatty acid tight junction modulators in compositions of the invention may vary, and may include any one or a combination of medium chain fatty acids, such as for example C8 (caprylate), C10 (caprate) and C12 (laurate) fatty acids and fatty acid salts thereof. In certain instances, for example, the fatty acid tight junction modulator is sodium caprate.

In certain embodiments, oral dosage compositions of the invention include two or more gastrointestinal epithelial barrier permeation enhancers. For example, compositions may include two or more tight junction modulators, such as three or more tight junction modulators, including four or more tight junction modulators. Compositions may include any combination of tight junction modulators, such as for example, a polysaccharide and a protease, a fatty acid and polysaccharide, a polysaccharide and a bile acid, a polysaccharide, a fatty acid and a bile acid, two different polysaccharides or two different bile acids, among other combinations. Where compositions include more than one gastrointestinal epithelial barrier permeation enhancer, the mass percentage of each gastrointestinal epithelial barrier permeation enhancer may vary, ranging from 1% or more of the total mass of the composition, such as 2% or more, such as 5% or more, such as 10% or more, such as 25% or more and including 50% or more of the total mass of the composition.

In certain instances, compositions of the invention include chitosan and bromelain. Where the composition includes a combination of chitosan and bromelain, the mass ratio of chitosan and bromelain may vary, ranging between 1:1 and 1:2.5; 1:2.5 and 1:5; 1:5 and 1:10; 1:10 and 1:25; 1:25 and 1:50; 1:50 and 1:100; 1:100 and 1:150; 1:150 and 1:200; 1:200 and 1:250; 1:250 and 1:500; 1:500 and 1:1000, or a range thereof. For example, the mass ratio of chitosan to bromelain may range between 1:1 and 1:10; 1:5 and 1:25; 1:10 and 1:50; 1:25 and 1:100; 1:50 and 1:500; or 1:100 and 1:1000. In some embodiments, the mass ratio of bromelain to chitosan ranges between 1:1 and 1:2.5; 1:2.5 and 1:5; 1:5 and 1:10; 1:10 and 1:25; 1:25 and 1:50; 1:50 and 1:100; 1:100 and 1:150; 1:150 and 1:200; 1:200 and 1:250; 1:250 and 1:500; 1:500 and 1:1000, or a range thereof. For example, the mass ratio of bromelain to chitosan may range between 1:1 and 1:10; 1:5 and 1:25; 1:10 and 1:50; 1:25 and 1:100; 1:50 and 1:500; or 1:100 and 1:1000.

Where compositions of the invention include a combination of chitosan and bromelain, the concentration of chitosan may also vary, ranging from about 0.1% to about 5%, such as about 0.15% to about 4.5%, such as 0.2% to about 4%, such as about 0.25% to about 3.5%, such as 0.3% to about 3%, such as 0.5% to about 2.5%, including about 0.5% to 1.5%. Likewise, where a combination of chitosan and bromelain are employed, in certain embodiments, the concentration of bromelain may also vary, ranging from about 0.01 mg/mL to about 1.0 mg/mL, such as about 0.2 mg/mL to about 0.9 mg/mL, such as 0.25 mg/mL to about 0.75 mg/mL, such as about 0.3 mg/mL to about 0.6 mg/mL, including about 0.4 mg/mL to about 0.5 mg/mL. In certain instances, the concentration of chitosan is about 3% and the concentration of bromelain is about 0.5 mg/mL.

As described above, NASPs in oral dosage compositions of the invention are sulfated polysaccharides that demonstrate procoagulant activity. The non-anticoagulant properties of NASPs may be determined using clotting assays, including calibrated automated thrombography (CAT) in Factor VIII and/or Factor IX deficient plasma, dilute prothrombin time (dPT) or activated partial thromboplastin time (aPTT) clotting assays. One measure of noncoagulant activity is to compare the NASP in question with the known anticoagulant heparin. For example, NASPs may exhibit one-third or less, such as one-tenth or less of the anticoagulant activity (measured by statistically significant increase in clotting time) of unfractionated heparin (MW range 8,000 to 30,000; mean 18,000 Daltons). Thus, a NASP can demonstrate at least a two-fold lower anticoagulant activity as compared to heparin, such as a two- to five-fold or lower anticoagulant activity as compared to heparin, and including a two- to 10-fold or lower anticoagulant activity as compared to heparin, using any of the various clotting assays detailed herein.

In some embodiments, oral dosage compositions of the invention include a natural NASP in combination with a gastrointestinal epithelial barrier permeation enhancer. As discussed above, natural NASPs may be NASPs found or derived from a naturally occurring source, such as from an animal or plant source and may encompass a broad range of subclasses including derivatives of heparins, glycosaminoglycans, fucoidans, carrageenans, pentosan polysulfates, dermatan sulfates and dextran sulfates. In some embodiments, natural NASPs of the invention are extracted from a biological source. By "biological source" is meant a naturally-occurring organism or part of an organism. For example, NASPs of interest may be extracted from plants, animals, fungi or bacteria. In particular, NASPs of interest may be extracted from edible seaweeds, brown algae, echinoderms (e.g., sea urchins, sea cucumbers) and the like. For instance, the NASP can be extracted from the biological source by acid-base extraction, enzymatic degradation, selective precipitation, filtration, among other procedures. Natural NASPs such as those extracted from biological sources, including but not limited to edible seaweeds and brown algae are described in detail in co-pending U.S. patent application Ser. No. 12/449,712, filed Feb. 25, 2010, the disclosure of which is herein incorporated by reference, in its entirety.

In certain embodiments, natural NASPs of the invention include, but are not limited to N-acetyl-heparin (NAH), N-acetyl-de-O-sulfated-heparin (NA-de-o-SH), de-N-sulfated-heparin (De-NSH), de-N-sulfated-acetylated-heparin (De-NSAH), periodate-oxidized heparin (POH), chemically sulfated laminarin (CSL), chemically sulfated alginic acid (CSAA), chemically sulfated pectin (CSP), dextran sulfate (DXS), heparin-derived oligosaccharides (HDO), pentosan polysulfate (PPS) and combinations thereof. In some instances, the NASP may be a low molecular weight fragment of a naturally occurring NASP. In other instances, natural NASPs may also include biochemical or chemical derivatives of naturally occurring NASPs. In certain instances, natural NASPs are fucoidans. As described above, fucoidans are naturally-occurring complex sulfated polysaccharide compounds which may be extracted from certain edible seaweeds, brown algae and echinoderms (e.g., sea urchins, sea cucumbers). Examples of suitable NASPs are also described in greater detail in U.S. patent application Ser. No. 11/140,504, filed on May 27, 2005, now U.S. Pat. No. 7,767,654 and in U.S. patent application Ser. No. 13/006,396 filed on Jan. 13, 2011, the disclosures of which are herein incorporated by reference in their entirety.

NASPs of interest may range in average molecular weight from about 10 daltons to about 500,000 daltons, such as from about 100 daltons to about 300,000 daltons, such as from 1000 daltons to 250,000 daltons, including 1000 daltons to 150,000 daltons. Molecular weights of NASPs can be determined by any convenient protocol, such as for example, gel permeation chromatography or high-performance size-exclusion chromatography (HPSEC), capillary electrophoresis, PAGE (polyacrylamide gel electrophoresis), agarose gel electrophoresis, among others.

In some embodiments, NASPs of interest may be heterogeneous mixtures of sulfated polysaccharides having varying molecular weights. For example, in some instances, 5% or more of the NASP composition has a molecular weight that ranges from 10 to 30,000 daltons, such as 10% or more, such as 25% or more, such as 50% or more, such as 75% or more, such as 90% or more, including 95% or more of the NASP composition has a molecular weight that ranges from 10 to 30,000 daltons. In other embodiments, 5% or more of the NASP composition has a molecular weight that ranges from 30,000 daltons to 75,000 daltons, such as 10% or more, such as 25% or more, such as 50% or more, such as 75% or more, such as 90% or more, including 95% or more of the NASP composition has a molecular weight that ranges from 30,000 to 75,000 daltons. In yet other embodiments, 5% or more of the NASP composition has a molecular weight that are greater than 75,000 daltons, such as 10% or more, such as 25% or more, such as 50% or more, such as 75% or more, such as 90% or more, including 95% or more of the NASP composition has a molecular weight that is greater than 75,000 daltons.

In certain embodiments, low molecular weight NASPs may be employed for enhancing blood coagulation as provided by methods and compositions of the invention. By "low molecular weight NASP" is meant a NASP having a weight average molecular weight that ranges from about 10 to 30,000 daltons, such as for example 100 to 30,000 daltons, such as 500 to 25,000 daltons, such as 1000 to 15,000 daltons and including 5000 to 10,000 daltons. Examples of low molecular weight NASPs may include, but are not limited to naturally occurring or synthetic NASPs having a molecular weight ranging from 10 to 30,000 daltons, such as from 5000 to 10,000 daltons, fragments of larger molecular weight NASPs produced by acid or enzyme hydrolysis of the larger molecular weight NASP, or may be isolated fractions having molecular weights ranging from 10 to 30,000 daltons, such as 5000 to 10,000 daltons from a fractionated NASP sample.

In certain embodiments, compositions of the present invention include a gastrointestinal epithelial barrier permeation enhancer (e.g., sodium caprate, deoxycholate, bromelain or chitosan) and a low molecular weight natural NASP. For instance, compositions of interest may include a *Fucus vesiculosus* fucoidan having a molecular weight of 20,000 daltons or less in combination with a gastrointestinal epithelial barrier permeation enhancer. For example, compositions of interest may include one or more of *Fucus vesiculosus* F.v. DS1001108, *Fucus vesiculosus* F.v. SK110144B in combination with one or more of deoxycholate, bromelain and chitosan. In another example, compositions of interest may include one or more of *Fucus vesiculosus* F.v. DS 1001108, *Fucus vesiculosus* F.v. SK110144B in combination with a mixture of chitosan and bromelain. In certain other embodiments, compositions of the present invention include a gastrointestinal epithelial barrier permeation enhancer (e.g., sodium caprate, deoxycholate, bromelain or chitosan) and low molecular weight synthetic NASP. For instance, certain compositions may include one or more of a sulfated 6-carboxylcodextrin, a sulfated β-cyclodextrin and a sulfated maltopentose having a molecular weight of 25,000 daltons or less in combination with a gastrointestinal epithelial barrier permeation enhancer. For example, compositions of interest may include one or more of a 24,000 dalton sulfated 6-carboxylcodextrin, a 14,000 dalton sulfated 6-carboxylcodextrin, a sulfated β-cyclodextrin and a sulfated maltopentose in combination with one or more of deoxycholate, bromelain and chitosan. In another example, compositions of interest may include one or more of a 24,000 dalton sulfated 6-carboxylcodextrin, a 14,000 dalton sulfated 6-carboxylcodextrin, a sulfated β-cyclodextrin and a sulfated maltopentose in combination with a mixture of chitosan and bromelain.

In some embodiments, NASPs are extracted from a biological source and may be fractionated to isolate low molecular weight NASPs (i.e., fractions containing NASPs having molecular weight ranging from 10-30,000 daltons). Any convenient protocol may be used to fractionate NASPs of interest, including but not limited to size exclusion chromatography, gel permeation chromatography, capillary electrophoresis, among others.

In certain instances, low molecular weight NASPs obtained by fractionating a NASP sample may be employed for enhancing blood coagulation as provided by the methods and compositions of the invention. For example, NASPs extracted from a biological source may be fractionated to isolate NASPs having molecular weights that range from 10 to 30,000 daltons, such as 10 to 5000 daltons, such as 5000 to 10,000 daltons, such as 10,000 to 15,000 daltons, and including 15,000 to 30,000 daltons. In certain embodiments, one or more of these fractions may be orally administered in combination with a gastrointestinal epithelial barrier permeation enhancer for enhancing blood coagulation in a subject, such as by the methods described above.

In certain embodiments, different molecular weight fractions may be prepared by acid-hydrolysis or radical depolymerization of high molecular weight NASP. The molecular weight ranges of the resulting products may be adjusted based upon the stringency of the hydrolysis or depolymerization conditions employed. Fractions may then be further purified using ion exchange chromatography. For instance, to obtain middle and low molecular weight fractions of NASP, high molecular weight NASP may be hydrolyzed using an acid such as HCl (or any other suitable acid) at concentrations ranging from 0.02 to 1.5 M and at temperatures ranging from 25° C. to 80° C. Hydrolysis reaction times will typically range from 15 minutes to several hours. The resulting hydrolyzed reaction mixture is then neutralized by addition of base (e.g., sodium hydroxide). Salts are subsequently removed, for example, by electrodialysis, and the hydrolysis products are analyzed to determine weight average molecular weight, saccharide content, and sulfur content, using conventional analytical techniques for carbohydrate analysis. Alternatively, enzymatic methods may be employed to degrade NASPs using, e.g., glycosidases. NASPs for use in the invention may be heterogeneous or homogeneous, depending upon the degree of separation employed.

In certain embodiments, oral dosage compositions of the invention include a blood coagulation factor in combination with a gastrointestinal epithelial barrier permeation enhancer and a fucoidan, such as for example, Fucoidan 5307002, *Fucus vesiculosus*, max. MW peak 126.7 kD; Fucoidan VG49, *Fucus vesiculosus*, hydrolyzed sample of 5307002 of lower MW, max. MW peak 22.5 kD; Fucoidan VG57, *Undaria pinnatifida*, high charge (high sulfation, deacetylated); Fucoidan GFS (5508005), *Undaria pinnatifida*, depyrogenated; Fucoidan GFS (L/FVF-01091), *Fucus vesiculosus*, depyrogenated, max. MW peak 125 kD; Fucoidan GFS (L/FVF-01092), *Fucus vesiculosus*, depyrogenated, max. MW peak 260 kD; Fucoidan GFS (L/FVF-01093), *Fucus vesiculosus*, hydrolyzed depyrogenated, max. MW peak 36 kD; Maritech® *Ecklonia radiata* extract; Maritech® *Ecklonia maxima* extract; Maritech® *Macrocystis pyrifera* extract; Maritech® Immune trial Fucoidan Blend; and any combinations thereof.

In other embodiments, oral dosage compositions of the invention may include a synthetic NASP in combination with a gastrointestinal epithelial barrier permeation enhancer. Synthetic NASPs are sulfated polysaccharides which are partially or wholly produced by man-made methods (e.g., chemical synthesis). For example, the synthetic NASP may be a sulfated oligomer, such as a sulfated oligosaccharide or a sulfated aliphatic. In certain instances, synthetic NASPs are sulfated pentoses, sulfated hexoses or sulfated cyclodextrins. For example, synthetic NASPs may include, but are not limited to sulfated maltopentoses, sulfated beta-cyclodextrins, sulfated 6-Carboxylcodextrin and derivatives thereof.

Oral dosage compositions of the invention may include one or more NASPs, as desired. For example, two or more NASPs may be combined, such as three or more NASPs and including four or more NASPs. Where more than one NASP is combined together, all of the NASPs may be natural NASPs, all of the NASPs may be synthetic NASPs or any combination thereof. Where oral compositions include more than one NASP, the mass percentage of each NASP in the composition may vary, ranging from 1% or more of the total mass of the composition, such as 2% or more, such as 5% or more, such as 10% or more, such as 25% or more and including as 50% or more of the total mass of the composition.

In embodiments of the invention, the mass ratio of the one or more NASPs and the one or more gastrointestinal epithelial barrier permeation enhancers in the oral dosage compositions may vary, ranging between 1:1 and 1:2.5; 1:2.5 and 1:5; 1:5 and 1:10; 1:10 and 1:25; 1:25 and 1:50; 1:50 and 1:100; 1:100 and 1:150; 1:150 and 1:200; 1:200 and 1:250; 1:250 and 1:500; 1:500 and 1:1000, or a range thereof. For example, the mass ratio of the NASP to the gastrointestinal epithelial barrier permeation enhancer may range between 1:1 and 1:10; 1:5 and 1:25; 1:10 and 1:50; 1:25 and 1:100; 1:50 and 1:500; or 1:100 and 1:1000. In some embodiments, the mass ratio of the gastrointestinal epithelial barrier permeation enhancer to the NASP ranges between 1:1 and 1:2.5; 1:2.5 and 1:5; 1:5 and 1:10; 1:10 and 1:25; 1:25 and 1:50; 1:50 and 1:100; 1:100 and 1:150; 1:150 and 1:200; 1:200 and 1:250; 1:250 and 1:500; 1:500 and 1:1000, or a range thereof. For example, the mass ratio of the gastrointestinal epithelial barrier permeation enhancer to the NASP may range between 1:1 and 1:10; 1:5 and 1:25; 1:10 and 1:50; 1:25 and 1:100; 1:50 and 1:500; or 1:100 and 1:1000.

In addition, oral dosage compositions of the invention may also include one or more blood coagulation factors. For example, compositions may include an amount of one or more NASPs and one or more gastrointestinal epithelial barrier permeation enhancers in combination with one or more blood coagulation factors. Blood coagulation factors of interest include, but are not limited to factor XI, factor XII, prekallikrein, high molecular weight kininogen (HMWK), factor V, factor VII, factor VIII, factor IX, factor X, factor XIII, factor II, factor VIIa, and von Willebrands factor, factor Xa, factor IXa, factor XIa, factor XIIa, and VIIIa, prekallekrein, and high-molecular weight kininogen, tissue factor, factor VIIa, factor Va, and factor Xa.

The amount (i.e., mass) of each of the NASP, the gastrointestinal epithelial barrier permeation enhancer and blood coagulation factor in oral dosage compositions of interest may vary, ranging from 0.001 mg to 1000 mg, such as 0.01 mg to 500 mg, such as 0.1 mg to 250 mg, such as 0.5 mg to 100 mg, such as 1 mg to 50 mg, including 1 mg to 10 mg. As such, in the subject compositions, the mass ratio of the NASP and gastrointestinal epithelial barrier permeation enhancer to blood coagulation factor may vary, and in some instances may range between 1:1 and 1:2.5; 1:2.5 and 1:5; 1:5 and 1:10; 1:10 and 1:25; 1:25 and 1:50; 1:50 and 1:100; 1:100 and 1:150; 1:150 and 1:200; 1:200 and 1:250; 1:250 and 1:500; 1:500 and 1:1000, or a range thereof. For example, the mass ratio of the NASP and gastrointestinal epithelial barrier permeation enhancer to blood coagulation factor may range between 1:1 and 1:10; 1:5 and 1:25; 1:10 and 1:50; 1:25 and 1:100; 1:50 and 1:500; or 1:100 and 1:1000. In some embodiments, the mass ratio of the blood coagulation factor to the NASP and gastrointestinal epithelial barrier permeation enhancer ranges between 1:1 and 1:2.5; 1:2.5 and 1:5; 1:5 and 1:10; 1:10 and 1:25; 1:25 and 1:50; 1:50 and 1:100; 1:100 and 1:150; 1:150 and 1:200; 1:200 and 1:250; 1:250 and 1:500; 1:500 and 1:1000, or a range thereof. For example, the mass ratio of the blood coagulation factor to the composition that contains a NASP and gastrointestinal epithelial barrier permeation enhancer may range between 1:1 and 1:10; 1:5 and 1:25; 1:10 and 1:50; 1:25 and 1:100; 1:50 and 1:500; or 1:100 and 1:1000.

Oral dosage compositions may be homogeneous, containing only a single type of NASP and single type of gastrointestinal epithelial permeation barrier enhancer. In other embodiments, compositions of interest are heterogenous mixtures of two or more NASPs or two or more gastrointestinal epithelial permeation barrier enhancers. For example, heterogenous mixtures may contain two or more NASPs and two or more gastrointestinal epithelial permeation barrier enhancers. In other instances, heterogeneous mixtures may contain one NASP and two or more gastrointestinal epithelial permeation barrier enhancers. In yet other instances, heterogeneous mixtures may contain two or more NASPs and one gastrointestinal epithelial permeation barrier enhancer.

In certain embodiments, oral dosage compositions of the invention may further include one or more pharmaceutically acceptable excipients or oral dosage delivery vehicle as part of a pharmaceutical composition. Excipients may include, but are not limited to, carbohydrates, inorganic salts, antimicrobial agents, antioxidants, surfactants, water, alcohols, polyols, glycerine, vegetable oils, phospholipids, buffers, acids, bases, and any combinations thereof. A carbohydrate such as a sugar, a derivatized sugar such as an alditol, aldonic acid, an esterified sugar, and/or a sugar polymer may also be employed. Some carbohydrate excipients of interest include, for example, monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like. Inorganic salts may include, but are not limited to citric acid, sodium chloride, potassium chloride, sodium sulfate, potassium nitrate, sodium phosphate monobasic, sodium phosphate dibasic, and any combinations thereof.

In certain embodiments, oral dosage compositions of the invention may also include an antimicrobial agent for preventing or deterring microbial growth, such as for example benzalkonium chloride, benzethonium chloride, benzyl alcohol, cetylpyridinium chloride, chlorobutanol, phenol, phenylethyl alcohol, phenylmercuric nitrate, thimersol, and any combinations thereof.

One or more antioxidants may also be employed. Antioxidants, which can reduce or prevent oxidation and thus deterioration of the composition, may include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and any combinations thereof.

One or more surfactants may also be included in compositions of the invention. For example, suitable surfactants may include, but are not limited to polysorbates, such as "Tween 20" and "Tween 80," and pluronics such as F68 and F88 (BASF, Mount Olive, N.J.); sorbitan esters; lipids, such as phospholipids such as lecithin and other phosphatidylcholines, phosphatidylethanolamines (although preferably not in liposomal form), fatty acids and fatty esters; steroids, such as cholesterol; chelating agents, such as EDTA; and zinc and other cations.

Acids or bases may also be present in oral dosage compositions of the invention. For example, acids may include but are not limited to hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and any combinations thereof. Examples bases include, but are not limited to sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and any combinations thereof.

The amount of any individual excipient in the oral dosage composition will vary depending on the nature and function of the excipient, oral dosage delivery vehicle and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects. Generally, however, the excipient(s) will be present in the oral dosage composition in an amount of about 1% to about 99% by weight, such as from about 5% to about 98% by weight, such as from about 15 to about 95% by weight of the excipient, including less than 30% by weight. Pharmaceutical excipients along with other excipients that may be employed in compositions of interest are described in "Remington: The Science & Practice of Pharmacy", 19th ed., Williams & Williams, (1995), the "Physician's Desk Reference", 52nd ed., Medical Economics, Montvale, N.J. (1998), and Kibbe, A. H., Handbook of Pharmaceutical Excipients, 3rd Edition, American Pharmaceutical Association, Washington, D.C., 2000, the disclosure of which is herein incorporated by reference.

As described above, compositions of the invention may be administered by any convenient mode of administration so long as the composition is resorbed through the gastrointestinal epithelium (e.g., orally or by nasogastric tube). As such, the formulation may vary. For example, compositions of the invention may be powders or lyophilates that can be reconstituted with a solvent prior to use, dry insoluble compositions for combination with a vehicle prior to use, and emulsions and liquid concentrates for dilution prior to administration. Diluents for reconstituting solid compositions may include, but are not limited to bacteriostatic water for injection, dextrose 5% in water, phosphate buffered saline, Ringer's solution, saline, sterile water, deionized water, and any combinations thereof. In some embodiments, pharmaceutical compositions of the invention may be in the form of a liquid solution or suspension, syrup, tablet, capsule, powder, gel, or any combination thereof for ingestion or application by a nasogastric tube. For example, oral dosage compositions of the invention may be pre-loaded into a tablet, a capsule, caplet device, or the like, depending upon the intended use. In certain embodiments, the compositions are in unit dosage form, such that an amount of the composition is ready in a single oral dose, in a premeasured or pre-packaged form.

Utility

The subject methods and compositions find use in any situation where there is a desire to enhance blood coagulation in a subject, a desire to enhance resorption of NASPs through the gastrointestinal system and the subject is responsive to treatment with a NASP and a gastrointestinal epithelial barrier permeation enhancer. In certain embodiments, the subject methods and compositions may be employed to treat bleeding disorders, such as a chronic or acute bleeding disorder, a congenital coagulation disorder caused by a blood factor deficiency, an acquired coagulation disorder and administration of an anticoagulant. For example, bleeding disorders may include, but are not limited to hemophilia A, hemophilia B, von Willebrand disease, idiopathic thrombocytopenia, a deficiency of one or more contact factors, such as Factor XI, Factor XII, prekallikrein, and high molecular weight kininogen (HMWK), a deficiency of one or more factors associated with clinically significant bleeding, such as Factor V, Factor VII, Factor VIII, Factor IX, Factor X, Factor XIII, Factor II (hypoprothrombinemia), and von Willebrands factor, a vitamin K deficiency, a disorder of fibrinogen, including afibrinogenemia, hypofibrinogenemia, and dysfibrinogenemia, an $alpha_2$-antiplasmin deficiency, and excessive bleeding such as caused by liver disease, renal disease, thrombocytopenia, platelet dysfunction, hematomas, internal hemorrhage, hemarthroses, surgery, trauma, hypothermia, menstruation, and pregnancy.

The subject methods and compositions also find use in enhancing blood coagulation to treat a congenital coagulation disorder or an acquired coagulation disorder caused by a blood factor deficiency. The blood factor deficiency may be caused by deficiencies of one or more factors, including but not limited to, factor V, factor VII, factor VIII, factor IX, factor XI, factor XII, factor XIII, and von Willebrand factor.

The subject methods and compositions also find use in enhancing blood coagulation in order to improve hemostasis in treating bleeding disorders, such as those associated with deficiencies of coagulation factors or for reversing the effects of anticoagulants in a subject. For example, enhancing blood coagulation by methods and compositions of the invention may be employed to treat bleeding disorders such as congenital coagulation disorders, acquired coagulation disorders, and hemorrhagic conditions induced by trauma. Examples of bleeding disorders that may be treated with NASPs and gastrointestinal epithelial barrier permeation enhancers include, but are not limited to, hemophilia A, hemophilia B, von Willebrand disease, idiopathic thrombocytopenia, a deficiency of one or more contact factors, such as Factor XI, Factor XII, prekallikrein, and high molecular weight kininogen (HMWK), a deficiency of one or more factors associated with clinically significant bleeding, such as Factor V, Factor VII, Factor VIII, Factor IX, Factor X, Factor XIII, Factor II (hypoprothrombinemia), and von Willebrands factor, a vitamin K deficiency, a disorder of fibrinogen, including afibrinogenemia, hypofibrinogenemia, and dysfibrinogenemia, an $alpha_2$-antiplasmin deficiency, and excessive bleeding such as caused by liver disease, renal disease, thrombocytopenia, platelet dysfunction, hematomas, internal hemorrhage, hemarthroses, surgery, trauma, hypothermia, menstruation, and pregnancy. In certain embodiments, methods and compositions of the invention are used to treat congenital coagulation disorders including hemophilia A, hemophilia B, and von Willebrands disease. In other embodiments, NASPs are used to treat acquired coagulation disorders, including deficiencies of factor VIII, von Willebrand factor, factor IX, factor V, factor XI, factor XII and factor XIII, particularly disorders caused by inhibitors or autoimmunity against blood coagulation factors, or haemostatic disorders caused by a disease or condition that results in reduced synthesis of coagulation factors.

In some embodiments, the bleeding disorder may be a chronic condition (e.g., a congenital or acquired coagulation factor deficiency) requiring the subject methods and compositions in multiple doses over an extended period. Alternatively, methods and compositions of the invention may be orally administered to treat an acute condition (e.g., bleeding caused by surgery or trauma, or factor inhibitor/autoimmune episodes in subjects receiving coagulation replacement therapy) in single or multiple doses for a relatively short period, for example one to two weeks.

The subject methods and compositions also find use in enhancing blood coagulation in a subject undergoing a surgical or invasive procedure.

The subject methods and compositions also find use in enhancing blood coagulation in order to reverse the effects of an anticoagulant in a subject, the method comprising administering a therapeutically effective amount of a composition comprising a procoagulant amount of a NASP in combination with a gastrointestinal epithelial barrier permeation enhancer to the subject. In certain embodiments, the subject may have been treated with an anticoagulant including, but not limited to, heparin, a coumarin derivative, such as warfarin or dicumarol, TFPI, AT III, lupus anticoagulant, nematode anticoagulant peptide (NAPc2), active-site blocked factor VIIa (factor VIIai), factor IXa inhibitors, factor Xa inhibitors, including fondaparinux, idraparinux, DX-9065a, and razaxaban (DPC906), inhibitors of factors Va and VIIIa, including activated protein C (APC) and soluble thrombomodulin, thrombin inhibitors, including hirudin, bivalirudin, argatroban, and ximelagatran. In certain embodiments, the anticoagulant in the subject may be an antibody that binds a clotting factor, including but not limited to, an antibody that binds to Factor V, Factor VII, Factor VIII, Factor IX, Factor X, Factor XIII, Factor II, Factor XI, Factor XII, von Willebrands factor, prekallikrein, or high molecular weight kininogen (HMWK).

In another aspect, the invention provides a method for treating a subject undergoing a surgical or invasive procedure wherein improved blood clotting would be desirable, comprising orally administering a therapeutically effective amount of a composition comprising a procoagulant amount of a NASP in combination with a gastrointestinal epithelial barrier permeation enhancer as detailed herein to the subject.

In certain embodiments, the NASP and gastrointestinal epithelial barrier permeation enhancer can be coadministered with one or more different NASPs and one or more different gastrointestinal epithelial barrier permeation enhancers, and/or in combination with one or more other therapeutic agents to the subject undergoing a surgical or invasive procedure. For example, the subject may be administered a therapeutically effective amount of one or more factors selected from the group consisting of factor XI, factor XII, prekallikrein, high molecular weight kininogen (HMWK), factor V, factor VII, factor VIII, factor IX, factor X, factor XIII, factor II, factor VIIa, and von Willebrands factor. Treatment may further comprise administering a procoagulant, such as an activator of the intrinsic coagulation pathway, including factor Xa, factor IXa, factor XIa, factor XIIa, and VIIIa, prekallekrein, and high-molecular weight kininogen; or an activator of the extrinsic coagulation pathway, including tissue factor, factor VIIa, factor Va, and factor Xa. Therapeutic agents used to treat a subject undergoing a surgical or invasive procedure can be administered in the same or different compositions and concurrently, before, or after administration of the NASP and the gastrointestinal epithelial barrier permeation enhancer.

As disclosed above, hemostatic agents, blood factors, and medications may also be employed. For example, the subject may be administered one or more blood coagulation factors such as factor XI, factor XII, prekallikrein, high molecular weight kininogen (HMWK), factor V, factor VII, factor VIII, factor IX, factor X, factor XIII, factor II, factor VIIa, von Willebrands factor, factor Xa, factor IXa, factor XIa, factor XIIa, and VIIIa, prekallekrein, and high-molecular weight kininogen, tissue factor, factor VIIa, factor Va, and factor Xa.

Kits

Also provided are kits for use in practicing the subject methods, where the kits may include one or more of the above compositions, e.g., an NASP composition, a gastrointestinal epithelial barrier permeation enhancer composition and/or blood coagulation factor, as described above. The kit may further include other components, e.g., administration devices, fluid sources, etc., which may find use in practicing the subject methods. Various components may be packaged as desired, e.g., together or separately.

In addition to above mentioned components, the subject kits may further include instructions for using the components of the kit to practice the subject methods. The instructions for practicing the subject methods are generally recorded on a suitable recording medium. For example, the instructions may be printed, such as on paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

EXPERIMENTAL

The following examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Bioavailability and Resorption Studies of NASPs in Combination with Gastrointestinal Epithelial Barrier Permeation Enhancers The bioavailability of NASPs in combination with gastrointestinal epithelial barrier permeation enhancers of interest were studied using the CaCo-2 cell model screening. This method utilizes a human colon carcinoma cell line that expresses a wide range of transporter proteins on its cell membranes. Cell layers are grown on a membrane surface that separates two compartments (24-well plate). An example of the experimental setup for these experiments is illustrated in FIG. 1. Selected NASP and gastrointestinal epithelial barrier permeation enhancer samples were dissolved in RPMI cell medium at a concentration of 1 mg/mL and applied onto the cells in the apical compartment. Cells were incubated at 37° C. in 5% $CO_2$. Medium samples were removed from the basolateral and apical compartment at different time points. The condition of the cell layer was monitored by measurement of the transepithelial electrical resistance (TEER). Samples were analyzed by thrombin generation assay (CAT). NASP concentration was calculated based on activity from CAT assay. Experimental details of thrombin generation assays and other blood coagulation assays are described in U.S. patent application Ser. No. 11/140,504, filed on May 27, 2005, now U.S. Pat. No. 7,767,654, and U.S. patent application Ser. No. 13/006,396, filed on Jan. 13, 2011, the disclosures of which is herein incorporated by reference.

All NASP and gastrointestinal epithelial barrier permeation enhancer samples were diluted in such a way that the sample concentration was in the range of increasing procoagulant activity. Based on the initial load concentration values, apical and basolateral concentrations were determined at 2 hour increments (e.g., 2 hours, 4 hours, 6 hours, 8 hours, including 24 hours). Based on the determined basolateral concentrations, the percent resorption was determined for each combination of compounds (i.e., NASP and gastrointestinal epithelial barrier permeation enhancers).

An example of the resorption studies described herein is illustrated in Tables 1-3 which summarize the apical and basolateral concentrations of the NASP, Fucoidan F.v. 1091 in combination with the gastrointestinal epithelial barrier permeation enhancer, Bromelain (0.5 mg/mL) in the Caco-2 cell model. Table 1 illustrates that the starting apical concentration of F.v. L/FVF1091 in combination with Bromelain is about 840 μg/mL. After about 8 hours, the apical concentration of F.v. L/FVF 1091 is reduced by about 25% to an average of about 627 μg/mL.

TABLE 1

| Sample | Start (mg/mL) | 8 hours (mg/mL) |
|---|---|---|
| F.v. L/FVF 1091 -Set 1 | 840 | 670 |
| F.v. L/FVF 1091 - Set 2 |  | 650 |
| F.v. L/FVF 1091 - Set 3 |  | 560 |

Figure 2:
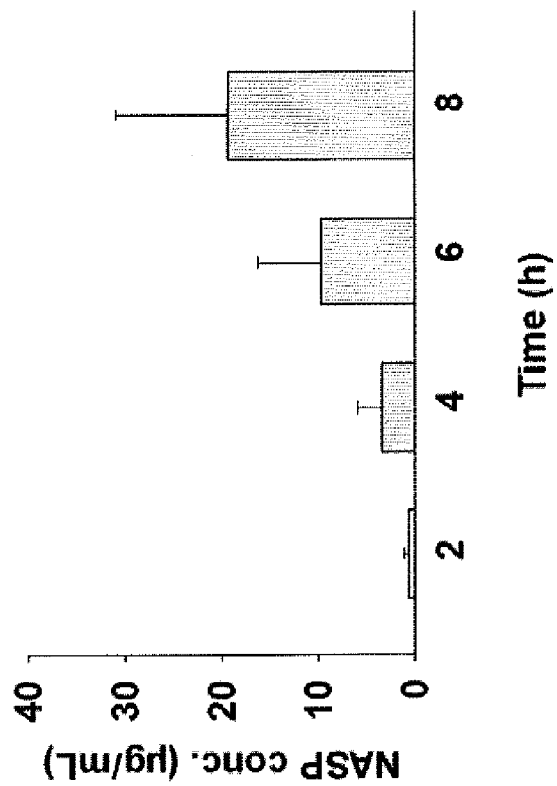
FIG. 2 shows an example of the amount of NASP in combination with a gastrointestinal epithelial barrier permeation enhancer resorbed in CaCo2 bioavailability screening for fucoidan *Fucus vesiculosus* L/FVF-1091.
Figure 3:
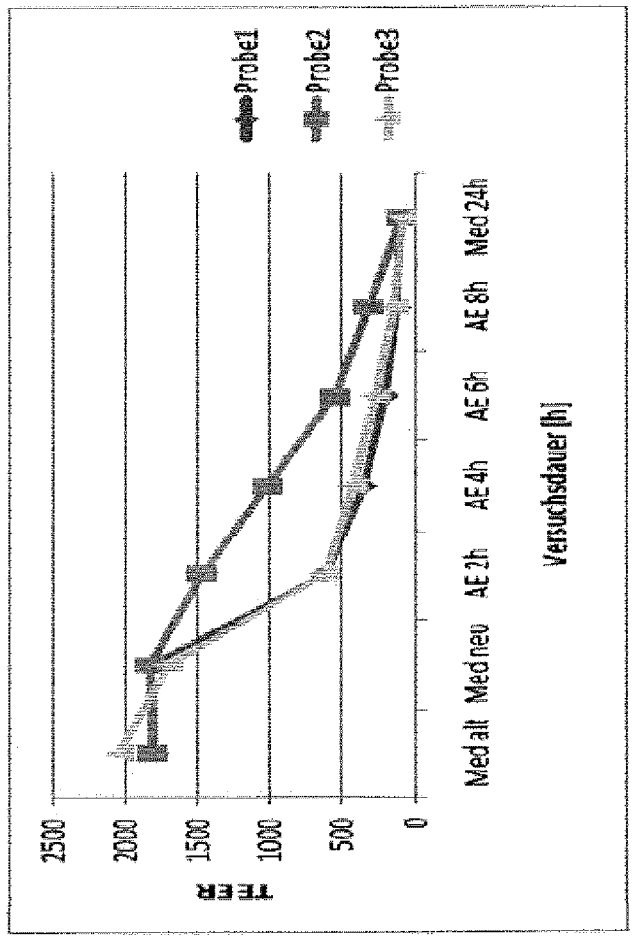
FIG. 3 shows the condition of the cell layer in the CaCo-2 bioavailability screening for fucoidan *Fucus vesiculosus* L/FVF-1091 in combination with the gastrointestinal epithelial barrier permeation enhancer bromelain as measured by transepithelial electrical resistance.

Table 2 illustrates the basolateral concentrations of F.v. L/FVF 1091 in combination with Bromelain at various time points. FIG. 2 shows the basolateral concentrations of F.v. L/FVF 1091 in the presence of Bromelain (0.5 mg/mL) in the Caco-2 system. FIG. 3 shows the condition of the cell layer as measured by the corresponding transepithelial electrical resistance curves of each trial.

TABLE 2

| Sample Concentration (μg/mL) | 2 hours | 4 hours | 6 hours | 8 hours |
|---|---|---|---|---|
| Dilution Factor | 1 | 0.9 | 0.82 | 0.74 |
| F.v. L/FVF 1091 -Set 1 | 0.8 | 5.3 | 14.5 | 29.2 |
| F.v. L/FVF 1091 - Set 2 | 0 | 0.5 | 2.1 | 6.5 |
| F.v. L/FVF 1091 - Set 3 | 0.8 | 4.2 | 12.3 | 22.2 |
| Theoretical Maximum | 190 | 171 | 156 | 141 |

Table 3 illustrates the percent (%) resorption of F.v. L/FVF 1091 in the presence of Bromelain at various time points.

TABLE 3

| Percent Resorption | 2 hours | 4 hours | 6 hours | 8 hours |
|---|---|---|---|---|
| Dilution Factor | 1 | 0.9 | 0.82 | 0.74 |
| F.v. L/FVF 1091 -Set 1 | 0.4 | 3.1 | 9.3 | 20.7 |
| F.v. L/FVF 1091 - Set 2 | 0 | 0.3 | 1.3 | 4.6 |
| F.v. L/FVF 1091 - Set 3 | 0.4 | 2.5 | 7.9 | 15.7 |

Based on Tables 2 and 3, the average resorption is 19 mg/mL of F.v. L/FVF 1091 in combination with Bromelain at 8 hours and demonstrate that the basolateral concentration of F.v. L/FVF 1091 increases with time in the presence of the gastrointestinal epithelial barrier permeation enhancer, Bromelain.

Table 4 is a summary of percent resorption of natural NASPs in the Caco-2 cell model in the presence of several gastrointestinal epithelial permeation enhancers at various concentrations. As shown in Table 4, all of the natural NASPs demonstrated increased resorption in the presence of the gastrointestinal epithelial barrier permeation enhancers of interest.

TABLE 4

| Average Percent Resorption at 8 hours | U.p.5508005 | F.v. L/FVF 1091 | F.v. DS1001108 | F.v. SK110144B |
|---|---|---|---|---|
| Molecular Weight | 380 kD | 143 kD | 18 kD | 12 kD |
| No enhancer | 0.1 | 0.7 | 0.4 | 4.0 |
| Sodium Caprate 12 mM | 3.5 | 3.7 | n/a | n/a |
| Deoxycholate - 0.06% | n/a | n/a | 1.4 | 10.7 |
| Deoxycholate - 0.08% | 4.7 | 10.9 | 10.4 | 22.6 |
| Bromelain - 0.5 mg/mL | 6.2 | 8.6 | 4.0 | 28.9 |
| Chitosan - 3% | 2.5 | 2.5 | 1.6 | 9.0 |
| Bromelain/Chitosan 0.5 mg/mL: 3% | 19.6 | 36.9 | 28.8 | 55.0 |

TABLE 4-continued

| Average Percent Resorption at 8 hours | U.p.5508005 | F.v. L/ FVF 1091 | F.v. DS1001108 | F.v. SK110144B |
|---|---|---|---|---|
| Bromelain/Chitosan 0.05 mg/mL: 3% | n/a | 3.1 | 6.7 | n/a |
| Bromelain/Chitosan 0.25 mg/mL: 1.5% | n/a | 4.4 | 7.3 | n/a |
| Bromelain/Chitosan 0.5 mg/mL: 0.3% | n/a | 2.6 | 8.7 | n/a |

Table 5 is a summary of percent resorption of synthetic NASPs in the Caco-2 cell model in the presence of several gastrointestinal epithelial permeation enhancers at various concentrations. As shown in Table 5, all of the synthetic NASPs demonstrated increased resorption in the presence of the gastrointestinal epithelial barrier permeation enhancers of interest.

TABLE 5

| Average Percent Resorption at 8 hours | Sulfated 6-Carboxyicodextrin | Sulfated 6-Carboxyicodextrin | Sulfated β-cyclodextrin | Sulfated Maltopentose |
|---|---|---|---|---|
| Molecular Weight | 24 kD | 14 kD | 3 kD | 3 kD |
| No enhancer | 1.6 | 3.8 | 0 | 0 |
| Sodium Caprate 12 mM | n/a | n/a | 19.3 | 13.1 |
| Deoxycholate - 0.06% | 4.9 | n/a | 20.6 | 67.4 |
| Deoxycholate - 0.08% | 14.7 | 27.2 | 36.1 | 113.2 |
| Bromelain - 0.5 mg/mL | 10.0 | 17.7 | 24.7 | 48.6 |
| Chitosan - 3% | 2.6 | 5.4 | 15.6 | 35.7 |
| Bromelain/Chitosan 0.5 mg/mL: 3% | 36.8 | 44.5 | 59.8 | 158.8 |

FIGS. 4-8 illustrate resorption of some natural NASPs of interest in Caco-2 cell models as determined by TGA and liquid chromatography/mass spectrometry in combination with different gastrointestinal epithelial barrier permeation enhancers. FIGS. 9 and 10 illustrate resorption of some synthetic NASPs of interest in Caco-2 cell models as determined by TGA and liquid chromatography/mass spectrometry in combination with different gastrointestinal epithelial barrier permeation enhancers.

Figure 4A:
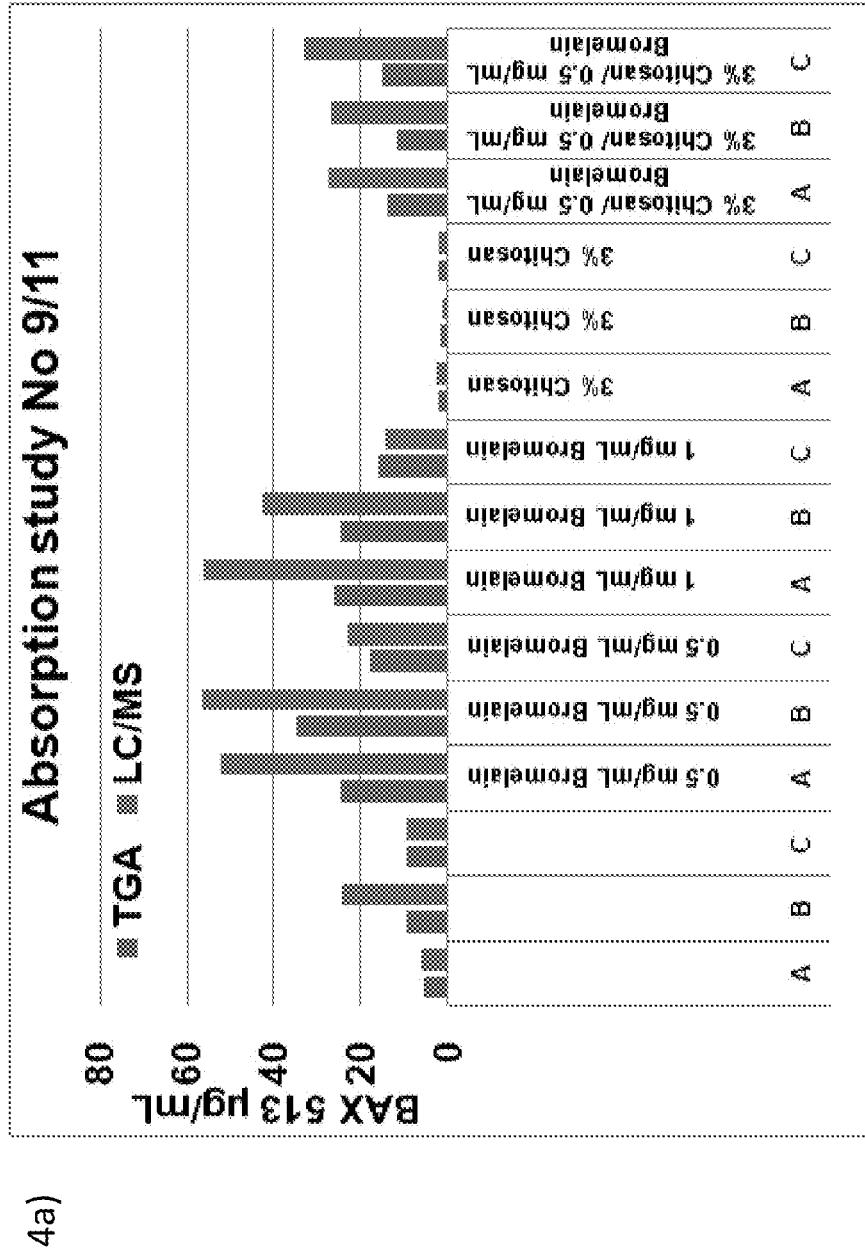
FIGS. 4a-b show an example of resorption data acquired in the CaCo-2 bioavailability screening for fucoidan BAX513 in combination with gastrointestinal epithelial barrier permeation enhancers.
Figure 4B:
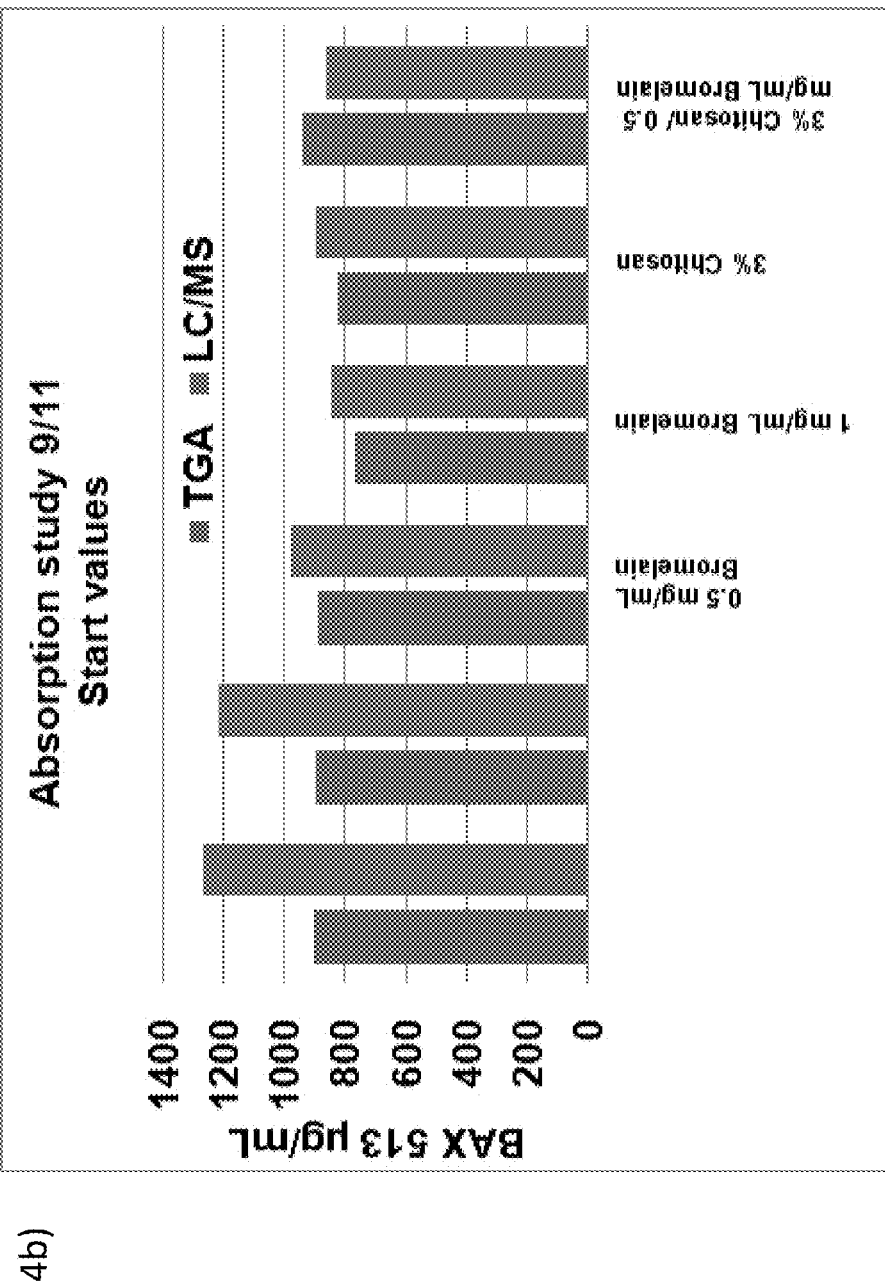

FIGS. 4a-b illustrate the NASP, BAX513 resorption in Caco-2 cell models in the absence of any gastrointestinal epithelial barrier permeation enhancer as well as in the presence of bromelain, chitosan and in the presence of a combination of bromelain and chitosan. As illustrated in FIGS. 4a-b, basolateral concentrations of BAX513 are increased in the presence of the gastrointestinal epithelial barrier permeation enhancer, indicating that resorption of BAX513 increases when administered in combination with a gastrointestinal epithelial barrier permeation enhancer.

Figure 5A:
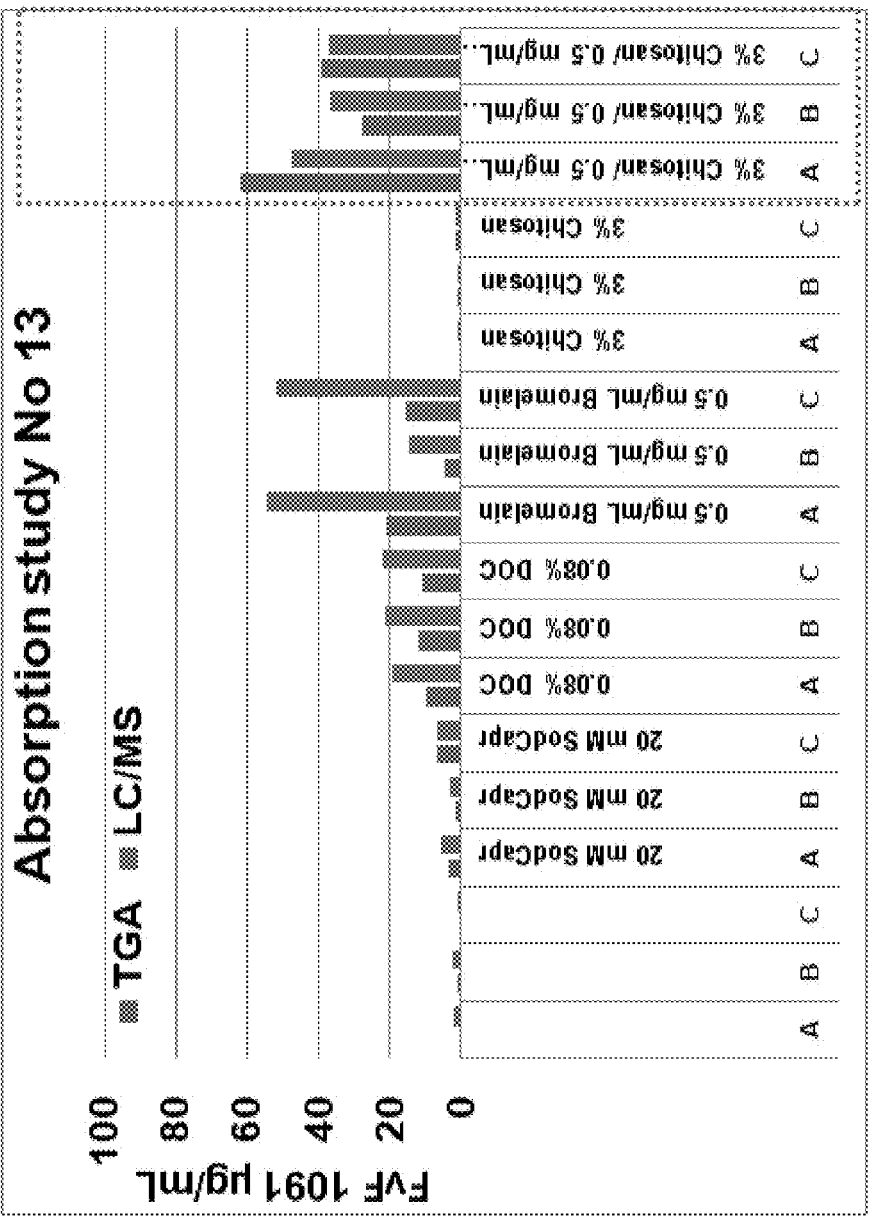
Figure 5B:
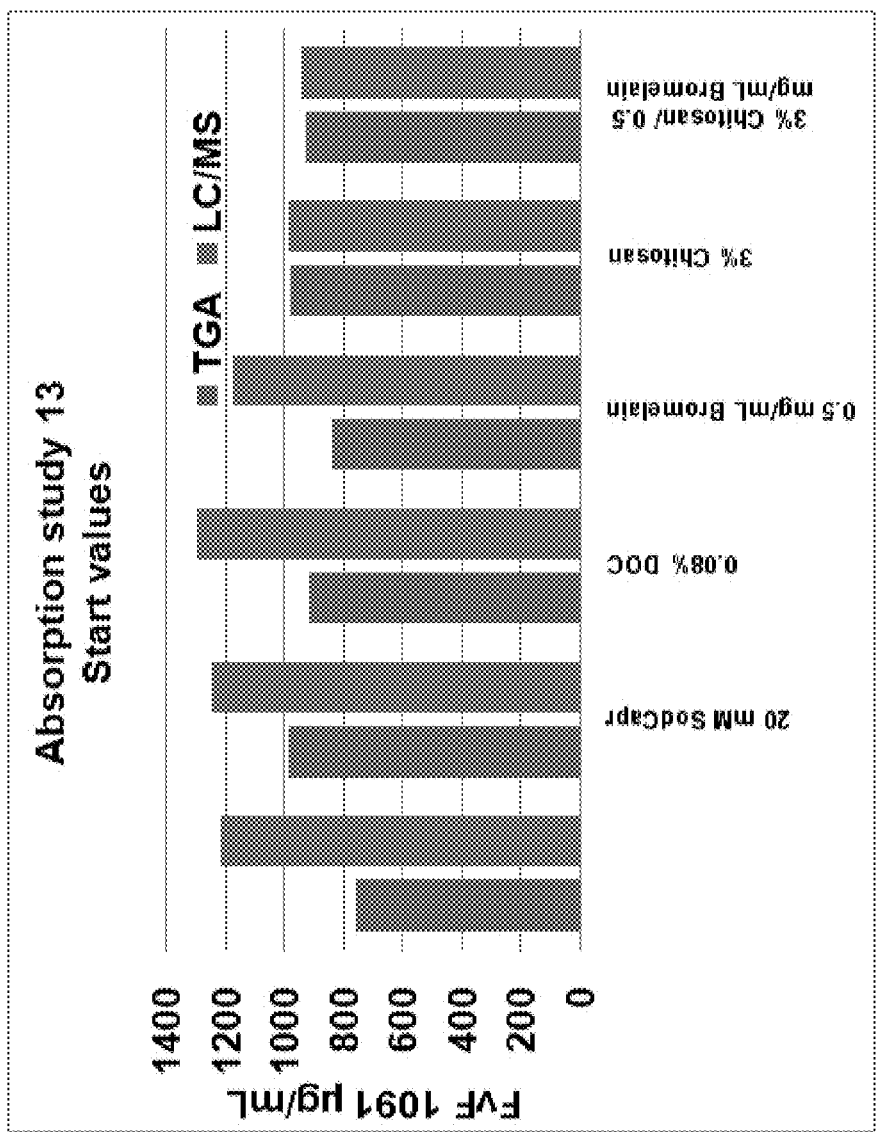

FIGS. 5a-c illustrate the NASP, Fucoidan F.v. L/FVF 1091 resorption in Caco-2 cell models in the absence of any gastrointestinal epithelial barrier permeation enhancer as well as in the presence of several different gastrointestinal epithelial barrier permeation enhancers sodium caprate, deoxycholate, bromelain, chitosan and in the presence of a combination of bromelain and chitosan. FIGS. 5a-c demonstrates that the basolateral concentrations of Fucoidan F.v. L/FVF 1091 increased in the presence of the gastrointestinal epithelial barrier permeation enhancer, indicating that resorption of Fucoidan F.v. L/FVF 1091 increases when administered in combination with a gastrointestinal epithelial barrier permeation enhancer. In particular, the resorption of Fucoidan F.v. L/FVF 1091 increases substantially when administered in the presence of a combination of chitosan and bromelain.

Figure 6A:
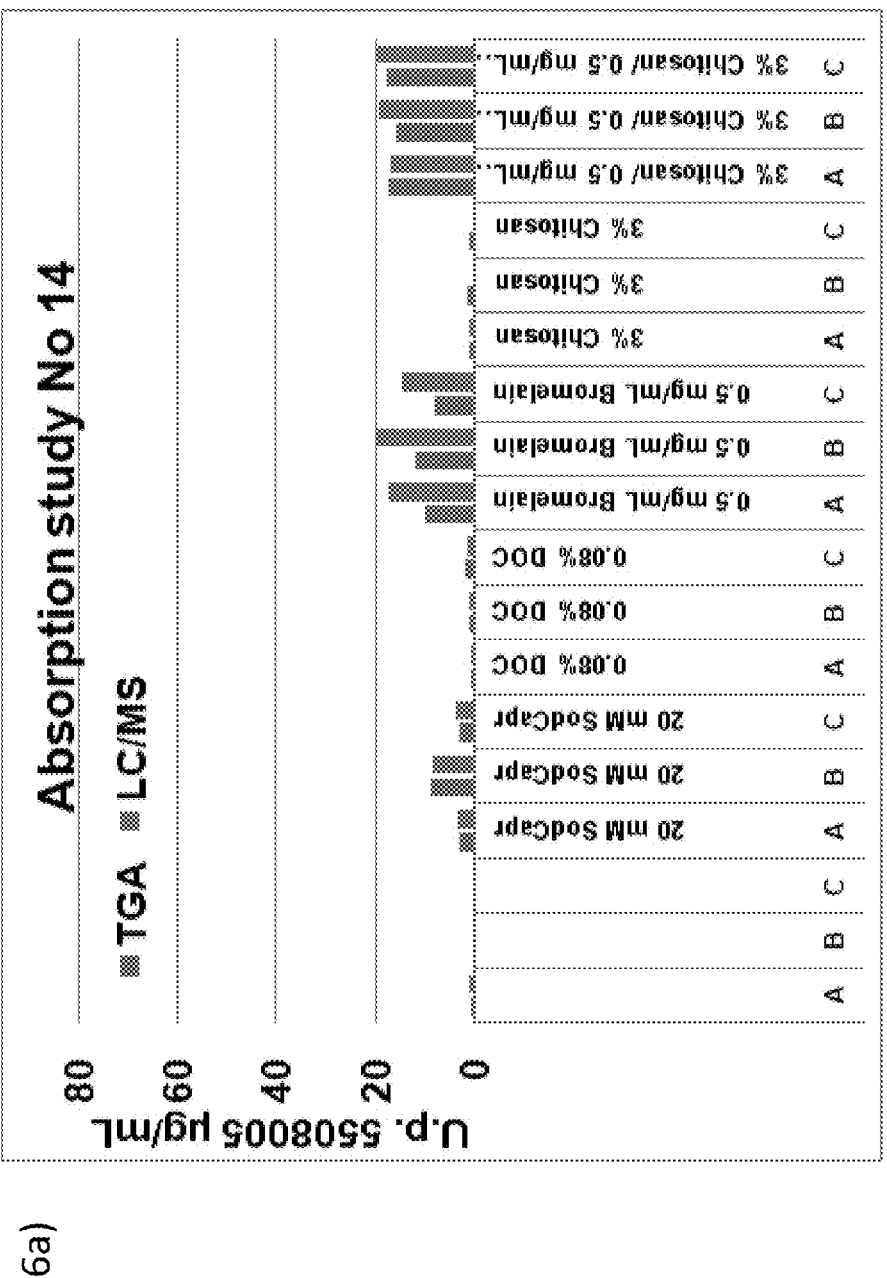
FIGS. 6a-b show an example of resorption data acquired in the CaCo-2 bioavailability screening for fucoidan U.p. 5508005 in combination with gastrointestinal epithelial barrier permeation enhancers.
Figure 6B:
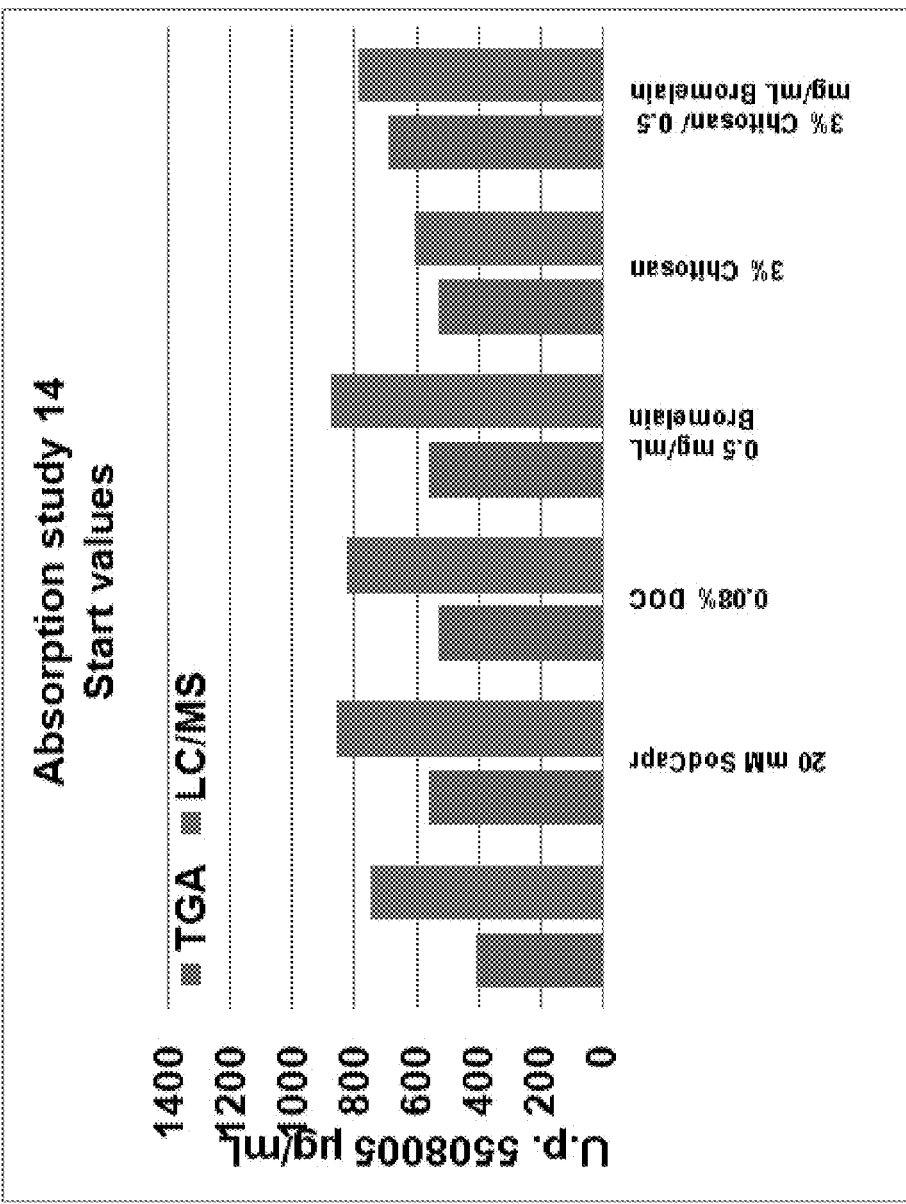

FIGS. 6a-b show the NASP, Fucoidan U.p. 5508005 resorption in Caco-2 cell models in the absence of any gastrointestinal epithelial barrier permeation enhancer as well as in the presence of gastrointestinal epithelial barrier permeation enhancers sodium caprate, deoxycholate, bromelain, chitosan and in the presence of a combination of bromelain and chitosan. FIGS. 6a-b demonstrates that the basolateral concentrations of Fucoidan U.p. 5508005 increased in the presence of a gastrointestinal epithelial barrier permeation enhancer, indicating that resorption of Fucoidan U.p. 5508005 increases when administered in combination with a gastrointestinal epithelial barrier permeation enhancer. In particular, the resorption of Fucoidan U.p. 5508005 increased substantially in the presence of sodium caprate, bromelain and in the presence of a combination of chitosan and bromelain.

Figure 7A:
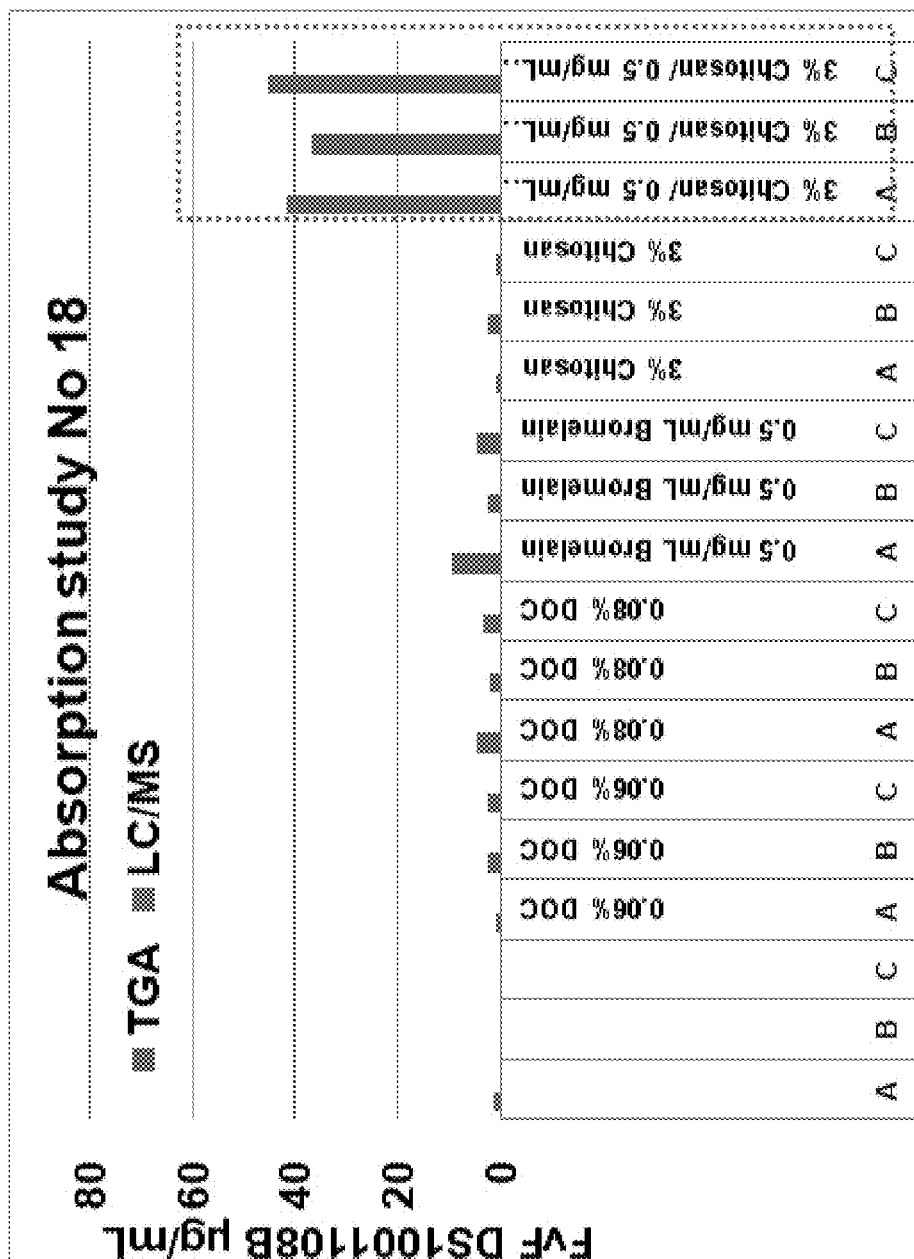
FIGS. 7a-b show an example of resorption data acquired in the CaCo-2 bioavailability screening for fucoidan F.v.F DS1001108B in combination with gastrointestinal epithelial barrier permeation enhancers.
Figure 7B:
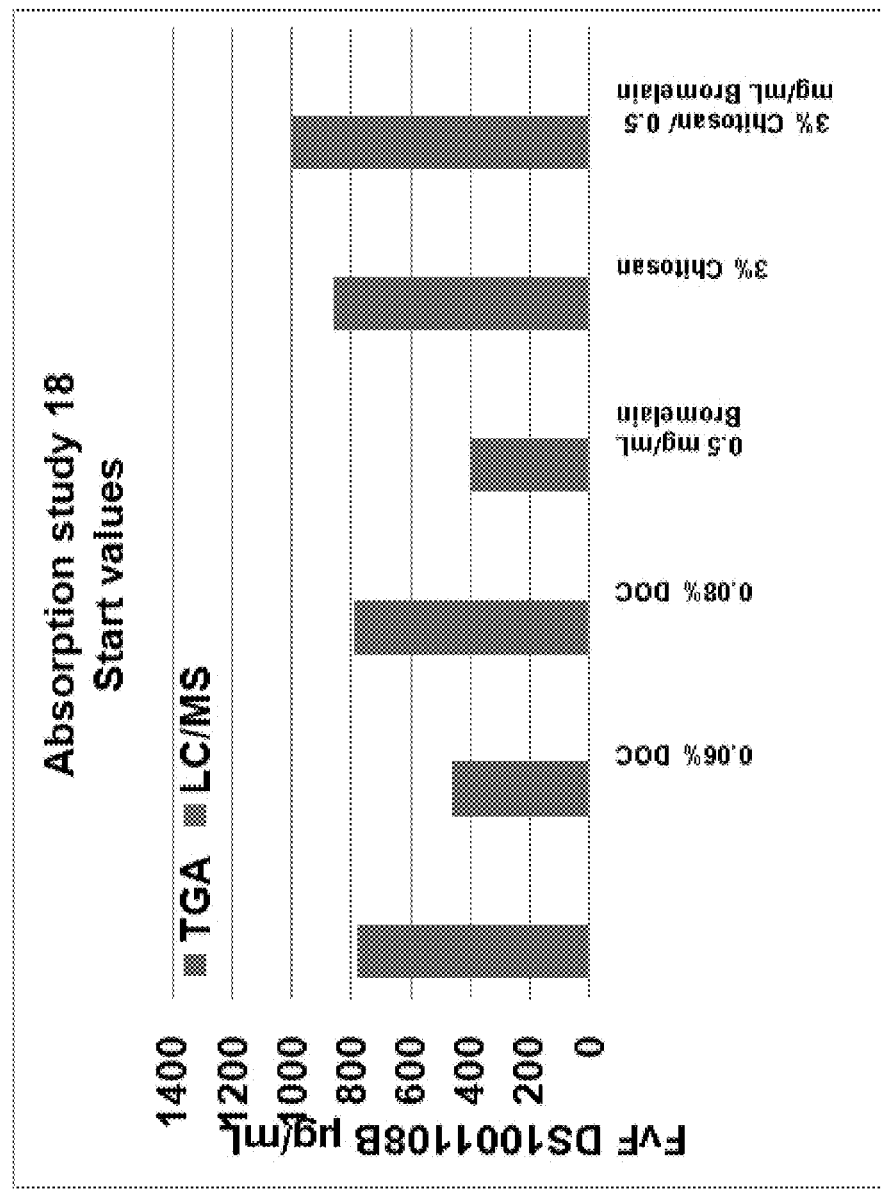

FIGS. 7a-b depict the NASP, Fucoidan FvF DS1001108B resorption in Caco-2 cell models in the absence of any gastrointestinal epithelial barrier permeation enhancer as well as in the presence of gastrointestinal epithelial barrier permeation enhancers deoxycholate (at two different concentrations), bromelain, chitosan and in the presence of a combination of bromelain and chitosan. FIGS. 7a-b illustrates that the basolateral concentrations of Fucoidan FvF DS 1001108B increased in the presence of a gastrointestinal epithelial barrier permeation enhancer, indicating that resorption of Fucoidan FvF DS1001108B increases when administered in combination with a gastrointestinal epithelial barrier permeation enhancer. In particular, the resorption of Fucoidan FvF DS 1001108B increases substantially when administered in the presence of a combination of chitosan and bromelain.

Figure 8A:
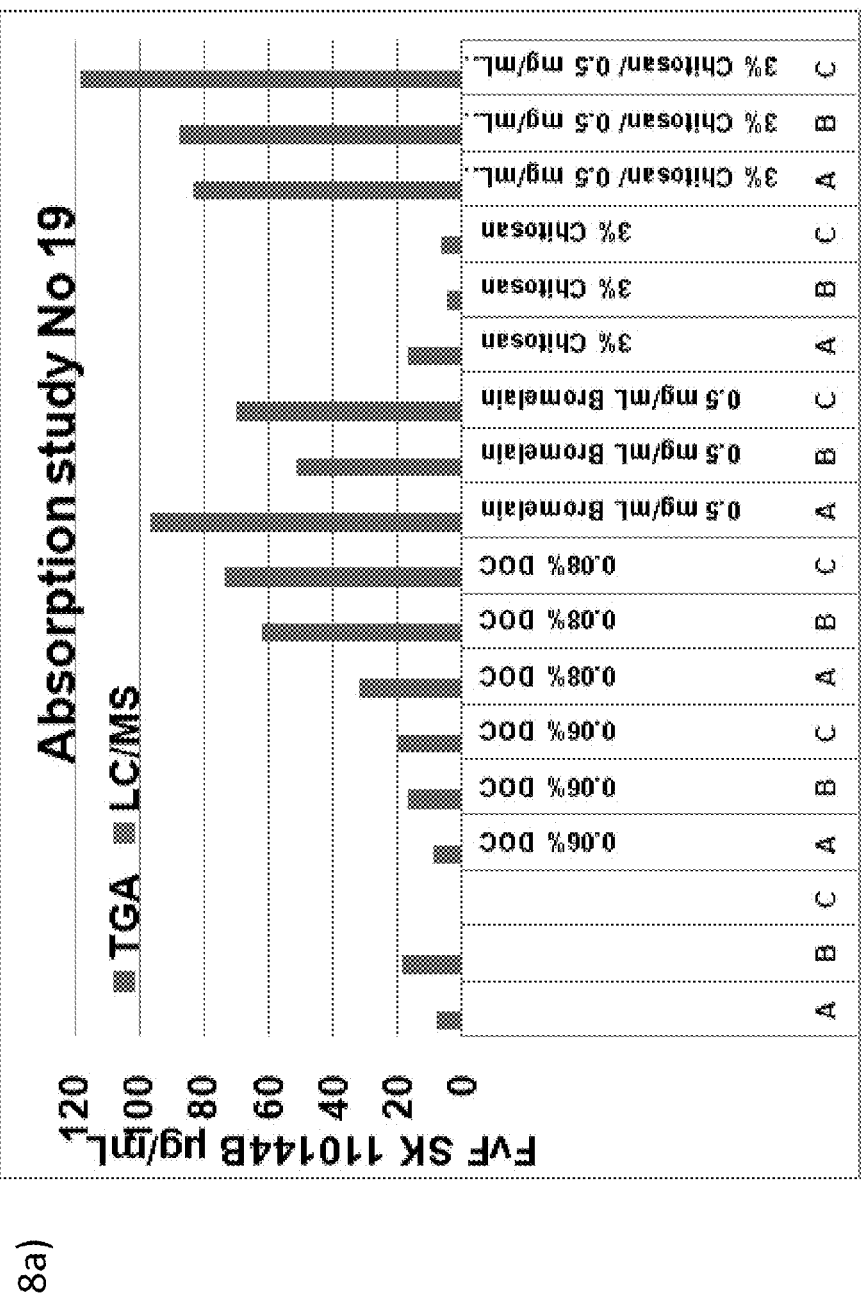
FIGS. 8a-b show an example of resorption data acquired in the CaCo-2 bioavailability screening for fucoidan FvF SK110144B in combination with gastrointestinal epithelial barrier permeation enhancers.
Figure 8B:
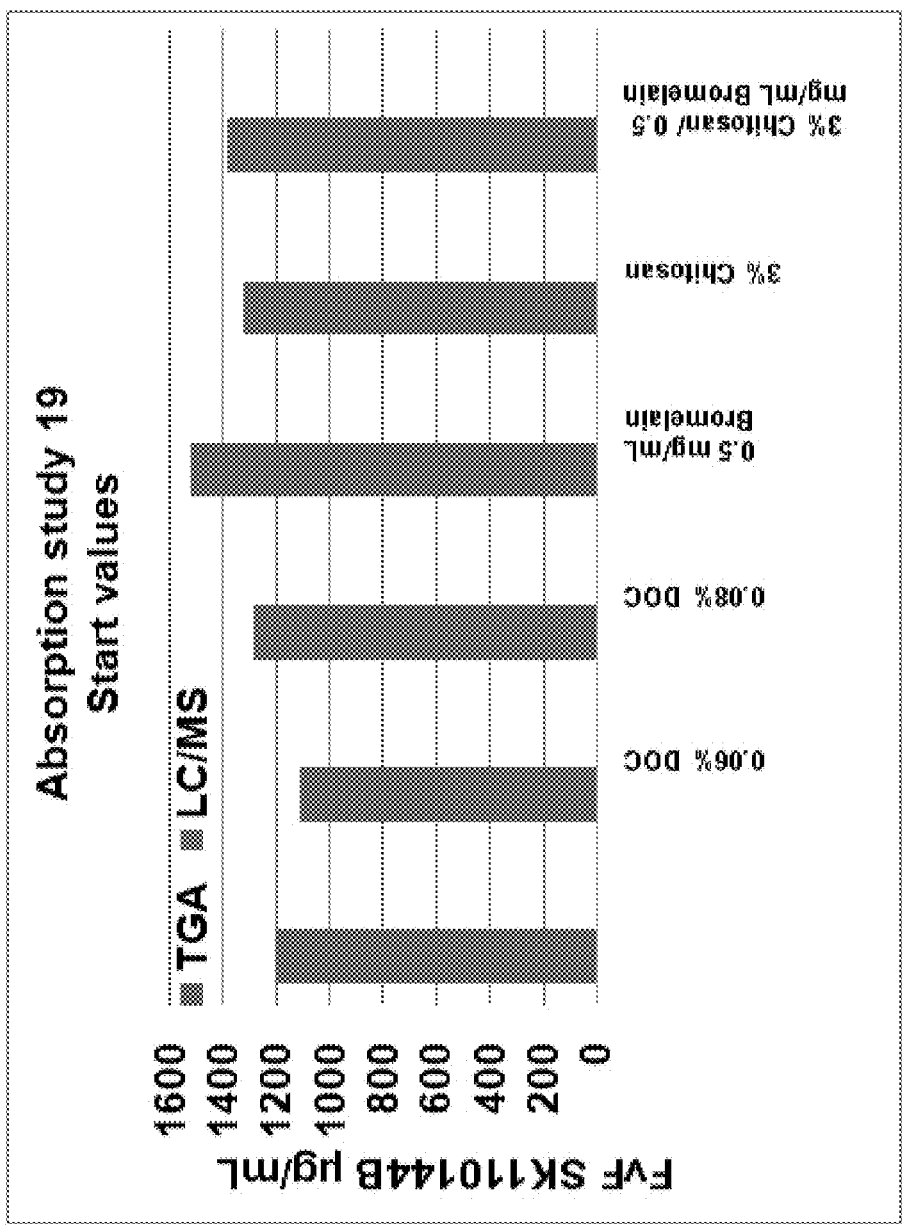

FIGS. 8a-b show the NASP, Fucoidan FvF SK110144B resorption in Caco-2 cell models in the absence of any gastrointestinal epithelial barrier permeation enhancer as well as in the presence of gastrointestinal epithelial barrier permeation enhancers deoxycholate (at two different concentrations), bromelain, chitosan and in the presence of a combination of bromelain and chitosan. FIGS. 8a-b demonstrates that the basolateral concentrations of Fucoidan FvF SK110144B increased in the presence of a gastrointestinal epithelial barrier permeation enhancer, indicating that resorption of Fucoidan FvF SK110144B increases when administered in combination with a gastrointestinal epithelial barrier permeation enhancer. In particular, the resorption of Fucoidan FvF SK110144B increased substantially in the presence of 0.08% deoxycholate, bromelain, and in the presence of a combination of chitosan and bromelain.

Figure 14A:
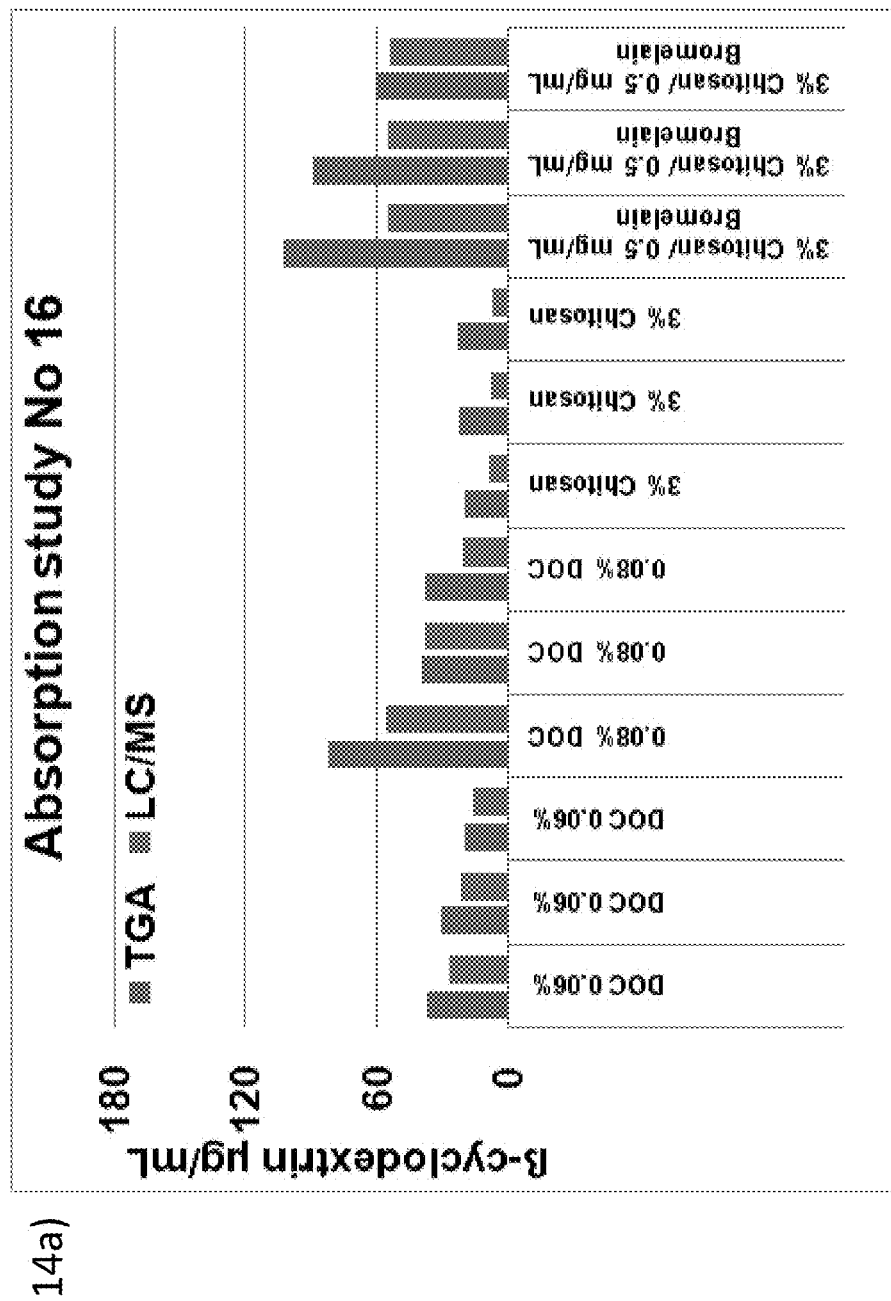
FIGS. 14a-b show an example of resorption data acquired in the CaCo-2 bioavailability screening for fucoidan β-cyclodextrin in combination with gastrointestinal epithelial barrier permeation enhancers.
Figure 14B:
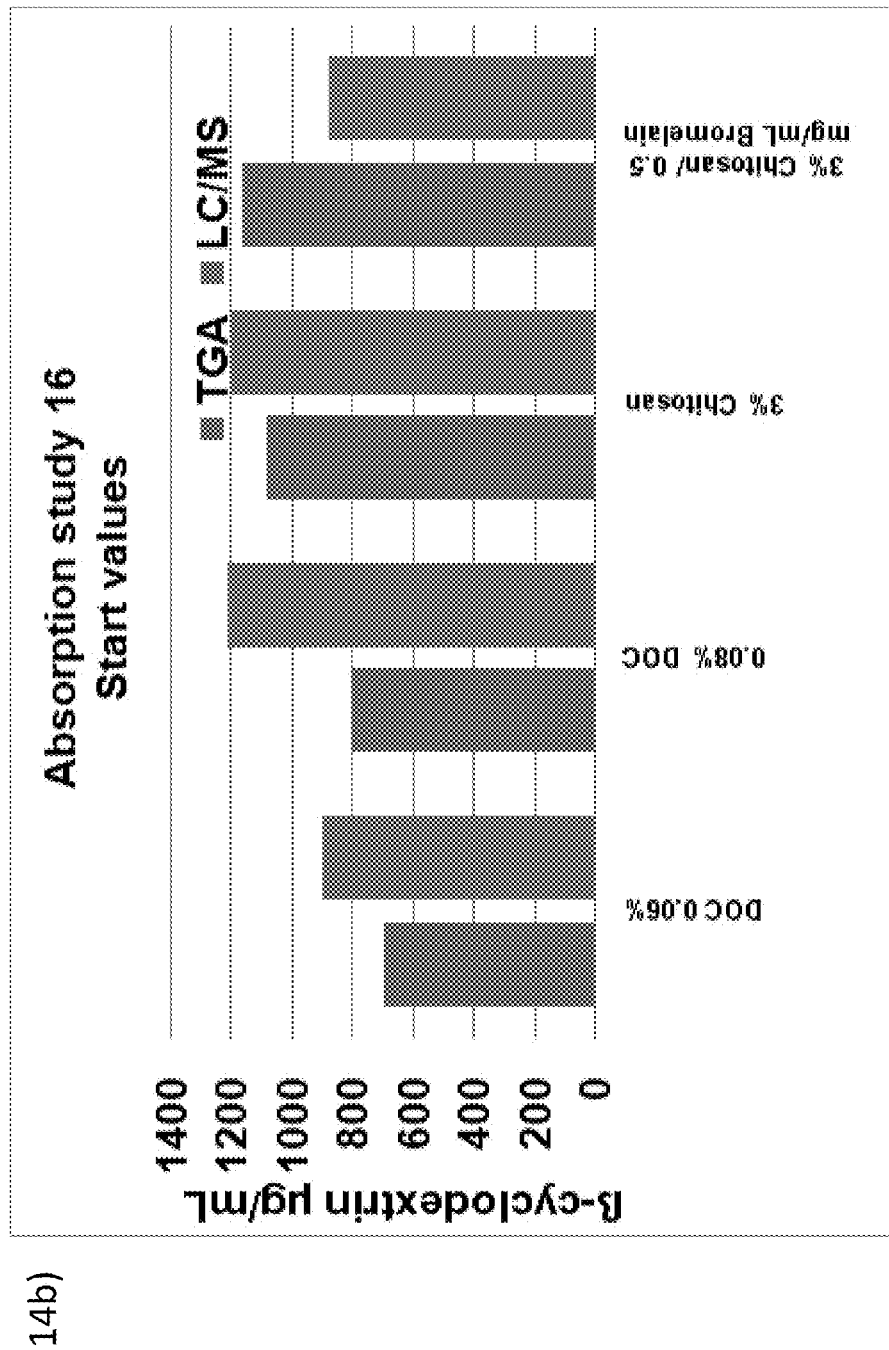

FIGS. 9 and 14 show the synthetic NASP, sulfated β-cyclodextrin resorption in Caco-2 cell models in the absence of any gastrointestinal epithelial barrier permeation enhancer as well as in the presence of gastrointestinal epithelial barrier permeation enhancers deoxycholate, bromelain and sodium caprate. FIG. 9 demonstrates that the basolateral concentrations of sulfated β-cyclodextrin increased in the presence of a gastrointestinal epithelial barrier permeation enhancer, indicating that resorption of sulfated β-cyclodextrin increases mg/mL bromelain. As illustrated in FIGS. 10a-b, a combination of 3% chitosan and 0.5 mg/mL bromelain demonstrated the strongest resorption of the NASP.

Table 6 is a summary of percent resorption of natural and synthetic NASPs in the Caco-2 cell model. As shown in Table 4, all of the NASPs demonstrated increased resorption in the presence of the gastrointestinal epithelial barrier permeation enhancers of interest.

TABLE 6

| Avg. Resorption at 8 hours (%) | BAX513 | F.v. L/FVF 1091 | U.p. 5508005 | F.v. DS1001108B | Sulfated β-cyclodextrin | Sulfated Maltopentaose |
|---|---|---|---|---|---|---|
| MW | 180 kD | 143 kD | 380 kD | 18 kD | 3 kD | 3 kD |
| No enhancer | 0.3 | 0.6 | 0.1 | 2.3 | 0 | 0 |
| Sodium Caprate (12 mM) | 0.4 | 3.7 | 3.5 | n/a | 19.3 | 13.1 |
| Deoxycholate (0.06%) | n/a | n/a | n/a | n/a | 20.6 | 67.4 |
| Deoxycholate (0.08%) | 1.4 | 14.5 | 4.7 | 18.2 | 36.1 | 113.2 |
| Bromelain (0.5 mg/mL) | 11.3 | 9.5 | 6.2 | n/a | 24.7 | 48.6 |
| Chitosan (3%) | 0.8 | 1.6 | 2.5 | 2.0 | 15.6 | 35.7 |
| Bromelain (0.5 mg/mL) and Chitosan (3%) | 9.9 | 36.7 | 19.6 | 27.2 | 59.8 | 158.8 | when administered in combination with a gastrointestinal epithelial barrier permeation enhancer. In particular, the resorption of sulfated β-cyclodextrin increased substantially in the presence of all three of deoxycholate, bromelain, and sodium caprate at 8 hours.

Figure 15A:
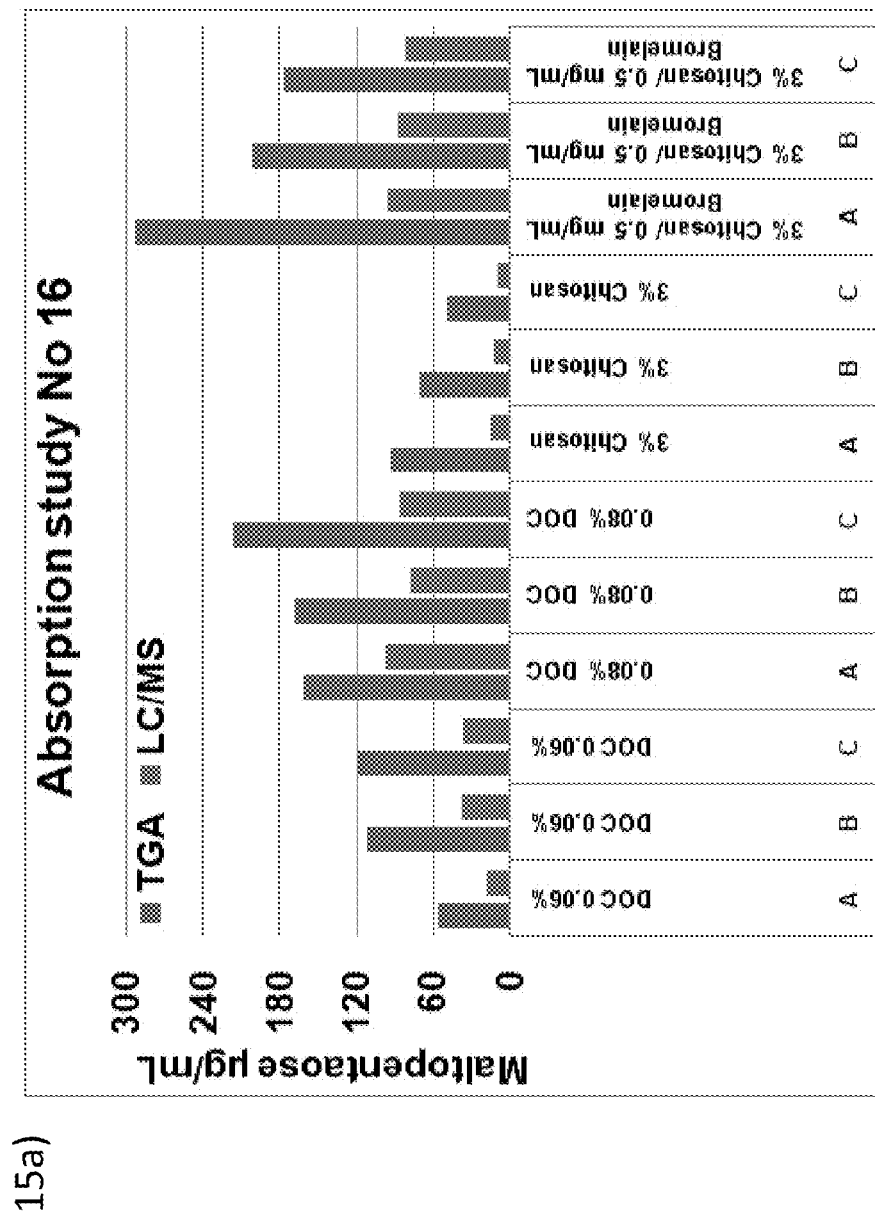
FIGS. 15a-b show an example of resorption data acquired in the CaCo-2 bioavailability screening for fucoidan sulfated maltopentaose in combination with gastrointestinal epithelial barrier permeation enhancers.
Figure 15B:
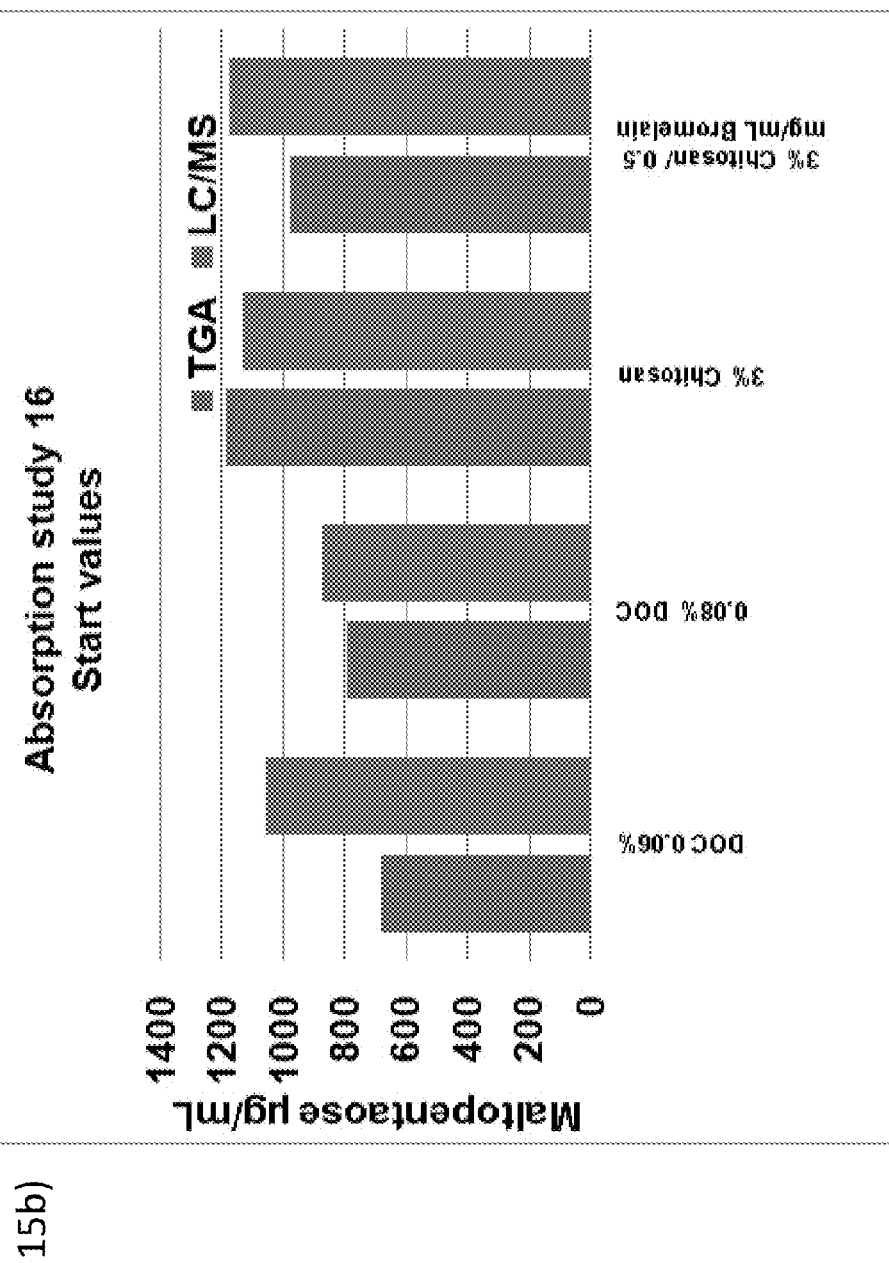

FIGS. 10 and 15 show the synthetic NASP, sulfated maltopentaose resorption in Caco-2 cell models in the absence of any gastrointestinal epithelial barrier permeation enhancer as well as in the presence of gastrointestinal epithelial barrier permeation enhancers deoxycholate, bromelain, chitosan and sodium caprate. FIG. 10 demonstrates that the basolateral concentrations of sulfated maltopentaose increased in the presence of a gastrointestinal epithelial barrier permeation enhancer, indicating that resorption of sulfated maltopentaose increases when administered in combination with a gastrointestinal epithelial barrier permeation enhancer. In particular, the resorption of sulfated maltopentaose increased substantially in the presence of deoxycholate and bromelain at 8 hours. Sulfated maltopentaose also showed strong increased resorption in the presence of chitosan and sodium caprate.

As demonstrated in FIGS. 4-10, the basolateral concentrations of both natural and synthetic NASPs are increased in the presence of each of the gastrointestinal epithelial barrier permeation enhancers, indicating that resorption of the NASP increases when administered in combination with a gastrointestinal epithelial barrier permeation enhancer as compared to resorption in the absence of gastrointestinal epithelial barrier permeation enhancer.

Figure 11A:
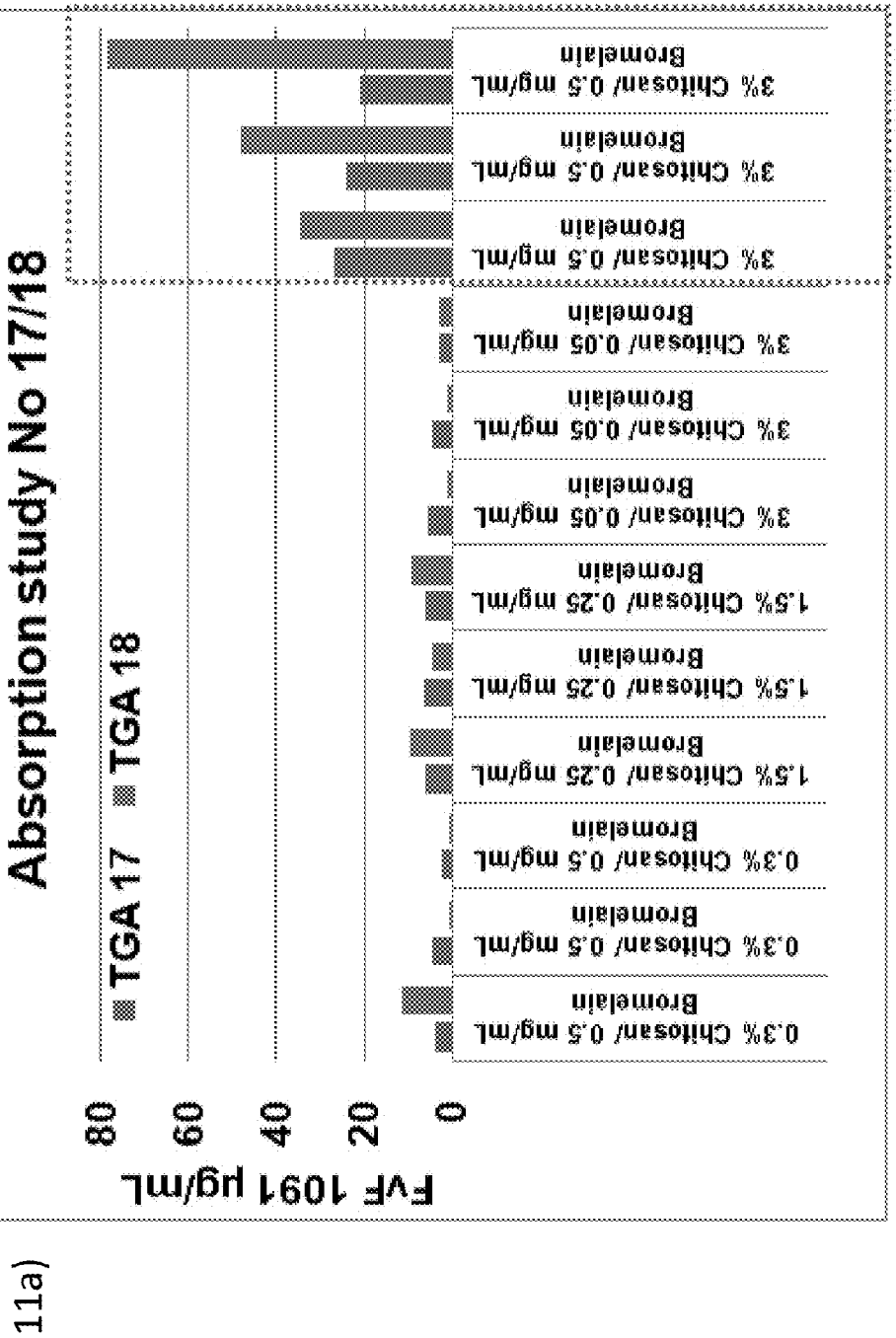
FIGS. 11a-b show an example of resorption data acquired in the CaCo-2 bioavailability screening for fucoidans F.v. L/FVF-1091 and F.v.F DS1001108B in combination with gastrointestinal epithelial barrier permeation enhancers at varying concentrations.
Figure 11B:
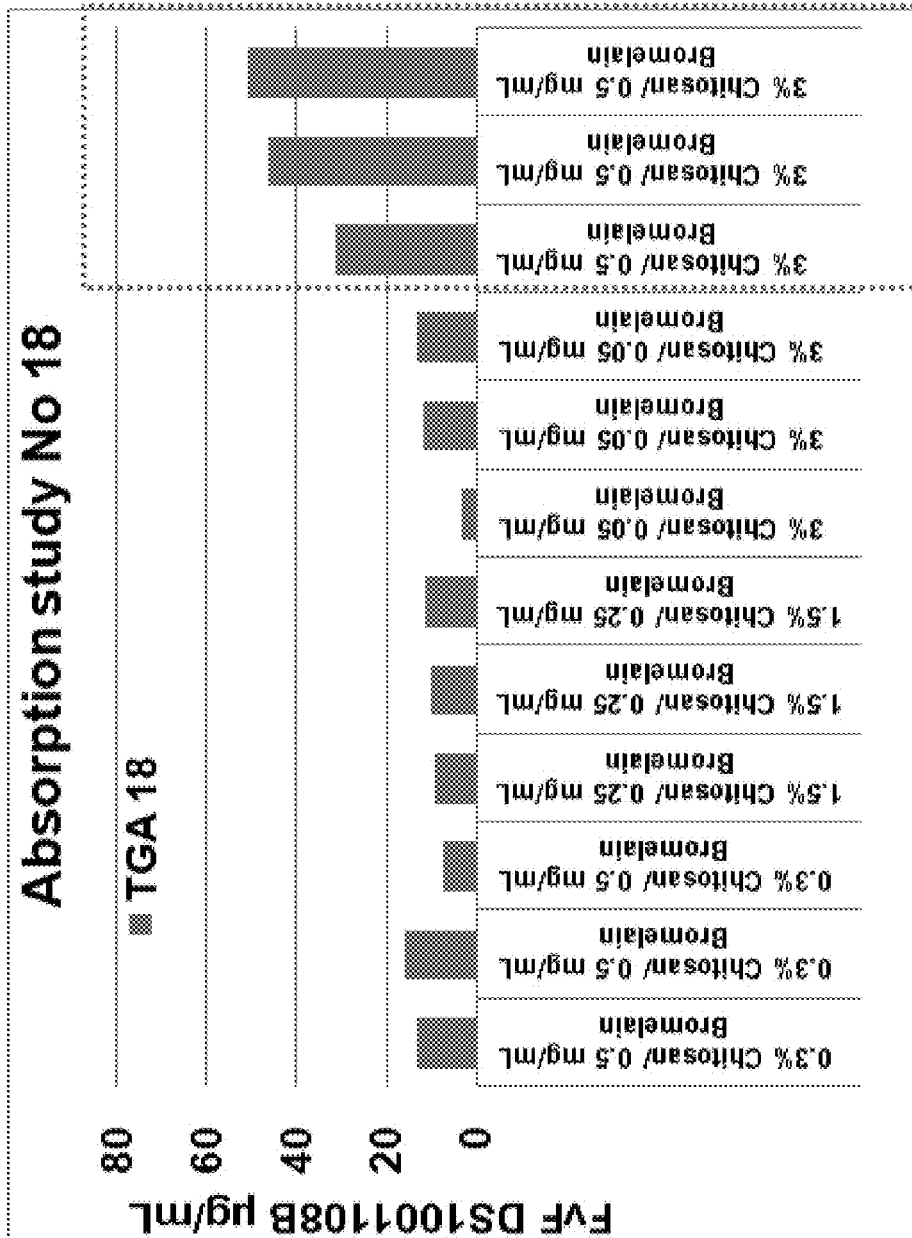

FIGS. 11a-b illustrates the effect of different concentrations of chitosan and bromelain when a combination of chitosan and bromelain is employed in combination with NASPs Fucoidan F.v. L/FVF 1091 (FIG. 11a) and Fucoidan FvF DS1001108B (FIG. 11b). In particular, combinations of chitosan and bromelain include 0.3% chitosan and 0.5 mg/ml bromelain; 1.5% chitosan and 0.25 mg/mL bromelain; 3% chitosan and 0.05 mg/mL bromelain; and 3% chitosan and 0.5

Figure 12A:
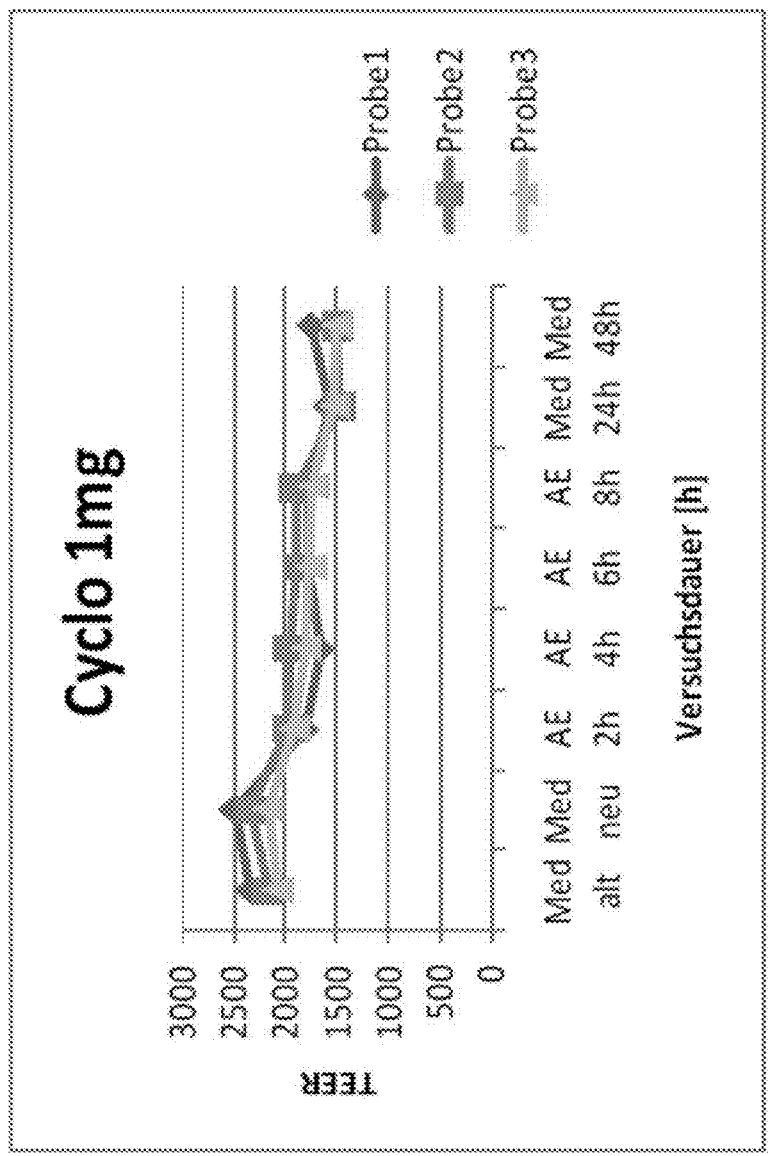
FIGS. 12a-b shows the condition of the cell layer in the CaCo-2 bioavailability screening for synthetic NASP sulfated β-cyclodextrin in the absence and in combination with the gastrointestinal epithelial barrier permeation enhancer bromelain as measured by transepithelial electrical resistance.
Figure 12B:
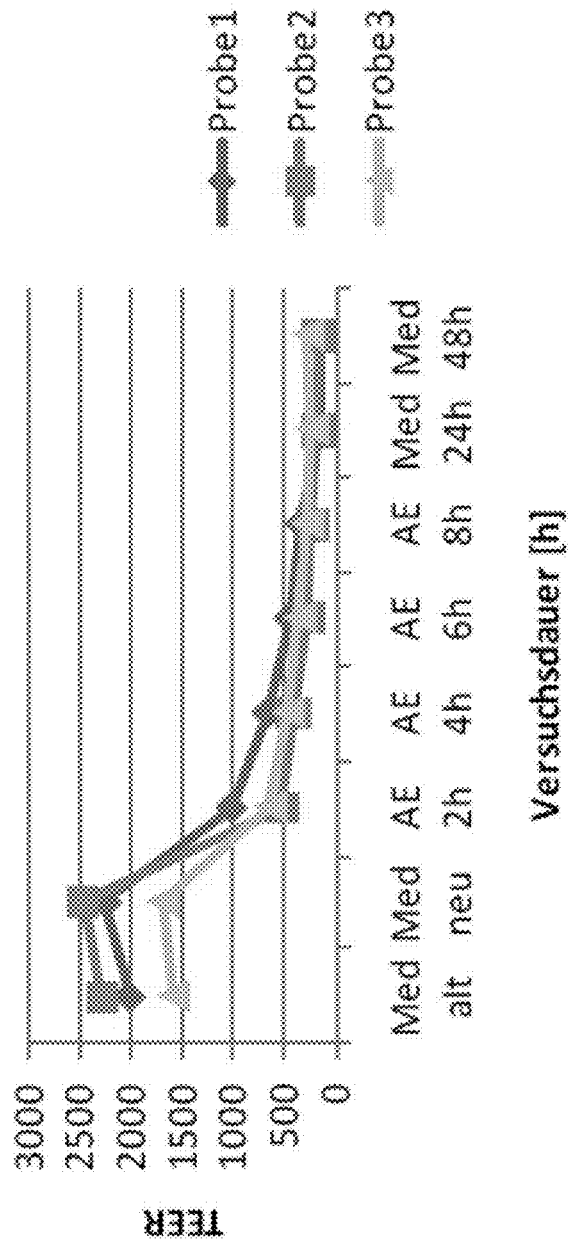
Figure 13A:
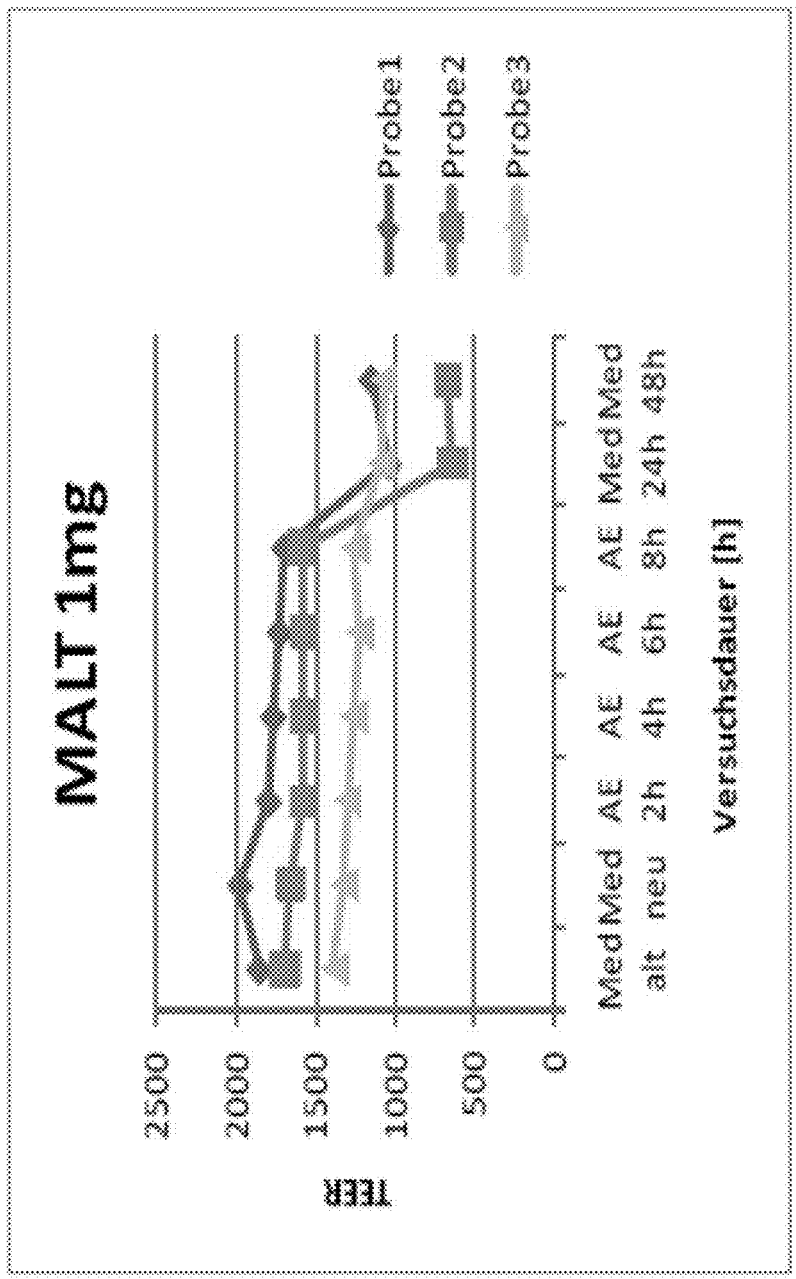
FIGS. 13a-c shows the condition of the cell layer in the CaCo-2 bioavailability screening for synthetic NASP sulfated maltopentaose in the absence and in combination with the gastrointestinal epithelial barrier permeation enhancers deoxycholate and chitosan as measured by transepithelial electrical resistance.
Figure 13B:
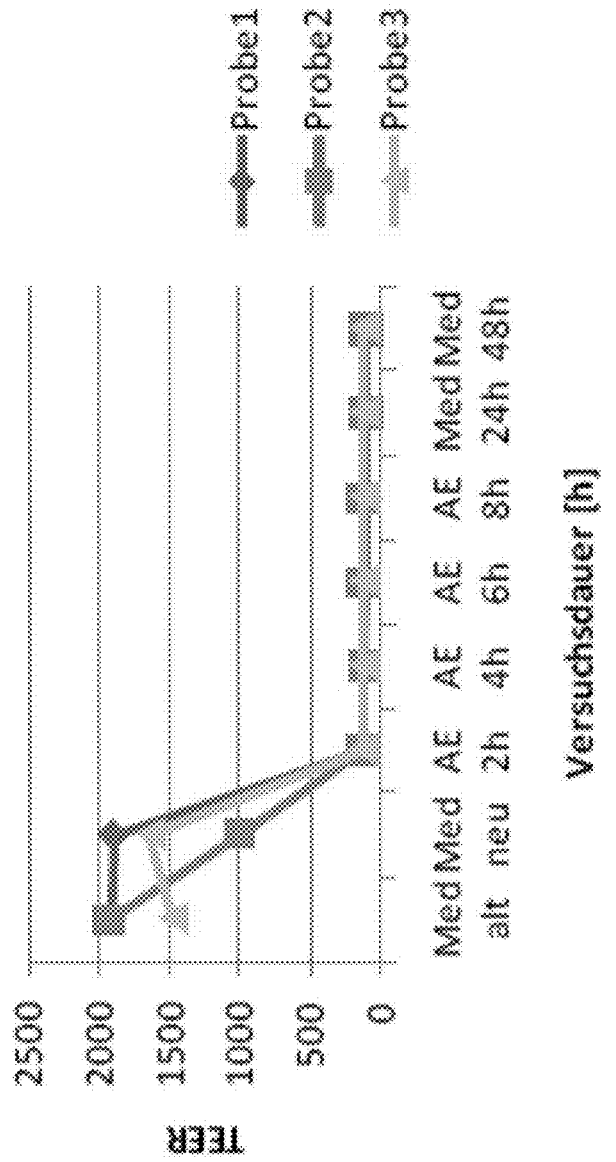
Figure 13C:
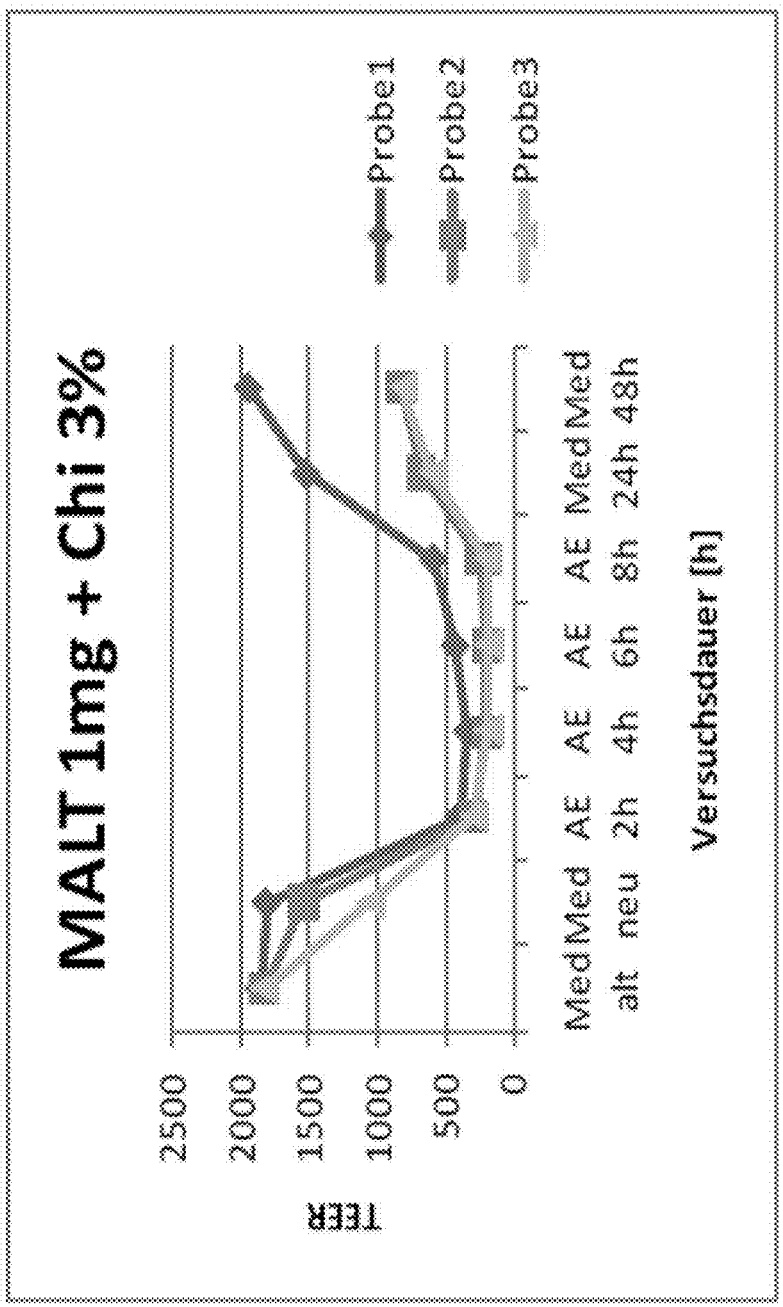

FIGS. 12a-b and 13a-c shows the condition of the cell layer as measured by transepithelial electrical resistance in the presence and absence of a gastrointestinal epithelial barrier permeation enhancers when tested with sulfated β-cyclodextrin and sulfated maltopentose, respectively. As depicted in FIGS. 12a-b, in the presence of sulfated β-cyclodextrin, gastrointestinal epithelial barrier permeation enhancer bromelain reduce the transepithelial electrical resistance values substantially (<300 ohms/cm$^2$). The transepithelial electrical resistance values remained low after addition of fresh medium. Treatment with the gastrointestinal epithelial barrier permeation enhancer alone however, resulted in the recovery of the transepithelial electrical resistance. Likewise, as depicted in FIGS. 13a-c, in the presence of sulfated maltaptentose, gastrointestinal epithelial barrier permeation enhancers bromelain, deoxycholate and chitosan reduce the transepithelial electrical resistance values substantially. However, in contrast to studies as depicted in FIGS. 12a-b for sulfated β-cyclodextrin, the transepithelial electrical resistance increased after removal of the gastrointestinal epithelial barrier permeation enhancer and the maltopentaose.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the embodiments shown and described herein. Rather, the scope and spirit of present invention is embodied by the appended claims.

What is claimed is:

1. A method of enhancing blood coagulation in a subject, the method comprising:
    orally administering to the subject a procoagulant amount of a non-anticoagulant sulfated polysaccharide (NASP) selected from the group consisting of N-acetyl-heparin (NAH), N-acetyl-de-O-sulfated-heparin (NA-de-o-SH), de-N-sulfated-heparin (De-NSH), de-N-sulfated-acetylated-heparin (De-NSAH), periodate-oxidized heparin (POH), chemically sulfated laminarin (CSL), chemically sulfated alginic acid (CSAA), chemically sulfated pectin (CSP), dextran sulfate (DXS), heparin-derived oligosaccharides (HDO), pentosan polysulfate (PPS), fucoidans, sulfated maltopentoses, sulfated beta-cyclodextrins, sulfated 6-Carboxyicodextrin in combination with a gastrointestinal epithelial barrier permeation enhancer in a manner sufficient to enhance blood coagulation in the subject,
    wherein the gastrointestinal epithelial barrier permeation enhancer comprises a ratio of chitosan to bromelain sufficient to enhance permeation 2-fold or greater than would be achieved by the sum of chitosan or bromelain individually.

2. The method according to claim 1, wherein the amount of NASP administered to the subject ranges from 0.01 mg/kg to about 100 mg/kg.

3. The method according to claim 1, wherein the gastrointestinal epithelial barrier permeation enhancer comprises about 0.3% to about 3% chitosan and about 0.05 mg/mL to about 0.5 mg/mL bromelain.

4. The method according to claim 3, wherein the gastrointestinal epithelial barrier permeation enhancer comprises about 3% chitosan and about 0.5 mg/mL bromelain.

5. The method according to claim 1, wherein the method further comprising administering to the subject one or more factors selected from the group consisting of factor XI, factor XII, prekallikrein, high molecular weight kininogen (HMWK), factor V, factor VII, factor VIII, factor IX, factor X, factor XIII, factor II, von Willebrands factor, tissue factor, factor VIIa, factor Va, and factor Xa, factor IXa, factor XIa, factor XIIa, and VIIIa.

6. The method according to claim 1, wherein the NASP is a fucoidan.

7. The method according to claim 6, wherein the fucoidan is selected from the group consisting of Fucoidan 5307002, *Fucus vesiculosus*, max. MW peak 126.7 kD; Fucoidan VG49, *Fucus vesiculosus*, hydrolyzed sample of 5307002 of lower MW, max. MW peak 22.5 kD; Fucoidan VG57, *Undaria pinnatifida*, high charge (high sulphation, deacetylated); Fucoidan GFS (5508005), *Undaria pinnatifida*, depyrogenated; Fucoidan GFS (L/FVF-01091), *Fucus vesiculosus*, depyrogenated, max. MW peak 125 kD; Fucoidan GFS (L/FVF-01092), *Fucus vesiculosus*, depyrogenated, max. MW peak 260 kD; Fucoidan GFS (L/FVF-01093) and combinations thereof.

8. The method according to claim 1, wherein the gastrointestinal epithelial barrier permeation enhancer comprises a ratio of chitosan to bromelain sufficient to enhance permeation 3-fold or greater than would be achieved by the sum of chitosan or bromelain individually.

9. The method according to claim 1, wherein the gastrointestinal epithelial barrier permeation enhancer comprises a ratio of chitosan to bromelain of from 5:1 to 500:1.

10. The method according to claim 7, wherein the gastrointestinal epithelial barrier permeation enhancer comprises a ratio of chitosan to bromelain of 5:1.

11. The method according to claim 1, wherein chitosan is acylated chitosan.

12. The method according to claim 1, wherein the subject has a bleeding disorder selected from the group consisting of a chronic or acute bleeding disorder, a congenital coagulation disorder caused by a blood factor deficiency, and an acquired coagulation disorder.

13. The method claim 12, wherein the bleeding disorder is a blood factor deficiency of one or more factors selected from the group consisting of factor V, factor VII, factor VIII, factor IX, factor X, factor XI, factor XII, factor XIII, and von Willebrand factor; a fibrinogen disorder; a prothrombin disorder; or a platelet dysfunction.

14. The method according to claim 1, wherein the subject is in need of enhanced blood coagulation because of prior administration of an anticoagulant.

15. The method according to claim 14, wherein the anticoagulant is selected from the group consisting of heparin, a coumarin derivative, tissue factor pathway inhibitor (TFPI), antithrombin III, lupus anticoagulant, nematode anticoagulant peptide (NAPc2), active-site blocked factor VIIa (factor VIIai), factor IXa inhibitors, factor Xa inhibitor, factor Va inhibitor, factor VIIIa inhibitor, thrombin inhibitor, and an antibody that binds a clotting factor selected from the group consisting of Factor V, Factor VII, Factor VIII, Factor IX, Factor X, Factor XIII, Factor II, Factor XI, Factor XII, von Willebrands factor, prekallikrein, and high molecular weight kininogen (HMWK).

16. The method according to claim 1, wherein the method is a method of inhibiting TFPI activity in the subject.

* * * * *